United States Patent
Nissen et al.

(10) Patent No.: US 7,550,566 B2
(45) Date of Patent: *Jun. 23, 2009

(54) G-CSF CONJUGATES

(75) Inventors: Torben Lauesgaard Nissen, London (GB); Kim Vilbour Andersen, Broenshoej (DK); Christian Karsten Hansen, Vedbaek (DK); Jan Moller Mikkelsen, Gentofte (DK); Hans Thalsgaard Schambye, Frederiksberg (DK)

(73) Assignee: Maxygen Holdings Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 11/463,863

(22) Filed: Aug. 10, 2006

(65) Prior Publication Data

US 2007/0010660 A1    Jan. 11, 2007

Related U.S. Application Data

(60) Division of application No. 11/004,461, filed on Dec. 3, 2004, now abandoned, which is a continuation of application No. 10/192,294, filed on Jul. 10, 2002, now Pat. No. 6,831,158, which is a continuation-in-part of application No. 09/904,196, filed on Jul. 11, 2001, now Pat. No. 6,555,660, which is a continuation-in-part of application No. 09/760,008, filed on Jan. 10, 2001, now Pat. No. 6,646,110.

(60) Provisional application No. 60/215,644, filed on Jun. 30, 2000, provisional application No. 60/189,506, filed on Mar. 15, 2000, provisional application No. 60/176,376, filed on Jan. 14, 2000.

(30) Foreign Application Priority Data

| Jan. 10, 2000 | (DK) | ................................ 2000 00024 |
| Mar. 2, 2000 | (DK) | ................................ 2000 00341 |
| Jun. 16, 2000 | (DK) | ................................ 2000 00943 |
| Mar. 22, 2002 | (DK) | ................................ 2002 00447 |
| May 8, 2002 | (DK) | ................................ 2002 00708 |

(51) Int. Cl.
C07K 14/535 (2006.01)
C07K 1/107 (2006.01)
A61K 38/00 (2006.01)
C07H 21/00 (2006.01)

(52) U.S. Cl. .................... 530/351; 530/350; 530/402; 514/2; 536/23.5

(58) Field of Classification Search ................ None
See application file for complete search history.

(56) References Cited

U.S. PATENT DOCUMENTS

| 4,810,643 A | 3/1989 | Souza |
| 4,833,127 A | 5/1989 | Ono et al. |
| 4,853,871 A | 8/1989 | Pantoliano et al. |
| 4,904,584 A | 2/1990 | Shaw |
| 4,908,773 A | 3/1990 | Pantoliano et al. |
| 4,999,291 A | 3/1991 | Souza |
| 5,023,802 A | 6/1991 | Fujita |
| 5,025,388 A | 6/1991 | Cramer et al. |
| 5,104,651 A | 4/1992 | Boone |
| 5,109,119 A | 4/1992 | Reichert et al. |
| 5,157,736 A | 10/1992 | Boyer et al. |
| 5,214,132 A | 5/1993 | Kuga et al. |
| 5,218,092 A | 6/1993 | Sasaki et al. |
| 5,265,030 A | 11/1993 | Skolnick et al. |
| 5,281,698 A | 1/1994 | Nitecki |
| 5,307,287 A | 4/1994 | Cramer et al. |
| 5,320,840 A | 6/1994 | Camble et al. |
| 5,349,052 A | 9/1994 | Delgado et al. |
| 5,362,853 A | 11/1994 | Kuga et al. |
| 5,386,507 A | 1/1995 | Teig et al. |
| 5,399,345 A | 3/1995 | Schumacher et al. |
| 5,416,195 A | 5/1995 | Camble et al. |
| 5,424,963 A | 6/1995 | Turner et al. |
| 5,436,850 A | 7/1995 | Eisenberg et al. |
| 5,448,498 A | 9/1995 | Namiki et al. |
| 5,476,653 A | 12/1995 | Pitt et al. |
| 5,555,366 A | 9/1996 | Teig et al. |

(Continued)

FOREIGN PATENT DOCUMENTS

AU        631312 B       11/1992

(Continued)

OTHER PUBLICATIONS

De Haan, G., et al., *British Journal of Haematology* (2000) 110(3):638-646.

(Continued)

*Primary Examiner*—Zachariah Lucas
(74) *Attorney, Agent, or Firm*—Sharon M. Fujita; Joanne R. Petithory; Norman J. Kruse

(57) ABSTRACT

Polypeptide conjugates with G-CSF activity comprising a polypeptide having at least one introduced lysine residue and at least one removed lysine residue compared to the sequence of human G-CSF, and which are conjugated to 2-6 polyethylene glycol moieties. The conjugates have a low in vitro bioactivity, a long in vivo half-life, a reduced receptor-mediated clearance, and provide a more rapid stimulation of production of white blood cells and neutrophils than non-conjugated recombinant human G-CSF.

30 Claims, 11 Drawing Sheets

U.S. PATENT DOCUMENTS

| | | | |
|---|---|---|---|
| 5,580,755 A | 12/1996 | Souza | |
| 5,581,476 A | 12/1996 | Osslund | |
| 5,582,823 A | 12/1996 | Souza | |
| 5,589,456 A | 12/1996 | Smith et al. | |
| 5,597,562 A | 1/1997 | Nomura et al. | |
| 5,676,941 A | 10/1997 | Souza | |
| 5,681,720 A | 10/1997 | Kuga et al. | |
| 5,714,581 A | 2/1998 | Kuga et al. | |
| 5,738,849 A | 4/1998 | Bauer et al. | |
| 5,772,992 A | 6/1998 | Bauer et al. | |
| 5,773,581 A | 6/1998 | Camble et al. | |
| 5,790,421 A | 8/1998 | Osslund | |
| 5,795,968 A | 8/1998 | Kuga et al. | |
| 5,817,486 A | 10/1998 | Bauer et al. | |
| 5,824,778 A | 10/1998 | Ishikawa et al. | |
| 5,824,784 A | 10/1998 | Kinstler et al. | |
| 5,830,705 A | 11/1998 | Souza | |
| 5,840,521 A | 11/1998 | Barth | |
| 5,858,347 A | 1/1999 | Bauer et al. | |
| 5,880,255 A | 3/1999 | Delgado et al. | |
| 5,883,230 A | 3/1999 | Schendel | |
| 5,985,263 A | 11/1999 | Lee et al. | |
| 5,985,265 A | 11/1999 | Kinstler et al. | |
| 5,997,860 A | 12/1999 | Bauer et al. | |
| 6,004,548 A | 12/1999 | Souza | |
| 6,017,523 A | 1/2000 | Bauer et al. | |
| 6,022,535 A | 2/2000 | Bauer et al. | |
| 6,027,720 A | 2/2000 | Kuga et al. | |
| 6,030,812 A | 2/2000 | Bauer et al. | |
| 6,051,217 A | 4/2000 | Bauer et al. | |
| 6,057,133 A | 5/2000 | Bauer et al. | |
| 6,060,047 A | 5/2000 | Bauer et al. | |
| 6,066,318 A | 5/2000 | Feng | |
| 6,074,639 A | 6/2000 | Bauer et al. | |
| 6,093,395 A | 7/2000 | Bauer et al. | |
| 6,100,070 A | 8/2000 | Zurfluh et al. | |
| 6,132,991 A | 10/2000 | Bauer et al. | |
| 6,153,183 A | 11/2000 | Bauer et al. | |
| 6,166,183 A | 12/2000 | Ishikawa et al. | |
| 6,204,364 B1 | 3/2001 | Todaro et al. | |
| 6,261,550 B1 | 7/2001 | Osslund | |
| 6,379,661 B1 | 4/2002 | Souza | |
| 6,420,339 B1 | 7/2002 | Gegg | |
| 6,555,660 B2 * | 4/2003 | Nissen et al. | 530/397 |
| 6,632,426 B2 | 10/2003 | Osslund | |
| 6,646,110 B2 * | 11/2003 | Nissen et al. | 530/397 |
| 6,831,158 B2 * | 12/2004 | Nissen et al. | 530/397 |
| 7,381,804 B2 | 6/2008 | Osslund | |
| 2002/0142964 A1 | 10/2002 | Nissen et al. | |
| 2003/0204057 A1 | 10/2003 | Ishikawa et al. | |

FOREIGN PATENT DOCUMENTS

| | | |
|---|---|---|
| AU | 641081 B | 9/1993 |
| EP | 0243153 A2 | 10/1987 |
| EP | 0 256 843 | 2/1988 |
| EP | 0272703 A1 | 6/1988 |
| EP | 0 335 423 | 10/1989 |
| EP | 0 215 126 | 7/1991 |
| EP | 0 220 520 | 9/1991 |
| EP | 0459630 A2 | 12/1991 |
| EP | 0473268 A2 | 3/1992 |
| EP | 0490584 A2 | 6/1992 |
| EP | 0502637 A2 | 9/1992 |
| EP | 0 344 796 | 9/1994 |
| EP | 0 230 980 | 3/1996 |
| EP | 0401384 B1 | 3/1996 |
| EP | 0 744 409 | 11/1996 |
| EP | 0 370 205 | 7/1998 |
| EP | 0733067 B1 | 5/1999 |
| EP | 0 921 131 | 6/1999 |
| EP | 0 237 545 | 8/1999 |
| EP | 0 169 566 | 7/2000 |
| EP | 0 612 846 | 8/2000 |
| EP | 1 167 390 A1 | 1/2002 |
| GB | 2213821 A | 8/1989 |
| GB | 2246295 A | 7/1991 |
| WO | 85/00817 A1 | 2/1985 |
| WO | 87/01132 A1 | 2/1987 |
| WO | 88/01775 A1 | 3/1988 |
| WO | WO 89/05824 | 6/1989 |
| WO | WO 89/10932 | 11/1989 |
| WO | WO 90/12874 | 11/1990 |
| WO | WO 91/05798 | 5/1991 |
| WO | 92/04455 A1 | 3/1992 |
| WO | 9221029 A1 | 11/1992 |
| WO | 9301484 A1 | 1/1993 |
| WO | 93/25687 A1 | 12/1993 |
| WO | WO 94/20069 | 9/1994 |
| WO | 95/20976 A1 | 8/1995 |
| WO | 95/20977 A1 | 8/1995 |
| WO | 95/21197 A1 | 8/1995 |
| WO | 95/21254 A1 | 8/1995 |
| WO | WO 95/21629 | 8/1995 |
| WO | 95/27732 A2 | 10/1995 |
| WO | WO 96/11953 | 4/1996 |
| WO | 96/23888 A1 | 8/1996 |
| WO | 97/12978 A1 | 4/1997 |
| WO | 97/12985 A2 | 4/1997 |
| WO | WO 97/11957 * | 4/1997 |
| WO | WO 97/12977 | 4/1997 |
| WO | 98/17810 A2 | 4/1998 |
| WO | 98/18923 A1 | 5/1998 |
| WO | 98/18924 A1 | 5/1998 |
| WO | 98/46750 A1 | 10/1998 |
| WO | WO 98/53072 | 11/1998 |
| WO | WO 99/03887 | 1/1999 |
| WO | WO 99/67291 | 12/1999 |
| WO | 00/18905 A1 | 4/2000 |
| WO | WO 00/40728 | 7/2000 |
| WO | WO 00/44785 | 8/2000 |
| WO | WO 00/52057 A1 | 9/2000 |
| WO | WO 01/04329 A1 | 1/2001 |
| WO | WO 01/51510 A2 | 7/2001 |
| WO | WO 02/20751 A2 | 3/2002 |
| WO | WO 02/20766 A2 | 3/2002 |
| WO | WO 02/20767 A2 | 3/2002 |
| WO | WO 02/28896 A1 | 4/2002 |
| WO | WO 02/36626 | 5/2002 |

OTHER PUBLICATIONS

Viens, P., et al., "Randomized, Controlled, Dose-Range Study of Ro 25-8315 Given Before and After a High-Dose Combination Chemotherapy Regimen in Patients with Metastatic or Recurrent Breast Cancer Patients," *J. Clinical Oncology*, 20(1):24-36 (2002).

Eliason J.F., et al. Extended activity in cynomolgus monkeys of a granulocyte colony-stimulating factor mutein conjugated with high molecular weight polyethylene glycol. Stem Cells, Jan. 2000, vol. 18, No. 1, 40-45.

Delgado, Cristina, et al., "The Uses and Properties of PEG-Linked Proteins" *Critical Reviews in Therapeutic Drug Carrier Systems* 9 (3, 4): 249-304 (1992).

Young, Dennis C., et al., "Characterization of the receptor binding determinants of granulocyte colony stimulating factor" *Protein Science* (1997), 6:1228-1236.

Yamasaki, M., et al., "Effect of Divalent Polyethylene Glycol Units, Conjugated on Human Granulocyte Colony-Stimulating Factor, on Biological Activities In Vitro and In Vivo," Drugs Exptl. Clin. Res. 24(4):191-196 (1998).

Aritomi et al., *Nature* 401:713-717 (1999).

Bowen et al., *Experimental Hematology* 27: 425-432 (1999).

Hill et al., *Proc. Natl. Acad. Sci. USA* 90: 5167-5171 (1993).

Horan et al., *Biochemistry* 35(15): 4886-4896 (1996).

Nagata et al., *Nature* 319:415-418 (1986).
Riedhaar-Olson et al., *Biochemistry* 35: 9034-9041 (1996).
Satake-Ishikawa et al., *Cell Structure and Function* 17:157-160 (1992).
Souza et al., *Science* 232: 61-65 (1986).
Zink et al., *Biochemistry* 33: 8453-8463 (1994).
Li, T, et al. Conformational Changes in G-CSF/Receptor Complex as Investigated by Isotope-Edited FTIR Spectroscopy. Biochemistry 1997; 36(29):8849-8857.
Osslund, TD. The Structure of Granulocyte-Colony Stimulating Factor. Ph.D. Thesis, University of California Los Angeles, 1993.
Zurawski, S.M. et al. Definition and spatial location of mouse interleukin-2 residues that interact with its heterotrimeric receptor. EMBO J. 1993; 12:5113-19.
Bazan JF, Haemopoietic receptors and helical cytokines. Immunology Today 1990; 11(10) 350-354.
Bowie Ju, et al. Deciphering the message in protein sequences: tolerance to amino acid substitutions. Science 1990; 247(4948):1306-1310.
Gervais V, et al. NMR investigations of the role of the sugar moiety in glycosylated recombinant human granulocyte-colony-stimulating factor. Eur J Biochem. 1997; 247(1):386-395.
Hershfield MS, et al. Use of site-directed mutagenesis to enhance the epitope-shielding effect of covalent modification of proteins with polyethylene glycol. Proc Natl Acad Sci U S A. 1991; 88(16):7185-7189.
Zink T, et al. Secondary structure of human granulocyte-colony stimulating factor derived from NMR spectroscopy. FEBS Letters 1992; 314(3) 435-439.
Abdel-Meguid et al., Three-dimensional structure of a genetically engineered variant of porcine growth hormone. PNAS 84:6434-6437 (1987).
Abrahmsen L, et al. Engineering subtilisin and its substrates for efficient ligation of peptide bonds in aqueous solution. Biochemistry 30(17):4151-4159 (1991).
Carter et al, Protein crystallization using incomplete factorial experiments. J. Biol. Chem. 254:12219-12223 (1979).
Carter et al., Statistical design of experiments for protein crystal growth. J. Cryst. Growth 90: 60-73 (1988).
Cox et al., Experiments with automated protein crystallization. J. Appl. Crystallogr. 20: 366-373 (1987).
Cox et al., An investigation of protein crystallization parameters. J. Cryst. Growth 90: 318-324 (1988).
Cunningham et al., High-resolution epitope mapping of hGH-receptor interactions by alanine-scanning mutagenesis. Science 244:1081-1084 (1989).
De Vos et al., Human growth hormone and extracellular domain of its receptor: crystal structure of the complex. Science 255: 305-312 (1992).
Diederichs et al., Novel fold and putative receptor binding site of granulocyte-macrophage colony-stimulating factor. Science 254:1779-1782 (1991).
Feng et al., Circular permutation of granulocyte colony-stimulating factor. Biochemistry 38(14):4553-4563 (1999).
Gabrilove, J. Introduction and overview of hematopoietic growth factors. Seminars in Hematology 26:(2, Suppl 2) 1-14 (1989).
Huse et al., Generation of a large combinatorial library of the immunoglobulin repertoire in phage lambda. Science 246:1275-1281 (1989).
Ishikawa et al., The substitution of cysteine 17 of recombinant human G-CSF with alanine greatly enhanced its stability. Cell Structure and Function, 17: 61-65 (1992).
Jancarik et al., Sparse matrix sampling: a screening method for crystallization of proteins. J. Appl. Crystallogr. 24: 409 (1991).
Jones et al., Growth factors in haemopoiesis. Bailliere's Clinical Hematology 2 (1): 83-111 (1989).
Kuga et al., Mutagenesis of human granulocyte colony stimulating factor. Biochem. Biophy. Res. Comm 159:103-111 (1989).
Layton et al., Identification of a functional domain of human granulocyte colony-stimulating factor using neutralizing monoclonal antibodies. JBC 266: 23815-23823 (1991).

Layton et al., Interaction of G-CSF with its receptor: dissociation of biological activity and receptor binding. J. of Cell. Biochem. Suppl. 17B:78, Abstract E225 (1993).
Li, et al., Structure-function analysis of the C-terminal segment of human interleukin-6. J. Biol. Chem. 268(30) 22377-22384 (1993).
Lieshke et al., Granulocyte colony-stimulating factor and granulocyte macrophage colony-stimulating factor (Parts 1 and 2). N. Engl. J. Med. 327: 28-34 and 99-106 (1992).
Lovejoy et al., Crystal sturcture of canine and bovine granulocyte-colony stimulating factor (G-CSF). J. Mol. Biol. 234:640-653 (1993).
Lu et al., Disulfide and secondary structures of recombinant human granulocyte colony stimulating factor. Arch. Biochem. Biophys. 268: 81-92 (1989).
McKay, D.B. Response to technical comment. Science 257: 412-413 (1992).
McWherter et al., Circular permutation of the granulocyte colony-stimulating factor receptor agonist domain of myelopoietin. Biochemistry 38 (14): 4564-4571 (1999).
Moore et al., Synergy of interleukin 1 and granulocyte colony-stimulating factor: in vivo stimulation of stem-cell recovery and hematopoietic regeneration following 5-fluorouracil treatment of mice. Proc. Natl. Acad. Sci. USA 84:7134-7138 (1987).
Nagata et al., The chromosomal gene structure and two mRNAs for human granulocyte colony-stimulating factor. EMBO J. 5: 575-581 (1986).
Nagahara et al., Crystallization and preliminary diffraction studies of recombinant human granulocyte-stimulating factor (KW2228). J. Mol. Biol. 214: 25-26 (1990).
Nicola et al., Separation of functionally distinct granulocyte-macrophage colony-stimulating factors. Blood 54: 614-627 (1979).
Nicola, N.A. Hematopoietic cell growth factors and their receptors. Annu. Rev. Biochem. 58: 45-77 (1989).
Pandit et al., Three-dimensional structure of dimeric human recombinant macrophage colony-stimulating factor. Science 258: 1358-1362 (1992).
Parry et al., Conformational homologies among cytokines: interleukins and colony stimulating factors. J. Molecular Recognition 8: 107-110 (1988).
Powers et al., Three-dimensional solution structure of human interleukin-4 by multidimensional heteronuclear magnetic resonance spectroscopy. Science 256: 1673-1677 (1992).
Rastetter, Enzyme engineering: applications and promise. Trends in Biotechnology, 1(3) 80-84 (1983).
Senda et al., Three-dimensional crystal structure of recombinant murine interferon-beta. EMBO J. 11: 3193-3201 (1992).
Smith et al., Human interleukin 4. The solution structure of a four-helix bundle protein. J. Mol. Biol. 224: 899-904 (1992).
Tsuchiya et al. Isolation and characterization of the cDNA for murine granulocyte colony-stimulating factor. Proc Natl Acad Sci USA. 83(20):7633-7637 (1986).
Weber et al., Physical principles of protein crystallization. In: Eisenberg (ed.), Advances in Protein Chemistry 41:1-33 (1991).
Wells et al., Additivity of mutational effects in proteins. Biochemistry 29(37): 8509-8517 (1990).
Welte et al., Purification and biochemical characterization of human pluripotent hematopoietic colony-stimulating factor. Proc. Natl. Acad. Sci. USA 82:1526-1530 (1985).
Bowie, James et al., "Identifying determinants of folding and activity for a protein of unknown structure," PNAS 86:2151-56 (1989).
Cunningham, Brian C., et al., "Receptor and antibody epitopes in human growth hormone identified by homolog-scanning mutagenesis," Science 243:1330-1336 (1989).
Gaertner, Hubert, "Construction of protein analogues by site-specific condensation of unprotected fragments," Bioconjugate Chem. 3:262 (1992).
Kolvenbach et al., "Characterization of two fluorescent tryptophans in recombinant human granulocyte-colony stimulating factor: comparison of native sequence protein and tryptophan-deficient mutants," J. Protein Chemistry 12 (2) 229-236 (1993).
Lim, Wendell et al., "Alternative packing arrangements in the hydrophobic core of the lambda repressor," Nature 339:31-36 (1989).

Lu, Hsieng S. et al., Folding and oxidation of recombiant human granulocyte colony stimulating factor produced in *escherichia coli*, J. Biol. Chem., 267(13):8770-8777 (1992).

Tanaka, Hideji et al., "Pharmacokinetics of recombinant human granulocyte colony-stimulating factor conjugated to polyethylene glycol in rats," Cancer Res., 51:3710-3714 (1991).

Brunger, Axel T. et al., "Crystallography & NMR system: a new software suite for macromolecular structure determination," Acta Cryst D54:905-921 (1998).

Cregut, David et al., "Molecular dynamics as a tool to detect protein foldability. A mutant of domain B1 of protein G with non-native secondary structure propensities," Protein Science 8:271-282 (1999).

Eisenberg, David et al., "The helical hydrophobic moment: a measure of the amphiphilicity of a helix," Nature 299:371-378 (1982) 9.

Emsley, Paul et al., "Coot: model-building tools for molecular graphics," Acta Cryst. D60:2126-2132 (2004).

Hill, Christopher P. et al., "The structure of granulocyte-colony-stimulating factor and its relationship to other growth factors," PNAS 90:5167-5171 (1993).

Kabsch, Wolfgang et al., "Dictionary of protein secondary structure: pattern recognition of hydrogen-bonded and geometrical features," Biopolymers 22:2577-2637 (1983).

Kleywegt, Gerard J., "Use of non-crystallographic symmetry in protein structure refinement," Acta Cryst. D52:842-857 (1996).

Lau, Kit Fun et al., "Theory for protein mutability and biogenesis," PNAS 87:638-642 (1990).

Manavalan, Parthasarathy et al., "Sequence and structural relationships in the cytokine family," Journal of Protein Chemistry 11(3):321-331 (1992).

O'Shea, Erin K. et al., "X-ray structure of GCN4 leucine Zipper, a two-stranded, parallel coiled coil," Science 254;539-544 (1991).

Ropson, Ira J. et al., "Properties and crystal structure of a beta-barrel folding mutant," Biophysical Journal 78:1551-1560 (2000).

Schiffer et al., "Use of helical wheels to represent the structures of proteins and to identify segments with helical potential," Biophysical Journal 7:121:135 (1967).

Shih, H. et al., "Structure of proteins with single-site mutations: a minimum perturbation approach," PNAS 82:1697-1700 (1985).

Tallquist, Michelle D. et al., "Degenerate recognition of alloantigenic peptides on a positive-selecting class I molecule," The Journal of Immunology 160:802-809 (1998).

Tsuji, Takashi et al., "Design and synthesis of the pseudo-EF hand in calbindin D9k: effect of amino acid substitutions in the a-helical regions," Proteins: Structure, Function and Genetics 9:12-22 (1991).

Zidovetzki, Raphael et al., "Transmembrane domains in the functions of Fc receptors," Biophysical Chemistry 100:555-575 (2003).

\* cited by examiner

SEQUENCE LISTING

```
<160> NUMBER OF SEQ ID NOS: 15

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45
```

```
Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
             100                 105                 110

Phe Ala Thr Thr Ile Trp Gln Gln Met Glu Glu Leu Gly Met Ala Pro
         115                 120                 125

Ala Leu Gln Pro Thr Gln Gly Ala Met Pro Ala Phe Ala Ser Ala Phe
     130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 525
<212> TYPE: DNA
<213> ORGANISM: Artificial Sequence
<220> FEATURE:
<221> NAME/KEY: misc_feature
<223> OTHER INFORMATION: DNA sequence encoding hG-CSF, with codon
      usage for E. coli

<400> SEQUENCE: 2
acccctctgg gcccggccag cagtctgcct cagagttttt tactgaaatg cttagaacag     60
gtgcgtaaaa tccagggcga tggcgcggcc ctgcaggaaa actgtgcgc gacctataaa    120 ctgtgccatc ctgaagaact ggtcctgtta ggccatagct taggcatccc gtgggcgcct   180
ctgagtagct gcccgagtca ggccctgcag ctggccggct gcctgagtca gttacatagt   240
ggcttatttt tatatcaggg cttactgcag gcgttagaag gcattagtcc ggaactgggc   300
ccgaccctgg ataccttaca gttagatgtc gcggattttg ccaccaccat ttggcagcag   360
atggaagaat taggcatggc gcctgcgtta cagcctaccc agggcgccat gcctgcgttt   420
gcgagtgcgt ttcagcgtcg cgccggcggc gtgttagtgg ccagccatct gcagagcttt   480
ctggaagtga gttatcgtgt gttacgccat ctggcccagc cttaa                   525

<210> SEQ ID NO 3
<211> LENGTH: 21
<212> TYPE: PRT
<213> ORGANISM: Escherichia coli

<400> SEQUENCE: 3

Met Lys Lys Thr Ala Ile Ala Ile Ala Val Ala Leu Ala Gly Phe Ala
 1               5                  10                  15

Thr Val Ala Gln Ala
             20

<210> SEQ ID NO 4
<211> LENGTH: 63
<212> TYPE: DNA
<213> ORGANISM: Artificial Sequence
<220> FEATURE:
<221> NAME/KEY: misc_feature
<223> OTHER INFORMATION: DNA sequence encoding the OmpA signal sequence

<400> SEQUENCE: 4
```

```
atgaaaaaga cagctatcgc gattgcagtg gcactggctg gtttcgctac cgtagcgcag    60
gcc                                                                  63
```

<210> SEQ ID NO 5
<211> LENGTH: 15
<212> TYPE: PRT
<213> ORGANISM: Artificial Sequence
<220> FEATURE:
<221> NAME/KEY: PEPTIDE
<222> LOCATION: (1)..(15)
<223> OTHER INFORMATION: Synthetic tag

<400> SEQUENCE: 5

Met Lys His Gln His Gln His Gln His Gln His Gln His Gln Gln
1               5                   10                  15

<210> SEQ ID NO 6
<211> LENGTH: 45
<212> TYPE: DNA
<213> ORGANISM: Artificial Sequence
<220> FEATURE:
<221> NAME/KEY: misc_feature
<223> OTHER INFORMATION: DNA encoding the tag of SEQ ID NO:5

<400> SEQUENCE: 6

```
atgaaacacc aacaccaaca tcaacatcaa catcaacatc aacag                    45
```

<210> SEQ ID NO 7
<211> LENGTH: 30
<212> TYPE: PRT
<213> ORGANISM: Homo sapiens
<220> FEATURE:
<221> NAME/KEY: SIGNAL
<222> LOCATION: (1)..(30)
<223> OTHER INFORMATION:

<400> SEQUENCE: 7

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala
            20                  25                  30

<210> SEQ ID NO 8
<211> LENGTH: 615
<212> TYPE: DNA
<213> ORGANISM: Artificial Sequence
<220> FEATURE:
<221> NAME/KEY: misc_feature
<223> OTHER INFORMATION: Sequence encoding hG-CSF with signal peptide
      of SEQ ID NO:7

<400> SEQUENCE: 8

```
atggccggcc ctgccacaca gtcccccatg aagctgatgg ccctgcagct gctgctgtgg    60
cactccgccc tgtggacagt gcaggaggcc acccctctgg ccccgccag ctccctgcct    120 cagtccttcc tgctgaagtg cctggagcag gtgagaaaga tccagggcga cggcgccgcc    180
ctgcaggaga agctgtgcgc cacatacaag ctgtgccacc tgaggagct ggtgctgctg    240 ggccacagcc tgggcatccc ctgggccct ctgtccagct gccctccca ggccctgcag    300 ctggccggct gcctgtccca gctgcactcc ggcctgttcc tgtaccaggg cctgctgcag    360
gccctggagg gcatctcccc cgagctgggc cccacactgg atacccctgca gctggacgtg    420 gccgatttcg ccaccacaat ctggcagcag atggaggagc tgggcatggc ccctgccctg    480
```
cagcctaccc agggcgccat gcctgccttt gcctccgcct ttcagagacg ggccggcggc    540
gtgctggtgg ccagccacct gcagagcttt ctggaggtgt cctacagagt gctgcggcac    600
ctggcccagc cttga                                                      615

<210> SEQ ID NO 9
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Synthetic tag

<400> SEQUENCE: 9

His His His His His His
1               5

<210> SEQ ID NO 10
<211> LENGTH: 8
<212> TYPE: PRT
<213> ORGANISM: Artificial Sequence
<220> FEATURE:
<221> NAME/KEY: PEPTIDE
<222> LOCATION: (1)..(8)
<223> OTHER INFORMATION: Synthetic tag

<400> SEQUENCE: 10

Met Lys His His His His His His
1               5

<210> SEQ ID NO 11
<211> LENGTH: 10
<212> TYPE: PRT
<213> ORGANISM: Artificial Sequence
<220> FEATURE:
<221> NAME/KEY: PEPTIDE
<222> LOCATION: (1)..(10)
<223> OTHER INFORMATION: Synthetic tag

<400> SEQUENCE: 11

Met Lys His His Ala His His Gln His His
1               5                   10

<210> SEQ ID NO 12
<211> LENGTH: 14
<212> TYPE: PRT
<213> ORGANISM: Artificial Sequence
<220> FEATURE:
<221> NAME/KEY: PEPTIDE
<222> LOCATION: (1)..(14)
<223> OTHER INFORMATION: Synthetic tag

<400> SEQUENCE: 12

Met Lys His Gln His Gln His Gln His Gln His Gln His Gln
1               5                   10

<210> SEQ ID NO 13
<211> LENGTH: 10
<212> TYPE: PRT
<213> ORGANISM: Artificial Sequence
<220> FEATURE:
<221> NAME/KEY: PEPTIDE
<222> LOCATION: (1)..(10)
<223> OTHER INFORMATION: Synthetic tag

<400> SEQUENCE: 13

Glu Gln Lys Leu Ile Ser Glu Glu Asp Leu

```
<210> SEQ ID NO 14
<211> LENGTH: 8
<212> TYPE: PRT
<213> ORGANISM: Artificial Sequence
<220> FEATURE:
<221> NAME/KEY: PEPTIDE
<222> LOCATION: (1)..(8)
<223> OTHER INFORMATION: Synthetic tag

<400> SEQUENCE: 14

Asp Tyr Lys Asp Asp Asp Asp Lys
1               5

<210> SEQ ID NO 15
<211> LENGTH: 9
<212> TYPE: PRT
<213> ORGANISM: Artificial Sequence
<220> FEATURE:
<221> NAME/KEY: PEPTIDE
<222> LOCATION: (1)..(9)
<223> OTHER INFORMATION: Synthetic tag

<400> SEQUENCE: 15

Tyr Pro Tyr Asp Val Pro Asp Tyr Ala
1               5
```

G-CSF CONJUGATES

CROSS-REFERENCE TO RELATED APPLICATIONS

This application is a division of U.S. application Ser. No. 11/004,461, filed Dec. 3, 2004 now abandoned, which is a continuation of U.S. application Ser. No. 10/192,294, filed Jul. 10, 2002, now U.S. Pat. No. 6,831,158, which is a continuation-in-part of U.S. application Ser. No. 09/904,196 filed Jul. 11, 2001, now U.S. Pat. No. 6,555,660, which is a continuation-in-part of U.S. application Ser. No. 09/760,008, filed Jan. 10, 2001, now U.S. Pat. No. 6,646,110, which claims the benefit of provisional applications U.S. Ser. No. 60/176,376, filed Jan. 14, 2000, U.S. Ser. No. 60/189,506, filed Mar. 15, 2000, and U.S. Ser. No. 60/215,644, filed Jun. 30, 2000, pursuant 35 U.S.C. § 119(e). This application also claims priority to Danish Patent Application No. PA 2002 00447, filed Mar. 22, 2002, Danish Patent Application No. PA 2002 00708, filed May 8, 2002, Danish Patent Application No. PA 2000 00094, filed Jan. 10, 2000, Danish Patent Application No. PA 2000 00341, filed Mar. 2, 2000, and Danish Patent Application No. PA 2000 00943, filed Jun. 16, 2000, pursuant 35 U.S.C. § 119(a). The disclosure of each application listed above is incorporated herein in its entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to new polypeptides exhibiting granulocyte colony-stimulating factor (G-CSF) activity, to conjugates between a polypeptide exhibiting G-CSF activity and a non-polypeptide moiety, to methods for preparing such polypeptides or conjugates and the use of such polypeptides or conjugates in therapy, in particular for the treatment of neutropenia or leukopenia.

BACKGROUND OF THE INVENTION

The process by which white blood cells grow, divide and differentiate in the bone marrow is called hematopoiesis (Dexter and Spooncer, Ann. Rev. Cell. Biol., 3:423, 1987). Each of the blood cell types arises from pluripotent stem cells. There are generally three classes of blood cells produced in vivo: red blood cells (erythrocytes), platelets and white blood cells (leukocytes), the majority of the latter being involved in host immune defense. Proliferation and differentiation of hematopoietic precursor cells are regulated by a family of cytokines, including colony-stimulating factors (CSF's) such as G-CSF and interleukins (Arai et al., Ann. Rev. Biochem., 59:783-836, 1990). The principal biological effect of G-CSF in vivo is to stimulate the growth and development of certain white blood cells known as neutrophilic granulocytes or neutrophils (Welte et al., PNAS-USA 82:1526-1530, 1985, Souza et al., Science, 232:61-65, 1986). When released into the blood stream, neutrophilic granulocytes function to fight bacterial and other infection.

The amino acid sequence of human G-CSF (hG-CSF) was reported by Nagata et al. Nature 319:415-418, 1986. hG-CSF is a monomeric protein that dimerizes the G-CSF receptor by formation of a 2:2 complex of 2 G-CSF molecules and 2 receptors (Horan et al. (1996), Biochemistry 35(15): 4886-96). Aritomi et al. Nature 401:713-717, 1999 have described the X-ray structure of a complex between hG-CSF and the BN-BC domains of the G-CSF receptor. They identify the following hG-CSF residues as being part of the receptor binding interfaces: G4, P5, A6, S7, S8, L9, P10, Q1, S12, L15, K16, E19, Q20, L108, D109, D12, T115, T116, Q119, E122, E123, and L124. Expression of rhG-CSF in Escherichia coli, Saccharomyces cerevisiae and mammalian cells has been reported (Souza et al., Science 232:61-65, 1986, Nagata et al., Nature 319: 415-418, 1986, Robinson and Wittrup, Biotechnol. Prog. 11:171-177, 1985).

Leukopenia (a reduced level of white blood cells) and neutropenia (a reduced level of neutrophils) are disorders that result in an increased susceptibility to various types of infections. Neutropenia can be chronic, e.g. in patients infected with HIV, or acute, e.g. in cancer patients undergoing chemotherapy or radiation therapy. For patients with severe neutropenia, e.g. as a result of chemotherapy, even relatively minor infections can be serious and even life-threatening. Recombinant human G-CSF (rhG-CSF) is generally used for treating various forms of leukopenia/neutropenia. Thus, commercial preparations of rhG-CSF are available under the names filgrastim (Gran® and Neupogen®), lenograstim (Neutrogin® and Granocyte®) and nartograstim (Neu-up®). Gran® and Neupogen® are non-glycosylated and produced in recombinant E. coli cells. Neutrogin® and Granocyte® are glycosylated and produced in recombinant CHO cells and Neu-up® is non-glycosylated with five amino acids substituted at the N-terminal region of intact rhG-CSF produced in recombinant E. coli cells.

Various protein-engineered variants of hG-CSF have been reported (e.g. U.S. Pat. Nos. 5,581,476, 5,214,132, 5,362,853, and 4,904,584 and Riedhaar-Olson et al. Biochemistry 35: 9034-9041, 1996). Modification of hG-CSF and other polypeptides so as to introduce at least one additional carbohydrate chain as compared to the native polypeptide has been suggested (U.S. Pat. No. 5,218,092). It is stated that the amino acid sequence of the polypeptide may be modified by amino acid substitution, amino acid deletion or amino acid insertion so as to effect addition of an additional carbohydrate chain. In addition, polymer modifications of native hG-CSF, including attachment of PEG groups, have been reported (Satake-Ishikawa et al., Cell Structure and Function 17:157-160, 1992, U.S. Pat. No. 5,824,778, U.S. Pat. No. 5,824,784, WO 96/11953, WO 95/21629, WO 94/20069).

Bowen et al., Experimental Hematology 27 (1999), 425-432 disclose a study of the relationship between molecule mass and duration of activity of PEG-conjugated G-CSF mutein. An apparent inverse correlation was suggested between molecular weight of the PEG moieties conjugated to the protein and in vitro activity, whereas in vivo activities increased with increasing molecular weight. It is speculated that a lower affinity of the conjugates act to increase the half-life, because receptor-mediated endocytosis is an important mechanism regulating levels of hematopoietic growth factors.

The commercially available rhG-CSF has a short-term pharmacological effect and must therefore be administered once a day for the duration of the leukopenic state. A molecule with a longer circulation half-life would decrease the number of administrations necessary to alleviate the leukopenia and prevent consequent infections. Another, more significant problem with currently available rG-CSF products is that patients become neutropenic after chemotherapy even after administration of G-CSF. For these patients, it is important to be able to reduce the duration and degree of the neutropenic state as much as possible in order to minimize the risk of serious infections. A further problem is the occurrence of dose-dependent bone pain. Since bone pain is experienced by patients as a significant side effect of treatment with rG-CSF, it would be desirable to provide a rG-CSF product that does not cause bone pain, either by means of a product that inherently does not have this effect or that is effective in a sufficiently small dose that no bone pain is caused. Thus, there is clearly a need for improved recombinant G-CSF-like molecules.

With respect to the half-life, one way to increase the circulation half-life of a protein is to ensure that clearance of the protein, in particular via renal clearance and receptor-mediated clearance, is reduced. This may be achieved by conjugating the protein to a chemical moiety which is capable of increasing the apparent size, thereby reducing renal clearance and increasing the in vivo half-life. Furthermore, attachment of a chemical moiety to the protein may effectively block proteolytic enzymes from physical contact with the protein, thus preventing degradation by non-specific proteolysis. Polyethylene glycol (PEG) is one such chemical moiety that has been used in the preparation of therapeutic protein products. Recently, G-CSF molecule modified with a single, N-terminally linked 20 kDa PEG group (Neulasta™) was approved for sale in the United States. This PEGylated G-CSF molecule has been shown to have an increased half-life compared to non-PEGylated G-CSF and thus may be administered less frequently than current G-CSF products, but it does not reduce the duration of neutropenia significantly compared to non-PEGylated G-CSF. Thus, there is still substantial room for improvement of the known G-CSF molecules.

A need therefore still exists for providing novel molecules exhibiting G-CSF activity that are useful in the treatment of leukopenia/neutropenia, and which have are improved in terms of e.g. an increased half-life and in particular a reduction in the duration of neutropenia. The present invention relates to such molecules.

BRIEF DISCLOSURE OF THE INVENTION

The present invention relates to specific conjugates comprising a polypeptide exhibiting G-CSF activity and a non-polypeptide moiety, methods for their preparation and their use in medical treatment and in the preparation of pharmaceuticals. Accordingly, in a first aspect the invention relates to various specific conjugates comprising a polypeptide exhibiting G-CSF activity and having an amino acid sequence that differs from the known amino acid sequence of human G-CSF as shown in SEQ ID NO:1 in at least one specified altered amino acid residue comprising an attachment group for a non-polypeptide moiety, and having at least one non-polypeptide moiety attached to an attachment group of the polypeptide. These conjugates have a substantially reduced in vitro bioactivity compared to that of non-conjugated hG-CSF, which surprisingly has been shown to result in a more rapid neutrophil recovery. The conjugate of the present invention thus has one or more improved properties as compared to commercially available rhG-CSF, including increased stimulation of neutrophils, increased functional in vivo half-life, increased serum half-life, reduced side effects, reduced immunogenicity and/or increased bioavailability. Consequently, medical treatment with a conjugate of the invention offers a number of advantages over the currently available G-CSF compounds.

In a further aspect the invention relates to polypeptides exhibiting G-CSF activity and which form part of a conjugate of the invention. The polypeptides of the invention are contemplated to be useful as such for therapeutic, diagnostic or other purposes, but find particular interest as intermediate products for the preparation of a conjugate of the invention.

In a further aspect the invention relates to a polypeptide conjugate comprising a polypeptide exhibiting G-CSF activity, which comprises an amino acid sequence that differs from the amino acid sequence of hG-CSF (with the amino acid sequence shown in SEQ ID NO:1) in at least one amino acid residue selected from an introduced or removed amino acid residue comprising an attachment group for a non-polypeptide moiety, and a sufficient number or type of non-polypeptide moieties to provide the conjugate with an increased half-life and/or a more rapid neutrophil recovery compared to known recombinant G-CSF products.

In a particular aspect the invention relates to a polypeptide conjugate exhibiting G-CSF activity, comprising a polypeptide having the substitutions K16R, K34R, K40R, T105K, and S159K, and optionally a substitution in position H170, e.g. to R, K or Q, relative to the amino acid sequence of hG-CSF shown in SEQ ID NO:1, or in a corresponding position relative to an amino acid sequence having at least 80% sequence identity with SEQ ID NO:1, and having 2-6, typically 3-6 polyethylene glycol moieties with a molecular weight of about 1000-10,000 Da attached to one or more attachment groups of the polypeptide. Where these substitutions are relative to a sequence with at least about 80% sequence identity with SEQ ID NO:1, the degree of sequence identity is typically at least about 90% or 95%, such as at least about 96%, 97%, 98% or 99%.

In still further aspects the invention relates to methods for preparing a conjugate of the invention, including nucleotide sequences encoding a polypeptide of the invention, expression vectors comprising such a nucleotide sequence, and host cells comprising such a nucleotide sequence or expression vector.

In final aspects the invention relates to a composition comprising a conjugate or polypeptide of the invention, a method for preparing a pharmaceutical composition, use of a conjugate or composition of the invention as a pharmaceutical, and a method of treating a mammal with such composition. In particular, the polypeptide, conjugate or composition of the invention may be used to prevent infection in cancer patients undergoing certain types of radiation therapy, chemotherapy, and bone marrow transplantations, to mobilize progenitor cells for collection in peripheral blood progenitor cell transplantations, for treatment of severe chronic or relative leukopenia, irrespective of cause, and to support treatment of patients with acute myeloid leukemia. Additionally, the polypeptide, conjugate or composition of the invention may be used for treatment of AIDS or other immunodeficiency diseases as well as bacterial infections.

DETAILED DISCLOSURE OF THE INVENTION

Definitions

In the context of the present application and invention the following definitions apply:

The term "conjugate" is intended to indicate a heterogeneous molecule formed by the covalent attachment of one or more polypeptides, typically a single polypeptide, to one or more non-polypeptide moieties such as polymer molecules, lipophilic compounds, carbohydrate moieties or organic derivatizing agents. The term covalent attachment means that the polypeptide and the non-polypeptide moiety are either directly covalently joined to one another, or else are indirectly covalently joined to one another through an intervening moiety or moieties, such as a bridge, spacer, or linkage moiety or moieties. Preferably, the conjugate is soluble at relevant concentrations and conditions, i.e. soluble in physiological fluids such as blood. The term "non-conjugated polypeptide" may be used about the polypeptide part of the conjugate.

The term "polypeptide" may be used interchangeably herein with the term "protein".

The "polymer molecule" is a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is intended to cover carbohydrate molecules, although, normally, the term is not intended to cover the type of carbohydrate molecule which is attached to the polypeptide by in vivo N- or O-glycosylation (as further described below), since such molecule is referred to herein as "an oligosaccharide moiety". Except where the number of polymer molecule(s) is expressly indicated every reference to "a polymer", "a polymer molecule", "the polymer" or "the polymer molecule" contained in a polypeptide of the invention or otherwise used in the present invention shall be a reference to one or more polymer molecule(s).

The term "attachment group" is intended to indicate an amino acid residue group of the polypeptide capable of coupling to the relevant non-polypeptide moiety. For instance, for polymer conjugation, in particular to PEG, a frequently used attachment group is the $\epsilon$-amino group of lysine or the N-terminal amino group. Other polymer attachment groups include a free carboxylic acid group (e.g. that of the C-terminal amino acid residue or of an aspartic acid or glutamic acid residue), suitably activated carbonyl groups, oxidized carbohydrate moieties and mercapto groups. Useful attachment groups and their matching non-peptide moieties are apparent from the table below.

| Attachment group | Amino acid | Examples of non-peptide moiety | Conjugation method/-Activated PEG | Reference |
|---|---|---|---|---|
| —NH$_2$ | N-terminal, Lys, His, Arg | Polymer, e.g. PEG, with amide or imine group | mPEG-SPA Tresylated mPEG | Shearwater Corp. Delgado et al., critical reviews in Therapeutic Drug Carrier Systems 9(3, 4): 249-304 (1992) |
| —COOH | C-term, Asp, Glu | Polymer, e.g. PEG, with ester or amide group | mPEG-Hz | Shearwater Corp. |
| | | Oligosaccharide moiety | In vitro coupling | |
| —SH | Cys | Polymer, e.g. PEG, with disulfide, maleimide or vinyl sulfone group | PEG-vinylsulphone PEG-maleimide | Shearwater Corp. Delgado et al., critical reviews in Therapeutic Drug Carrier Systems 9(3, 4): 249-304 (1992) |
| | | Oligosaccharide moiety | In vitro coupling | |
| —OH | Ser, Thr, —OH, Lys | Oligosaccharide moiety PEG with ester, ether, carbamate, carbonate | In vivo O-linked glycosylation | |
| —CONH$_2$ | Asn as part of an N-glycosylation site | Oligosaccharide moiety Polymer, e.g. PEG | In vivo N-glycosylation | |
| Aromatic residue | Phe, Tyr, Trp | Oligosaccharide moiety | In vitro coupling | |
| —CONH$_2$ | Gln | Oligosaccharide moiety | In vitro coupling | Yan and Wold, Biochemistry, 1984, Jul 31; 23(16): 3759-65 |
| Aldehyde Ketone | Oxidized oligosaccharide | Polymer, e.g. PEG, PEG-hydrazide | PEGylation | Andresz et al., 1978, Makromol. Chem. 179: 301, WO 92/16555, WO 00/23114 |
| Guanidino | Arg | Oligosaccharide moiety | In vitro coupling | Lundblad and Noyes, Chemical Reagents for Protein Modification, CRC Press Inc., Florida, USA |
| Imidazole ring | His | Oligosaccharide moiety | In vitro coupling | As for guanidine |

For in vivo N-glycosylation, the term "attachment group" is used in an unconventional way to indicate the amino acid residues constituting an N-glycosylation site (with the sequence N-X'-S/T/C-X", wherein X' is any amino acid residue except proline, X" any amino acid residue which may or may not be identical to X' and which preferably is different from proline, N is asparagine, and S/T/C is either serine, threonine or cysteine, preferably serine or threonine, and most preferably threonine). Although the asparagine residue of the N-glycosylation site is where the oligosaccharide moiety is attached during glycosylation, such attachment cannot be achieved unless the other amino acid residues of the N-glycosylation site are present. Accordingly, when the non-peptide moiety is an oligosaccharide moiety and the conjugation is to be achieved by N-glycosylation, the term "amino acid residue comprising an attachment group for the non-peptide moiety" as used in connection with alterations of the amino acid sequence of the polypeptide of interest is to be understood as meaning that one or more amino acid residues constituting an N-glycosylation site are to be altered in such a manner that either a functional N-glycosylation site is introduced into the amino acid sequence or removed from said sequence.

In the present application, amino acid names and atom names (e.g. CA, CB, NZ, N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), *Eur. J. Biochem.*, 138, 9-37 (1984) together with their corrections in *Eur. J. Biochem.*, 152, 1 (1985). The term "amino acid residue" is intended to indicate any naturally or non-naturally occurring amino acid residue, in particular an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terminology used for identifying amino acid positions/substitutions is illustrated as follows: F13 indicates position number 13 occupied by a phenylalanine residue in the reference amino acid sequence. F13K indicates that the phenylalanine residue of position 13 has been substituted with a lysine residue. Unless otherwise indicated, the numbering of amino acid residues made herein is made relative to the amino acid sequence of hG-CSF shown in SEQ ID NO:1. Alternative substitutions are indicated with a "/", e.g. Q67D/E means an amino acid sequence in which glutamine in position 67 is substituted with either aspartic acid or glutamic acid. Multiple substitutions are indicated with a "+", e.g. S53N+G55S/T means an amino acid sequence which comprises a substitution of the serine residue in position 53 with an asparagine residue and a substitution of the glycine residue in position 55 with a serine or a threonine residue.

The term "nucleotide sequence" is intended to indicate a consecutive stretch of two or more nucleotide molecules. The nucleotide sequence may be of genomic, cDNA, RNA, semi-synthetic or synthetic origin, or any combination thereof.

The term "polymerase chain reaction" or "PCR" refers to the well-known method for amplification of a desired nucleotide sequence in vitro using a thermostable DNA polymerase.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "introduce" refers to introduction of an amino acid residue comprising an attachment group for a non-polypeptide moiety, in particular by substitution of an existing amino acid residue, or alternatively by insertion of an additional amino acid residue. The term "remove" refers to removal of an amino acid residue comprising an attachment group for a non-polypeptide moiety, in particular by substitution of the amino acid residue to be removed by another amino acid residue, or alternatively by deletion (without substitution) of the amino acid residue to be removed.

When substitutions are performed in relation to a parent polypeptide, they are preferably "conservative substitutions", in other words substitutions performed within groups of amino acids with similar characteristics, e.g. small amino acids, acidic amino acids, polar amino acids, basic amino acids, hydrophobic amino acids and aromatic amino acids.

Preferred substitutions in the present invention may in particular be chosen from among the conservative substitution groups listed in the table below.

Conservative Substitution Groups:

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

The term "immunogenicity" as used in connection with a given substance is intended to indicate the ability of the substance to induce a response from the immune system. The immune response may be a cell or antibody mediated response (see, e.g., Roitt: Essential Immunology (8$^{th}$ Edition, Blackwell) for further definition of immunogenicity). Normally, reduced antibody reactivity will be an indication of reduced immunogenicity. The reduced immunogenicity may be determined by use of any suitable method known in the art, e.g. in vivo or in vitro.

The term "functional in vivo half-life" is used in its normal meaning, i.e. the time at which 50% of the biological activity of the polypeptide or conjugate is still present in the body/target organ, or the time at which the activity of the polypeptide or conjugate is 50% of the initial value. As an alternative to determining functional in vivo half-life, "serum half-life" may be determined, i.e. the time in which 50% of the polypeptide or conjugate molecules circulate in the plasma or bloodstream prior to being cleared. Alternative terms to serum half-life include "plasma half-life", "circulating half-life", "serum clearance", "plasma clearance" and "clearance half-life". The polypeptide or conjugate is cleared by the action of one or more of the reticuloendothelial systems (RES), kidney, spleen or liver, by receptor-mediated degradation, or by specific or non-specific proteolysis, in particular by the action of receptor-mediated clearance and renal clearance. Normally, clearance depends on size (relative to the cutoff for glomerular filtration), charge, attached carbohydrate chains, and the presence of cellular receptors for the protein. The functionality to be retained is normally selected from proliferative or receptor-binding activity. The functional in vivo half-life and the serum half-life may be determined by any suitable method known in the art as further discussed in the Materials and Methods section below.

The term "increased" as used about the functional in vivo half-life or serum half-life is used to indicate that the relevant half-life of the conjugate or polypeptide is statistically significantly increased relative to that of a reference molecule, such as a non-conjugated hG-CSF (e.g. Neupogen®) as determined under comparable conditions. For instance, the relevant half-life may increased by at least about 25%, such as by at least about 50%, e.g. by at least about 100%, 200%, 500% or 1000%.

The term "renal clearance" is used in its normal meaning to indicate any clearance taking place by the kidneys, e.g. by glomerular filtration, tubular excretion or tubular elimination. Renal clearance depends on physical characteristics of the conjugate, including size (diameter), symmetry, shape/rigidity and charge. Reduced renal clearance may be established by any suitable assay, e.g. an established in vivo assay. Typically, renal clearance is determined by administering a labeled (e.g. radioactive or fluorescent labeled) polypeptide conjugate to a patient and measuring the label activity in urine collected from the patient. Reduced renal clearance is determined relative to a corresponding reference polypeptide, e.g. the corresponding non-conjugated polypeptide, a non-conjugated corresponding wild-type polypeptide or another conjugated polypeptide (such as a conjugated polypeptide not according to the invention), under comparable conditions. Preferably, the renal clearance rate of the conjugate is reduced by at least 50%, preferably by at least 75%, and most preferably by at least 90% compared to a relevant reference polypeptide.

Generally, activation of the receptor is coupled to receptor-mediated clearance (RMC) such that binding of a polypeptide to its receptor without activation does not lead to RMC, while activation of the receptor leads to RMC. The clearance is due to internalization of the receptor-bound polypeptide with subsequent lysosomal degradation. Reduced RMC may be achieved by designing the conjugate so as to be able to bind and activate a sufficient number of receptors to obtain optimal in vivo biological response and avoid activation of more receptors than required for obtaining such response. This may be reflected in reduced in vitro bioactivity and/or increased off-rate. In a preferred embodiment, the conjugates of the invention have a substantially reduced in vitro bioactivity compared to that of non-conjugated hG-CSF.

Typically, reduced in vitro bioactivity reflects reduced efficacy/efficiency and/or reduced potency and may be determined by any suitable method for determining any of these properties. For instance, in vitro bioactivity may be determined in a luciferase based assay ("Primary assay 2"; see Materials and Methods). Another method for determining the in vitro bioactivity is to determine the binding affinity of a conjugate of the invention using the cell-based assay described in the Materials and Methods section ("Secondary assay").

It has been found that a relatively low in vitro bioactivity, compared to the activity of hG-CSF (SEQ ID NO:1), is advantageous in terms of both a long plasma half-life and a high degree of stimulation of neutrophils. Surprisingly, it has been found that administration of G-CSF conjugates of the invention having a low in vitro bioactivity results in a faster neutrophil recovery, i.e. a faster recovery of the neutrophil count to a normal level, than administration of hG-CSF. Since it is critical to be able to reduce the duration of neutropenia as much as possible in patients having a reduced neutrophil level due to e.g. chemotherapy or radiation therapy, this is an important finding. Thus, in a preferred embodiment, the in vitro bioactivity of a conjugate of the invention is in the range of about 2-30%, preferably about 3-25%, of the bioactivity of hG-CSF (where the hG-CSF used as the reference polypeptide has SEQ ID NO:1, optionally with an N-terminal methionine residue; the reference hG-CSF may in particular be Neupogen®, i.e. non-glycosylated Met-hG-CSF) as determined by the luciferase assay described herein, or, alternatively, using the cell-based receptor binding affinity assay ("Secondary assay"). The in vitro bioactivity of the conjugate is thus preferably reduced by at least 70%, such as by at least 75%, e.g. by at least 80% or 85%, as compared to the in vitro bioactivity of hG-CSF, determined under comparable conditions. Expressed differently, the conjugate may have an in vitro bioactivity that is as small as about 2%, typically at least about 3%, such as at least about 4% or 5%, of that of the wild-type polypeptide. For instance, the in vitro bioactivity may be in the range of about 4-20% of that of hG-CSF, determined under comparable conditions. In cases where reduced in vitro bioactivity is desired in order to reduce receptor-mediated clearance, it will be clear that sufficient bioactivity to obtain the desired receptor activation must nevertheless be maintained, which is why the bioactivity should be at least about 2% of that of hG-CSF and preferably slightly higher as explained above.

It has been found that amino acid alterations, in particular substitutions, in the helix regions of G-CSF, i.e. in an amino acid residue selected from amino acid position 11-41 (helix A), 71-95 (helix B), 102-125 (helix C), and 145-170 (helix D) (compared to SEQ ID NO:1), result in a reduced receptor-mediated clearance and thus an increased in vivo half-life when the resulting polypeptides are conjugated to polyethylene glycol. In addition to a longer half-life, it has surprisingly been found that administration of such polypeptide conjugates is able to stimulate production of white blood cells and neutrophils to the same degree as, or even better than, administration of the commercially available G-CSF products Neupogen® and Neulasta™. G-CSF conjugates having a reduced in vitro bioactivity may thus be prepared by altering, typically by substitution, one or more amino acid residues in a helix region of G-CSF, and by conjugating the resulting polypeptide to one or more non-polypeptide moieties such as polyethylene glycol.

Preferably, the off-rate between the polypeptide conjugate and its receptor is increased by a magnitude resulting in the polypeptide conjugate being released from its receptor before any substantial internalization of the receptor-ligand complex has taken place. The receptor-polypeptide binding affinity may be determined as described in the Materials and Methods section herein. The off-rate may be determined using the Biacore® technology as described in the Materials and Methods section. The in vitro RMC may be determined by labeling (e.g. radioactive or fluorescent labeling) the polypeptide conjugate, stimulating cells comprising the receptor for the polypeptide, washing the cells, and measuring label activity. Alternatively, the conjugate may be exposed to cells expressing the relevant receptor. After an appropriate incubation time the supernatant is removed and transferred to a well containing similar cells. The biological response of these cells to the supernatant is determined relative to a non-conjugated polypeptide or another reference polypeptide, and this is a measure of the extent of the reduced RMC.

Normally, reduced in vitro bioactivity of the conjugate is obtained as a consequence of its modification by a non-polypeptide moiety. However, in order to further reduce in vitro bioactivity or for other reasons it may be of interest to modify the polypeptide part of the conjugate further. For instance, in one embodiment at least one amino acid residue located at or near a receptor binding site of the polypeptide may be substituted with another amino acid residue as compared to the corresponding wild-type polypeptide so as to obtain reduced in vitro bioactivity. The amino acid residue to be introduced by substitution may be any amino acid residue capable of reducing in vitro bioactivity of the conjugate. Conveniently, the introduced amino acid residue comprises an attachment group for the non-polypeptide moiety as defined herein. In particular, when the non-polypeptide moiety is a polymer molecule such as PEG molecule, the amino acid residue to be introduced may be a lysine residue.

The term "exhibiting G-CSF activity" is intended to indicate that the polypeptide or conjugate has one or more of the functions of native G-CSF, in particular hG-CSF with the amino acid sequence shown in SEQ ID NO:1, including the capability to bind to a G-CSF receptor (Fukunaga et al., J. Bio. Chem, 265:14008, 1990). The G-CSF activity is conveniently assayed using the primary assay described in the Materials and Methods section hereinafter. The polypeptide "exhibiting" G-CSF activity is considered to have such activity when it displays a measurable function, e.g. a measurable proliferative activity or a receptor binding activity (e.g. as determined by the primary assay described in the Materials and Methods section). The polypeptide exhibiting G-CSF activity may also be termed "G-CSF molecule" herein for the sake of simplicity, even though such polypeptides are in fact variants of G-CSF.

The term "parent G-CSF" or "parent polypeptide" is intended to indicate the molecule to be modified in accordance with the present invention. The parent G-CSF is normally hG-CSF or a variant thereof. A "variant" is a polypeptide which differs in one or more amino acid residues from a parent polypeptide, normally in 1, 2, 3, 4, 5, 6, 7, 8, 9, 10, 11, 12, 13, 14 or 15 amino acid residues. Examples of rhG-CSF include filgrastim (Gran® and Neupogen®), lenograstim (Neutrogin® and Granocyte®) and nartograstim (Neu-up®).

Conjugate of the Invention

As stated above, in a first aspect the invention relates to a conjugate comprising a polypeptide exhibiting G-CSF activity, which comprises an amino acid sequence that differs from the amino acid sequence of SEQ ID NO:1 in at least one amino acid residue selected from specified introduced or removed amino acid residues comprising an attachment group for a non-polypeptide moiety, and at least one non-polypeptide moiety attached to an attachment group of the polypeptide. The amino acid residues to be introduced and/or removed are described in further detail in the following sections. It will be understood that the conjugate itself also exhibits G-CSF activity.

By removing and/or introducing an amino acid residue comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the G-CSF molecule and to ensure that only the attachment groups intended to be conjugated are present in the molecule) and thereby obtain a new conjugate molecule which has G-CSF activity and in addition one or more improved properties as compared to G-CSF molecules available today.

While the polypeptide may be of any origin, in particular mammalian origin, it is presently preferred to be of human origin, in particular a variant of a polypeptide having the amino acid sequence of SEQ ID NO:1.

In preferred embodiments of the present invention more than one amino acid residue of the polypeptide with G-CSF activity is altered, e.g. the alteration embraces removal as well as introduction of amino acid residues comprising an attachment group for the non-polypeptide moiety of choice.

In addition to the amino acid alterations disclosed herein aimed at removing and/or introducing attachment sites for the non-polypeptide moiety, it will be understood that the amino acid sequence of the polypeptide of the invention may if desired contain other alterations that need not be related to introduction or removal of attachment sites, i.e. other substitutions, insertions or deletions. These may, for example, include truncation of the N- and/or C-terminus by one or more amino acid residues, or addition of one or more extra residues at the N- and/or C-terminus, e.g. addition of a methionine residue at the N-terminus.

The conjugate of the invention has one or more of the following improved properties as compared to hG-CSF, in particular as compared to rhG-CSF (e.g. filgrastim, lenograstim or nartograstim) or known hG-CSF variants: increased ability to reduce the duration of neutropenia, increased functional in vivo half-life, increased serum half-life, reduced renal clearance, reduced receptor-mediated clearance, reduced side effects such as bone pain, and reduced immunogenicity.

It will be understood that the amino acid residue comprising an attachment group for a non-polypeptide moiety, whether it be removed or introduced, will be selected on the basis of the nature of the non-polypeptide moiety of choice and, in most instances, on the basis of the method by which conjugation between the polypeptide and the non-polypeptide moiety is to be achieved. For instance, when the non-polypeptide moiety is a polymer molecule such as a polyethylene glycol or polyalkylene oxide derived molecule amino acid residues comprising an attachment group may be selected from the group consisting of lysine, cysteine, aspartic acid, glutamic acid, histidine and arginine. When conjugation to a lysine residue is to be achieved, a suitable activated molecule is e.g. mPEG-SPA from Shearwater Corp., oxycarbonyl-oxy-N-dicarboxyimide-PEG (U.S. Pat. No. 5,122,614), or PEG available from PolyMASC Pharmaceuticals plc. The first of these will be illustrated further below.

In order to avoid too much disruption of the structure and function of the parent hG-CSF molecule, the total number of amino acid residues to be altered in accordance with the present invention, e.g. as described in the subsequent sections herein, (as compared to the amino acid sequence shown in SEQ ID NO:1) will typically not exceed 15. The exact number of amino acid residues and the type of amino acid residues to be introduced or removed depends in particular on the desired nature and degree of conjugation (e.g. the identity of the non-polypeptide moiety, how many non-polypeptide moieties it is desirable or possible to conjugate to the polypeptide, where conjugation is desired or should be avoided, etc.). Preferably, the polypeptide part of the conjugate of the invention or the polypeptide of the invention comprises an amino acid sequence which differs in 1-15 amino acid residues from the amino acid sequence shown in SEQ ID NO:1, typically in 2-10 amino acid residues, e.g. in 3-8 amino acid residues, such as 4-6 amino acid residues, from the amino acid sequence shown in SEQ ID NO:1. Thus, normally the polypeptide part of the conjugate or the polypeptide of the invention comprises an amino acid sequence which differs from the amino acid sequence shown in SEQ ID NO:1 in 1, 2, 3, 4, 5, 6, 7, 8, 9, 10, 11, 12, 13, 14 or 15 amino acid residues.

The polypeptide part of the conjugate will typically have an amino acid sequence with at least about 80% identity with SEQ ID NO:1, preferably at least about 90%, such as at least about 95%, e.g. at least about 96%, 97%, 98% or 99% sequence identity with SEQ ID NO:1. Amino acid sequence homology/identity is conveniently determined from aligned sequences, using e.g. the ClustalW program, version 1.8, June 1999, using default parameters (Thompson et al., 1994, ClustalW: Improving the sensitivity of progressive multiple sequence alignment through sequence weighting, position-specific gap penalties and weight matrix choice, Nucleic Acids Research, 22: 4673-4680) or from the PFAM families database version 4.0 (http://pfam.wustl.edu/) (*Nucleic Acids Res.* 1999 Jan. 1; 27(1):260-2) by use of GENEDOC version 2.5 (Nicholas, K. B., Nicholas H. B. Jr., and Deerfield, D. W. II. 1997 GeneDoc: Analysis and Visualization of Genetic Variation, EMBNEW.NEWS 4:14; Nicholas, K. B. and Nicholas H. B. Jr. 1997 GeneDoc: Analysis and Visualization of Genetic Variation).

In a preferred embodiment one difference between the amino acid sequence of the polypeptide and the amino acid sequence shown in SEQ ID NO:1 is that at least one and often more, e.g. 1-15, amino acid residues comprising an attachment group for the non-polypeptide moiety has been introduced, preferably by substitution, into the amino acid sequence. Thereby, the polypeptide part is altered in the content of the specific amino acid residues to which the non-polypeptide moiety of choice binds, whereby a more efficient, specific and/or extensive conjugation is achieved. For instance, when the total number of amino acid residues comprising an attachment group for the non-polypeptide of choice is altered to an optimized level, the clearance of the conjugate is typically significantly reduced, due to the altered shape, size and/or charge of the molecule achieved by the conjugation. Furthermore, when the total number of amino acid residues comprising an attachment group for the non-polypeptide of choice is increased, a greater proportion of the polypeptide molecule is shielded by the non-polypeptide moieties of choice, leading to a lower immune response.

The term "one difference" as used in the present application is intended to allow for additional differences being present. Accordingly, in addition to the specified amino acid difference, other amino acid residues than those specified may be mutated.

In a further preferred embodiment one difference between the amino acid sequence of the polypeptide and the amino acid sequence shown in SEQ ID NO:1 is that at least one and preferably more, e.g. 1-15, amino acid residues comprising an attachment group for the non-polypeptide moiety has/have been removed, preferably by substitution, from the amino acid sequence. By removing one or more amino acid residues comprising an attachment group for the non-polypeptide moiety of choice it is possible to avoid conjugation to the non-polypeptide moiety in parts of the polypeptide in which such conjugation is disadvantageous, e.g. in amino acid residues located at or near a functional site of the polypeptide (since conjugation at such a site may result in inactivation or reduced G-CSF activity of the resulting conjugate due to impaired receptor recognition). In the present context the term "functional site" is intended to indicate one or more amino acid residues which is/are essential for or otherwise involved in the function or performance of hG-CSF. Such amino acid residues are a part of the functional site. The functional site may be determined by methods known in the art and is preferably identified by analysis of a structure of the polypeptide complexed to a relevant receptor, such as the hG-CSF receptor (See Aritomi et al. Nature 401:713-717, 1999).

In a still further preferred embodiment, the amino acid sequence of the polypeptide differs from the amino acid sequence shown in SEQ ID NO:1 in that a) at least one specified amino acid residue comprising an attachment group for the non-polypeptide moiety and present in the amino acid sequence shown in SEQ ID NO:1 has been removed, preferably by substitution, and b) at least one specified amino acid residue comprising an attachment group for the non-polypeptide moiety has been introduced into the amino acid sequence, preferably by substitution, the specified amino acid residues being any of those described in the subsequent sections herein. This embodiment is considered of particular interest in that it is possible to specifically design the polypeptide so as to obtain an optimal conjugation to the non-polypeptide moiety of choice. For instance, by introducing and removing selected amino acid residues as disclosed in the following sections it is possible to ensure an optimal distribution of attachment groups for the non-polypeptide moiety of choice, which gives rise to a conjugate in which the non-polypeptide moieties are placed so as to a) effectively shield epitopes and other surface parts of the polypeptide and b) ensure an optimal Stokes radius of the conjugate, without causing too much structural disruption and thereby impair the function of the polypeptide.

The conjugate of the invention will in general comprise a sufficient number and type of non-polypeptide moieties to provide the conjugate with an increased functional in vivo half-life and/or serum half-life as compared to hG-CSF, e.g. filgrastim, lenograstim or nartograstim, and preferably as compared to rhG-CSF comprising a single N-terminally attached 20 kDa PEG moiety. The increased functional in vivo half-life is conveniently determined as described in the Materials and Methods section herein.

The conjugate of the invention may comprise at least one non-conjugated, conjugatable attachment group for the non-polypeptide moiety. In the present context the term "conjugatable attachment group" is intended to indicate an attachment group that is located in a position of the polypeptide where it is accessible for conjugation, and that but for special precautions is conjugated to the relevant non-polypeptide moiety when subjected to conjugation. For instance, such attachment group may be part of an amino acid residue involved in or otherwise essential for the polypeptide to exert its activity. A convenient way to avoid conjugation of an otherwise conjugatable attachment group is to shield the attachment group by means of a helper molecule, e.g. as described in the section entitled "Blocking of the functional site". It will be understood that the number of non-conjugated, conjugatable attachment groups depends on the specific G-SCF polypeptide and the location of the conjugatable attachment groups. For instance, the polypeptide conjugate comprises one or two non-conjugated, conjugatable attachment groups, and at least one, and preferably two or more conjugated attachment groups.

The four helices of G-CSF comprise amino acid residues 11-41 (helix A), 71-95 (helix B), 102-125 (helix C), and 145-170 (helix D) (Zink et al. (1994) *Biochemistry* 33: 8453-8463). Surprisingly, it has been found that advantageous results may be obtained when non-polypeptide moieties are attached to amino acid residues located in one or more of the helices of G-CSF, even though modification of protein helices, e.g. the helix structures of four-helix bundle proteins such as G-CSF, is generally considered to be accompanied by a risk of disturbance of protein function. In one embodiment, the polypeptide conjugate of the invention therefore comprises at least one non-polypeptide moiety attached to an attachment group of an amino acid residue located in one of the four helices, in particular in one or more of the B, C or D helices Conjugate of the Invention Wherein the Non-Polypeptide Moiety is Attached to a Lysine or the N-Terminal Amino Acid Residue In one aspect the invention relates to a polypeptide conjugate comprising i) a polypeptide exhibiting G-CSF activity, comprising an amino acid sequence that differs from the amino acid sequence shown in SEQ ID NO:1 in at least one substitution selected from the group consisting of T1K, P2K, L3K, G4K, P5K, A6K, S7K, S8K, L9K, P10K, Q11K, S12K, F13K, L14K, L15K, E19K, Q20K, V21K, Q25K, G26K, D27K, A29K, A30K, E33K, A37K, T38K, Y39K, L41K, H43K, P44K, E45K, E46K, V48K, L49K, L50K, H52K, S53K, L54K, I56K, P57K, P60K, L61K, S62K, S63K, P65K, S66K, Q67K, A68K, L69K, Q70K, L71K, A72K, G73K, S76K, Q77K, L78K, S80K, F83K, Q86K, G87K, Q90K, E93K, G94K, S96K, P97K, E98K, L99K, G100K, P101K, T102K, D104K, T105K, Q107K, L108K, D109K, A111K, D112K, F113K, T115K, T116K, W118K, Q119K, Q120K, M121K, E122K, E123K, L124K, M126K, A127K, P128K, A129K, L130K, Q131K, P132K, T133K, Q134K, G135K, A136K, M137K, P138K, A139K, A141K, S142K, A143K, F144K, Q145K, S155K, H156K, Q158K, S159K, L161K, E162K, V163K, S164K, Y165K, V167K, L168K, H170K, L171K, A172K, Q173K and P174K, and ii) at least one non-polypeptide moiety attached to a lysine residue of the polypeptide.

hG-CSF contains four lysine residues, of which K16 is located in the receptor-binding domain and the others are located in positions 23, 34 and 40, respectively, all relatively close to the receptor-binding domain. In order to avoid conjugation to one or more of these lysine residues (since this may inactivate or severely reduce the activity of the resulting conjugate) it may be desirable to remove at least one lysine residue, e.g. two, three or all of these residues. Accordingly, in another, more preferred aspect the invention relates to a polypeptide conjugate as defined above, wherein at least one of the amino acid residues selected from the group consisting of K16, K23, K34 and K40 has been deleted or substituted with another amino acid residue. Preferably, at least K16 is substituted with another amino acid residue.

Examples of preferred amino acid substitutions include one or more of Q70K, Q90K, T105K, Q120K, T133K, S159K and H170K/Q/R, such as two, three, four or five of these substitutions, for example: Q70K+Q90K, Q70K+T105K, Q70K+Q120K, Q70K+T133K, Q70K+S159K, Q70K+H170K, Q90K+T105K, Q90K+Q120K, Q90K+T133K, Q90K+S159K, Q90K+H170K, T105K+Q120K, T105K+T133K, T105K+S159K, T105K+H170K, Q120K+T133K, Q120K+S159K, Q120K+H170K, T133K+S159K, T133K+H170K, S159K+H170K, Q70K+Q90K+T105K, Q70K+Q90K+Q120K, Q70K+Q90K+T133K, Q70K+Q90K+S159K, Q70K+Q90K+H170K, Q70K+T105K+Q120K, Q70K+T105K+T133K, Q70K+T105K+S159K, Q70K+T105K+H170K, Q70K+Q120K+T133K, Q70K+Q120K+S159K, Q70K+Q120K+H170K, Q70K+T133K+ S159K, Q70K+T133K+H170K, Q70K+S159K+H170K, Q90K+T105K+Q120K, Q90K+T105K+T133K, Q90K+T105K+S159K, Q90K+T105K+H170K, Q90K+Q120K+H170K, T133K, Q90K+Q120K+S159K, Q90K+Q120K+H170K, Q90K+T133K+S159K, Q90K+T133K+H170K, Q90+S159K+H170K, T105K+Q120K+T133K, T105K+Q120K+S159K, T105K+Q120K+H170K, T105K+T133K+S159K, T105K+T133K+H170K, T105K+S159K+H170K, Q120K+T133K+S159K, Q120K+T133K+H170K, Q120K+S159K+H170K, T133K+S159K+H170K, Q70K+Q90K+T105K+Q120K, Q70K+Q90K+T105K+T133K, Q70K+Q90K+T105K+S159K, Q70K+Q90K+T105K+H170K, Q70K+Q90K+Q120K+T133K, Q70K+Q90K+Q120K+S159K, Q70K+Q90K+Q120K+H170K, Q70K+Q90K+T133K+S159K, Q70K+Q90K+T133K+H170K, Q70K+Q90K+S159K+H170K, Q70K+T105K+Q120K+T133K, Q70K+T105K+Q120K+S159K, Q70K+T105K+Q120K+H170K, Q70K+T105K+T133K+S159K, Q70K+T105K+T133K+H170K, Q70K+T105K+S159K+H170K, Q70K+Q120K+T133K+S159K, Q70K+Q120K+T133K+H170K, Q70K+T133K+S159K+H170K, Q90K+T105K+Q120K+T133K, Q90K+T105K+Q120K+S159K, Q90K+T105K+Q120K+H170K, Q90K+T105+T133K+S159K, Q90K+T105+T133K+H170K, Q90K+T105K+S159K+H170K, Q90K+Q120K+T133K+S159K, Q90K+Q120K+T133K+H170K, Q90K+Q120K+S159K+H170K, Q90K+T133K+S159K+H170K, T105K+Q120K+T133K+S159K, T105K+Q120K+T133K+H170K, T105K+Q120K+S159K+H170K, T105K+T133K+S159K+H170K or Q120K+T133K+S159K+H170K. In any of the variants listed above, the substitution H170K may instead be H170Q or H170R.

The polypeptide of the conjugate according to this aspect of the invention, i.e. having at least one introduced and one removed lysine, preferably comprises at least one, such as one, two, three or four, of the substitutions selected from the group consisting of K16R, K16Q, K23R, K23Q, K34R, K34Q, K40R and K40Q, preferably at least the substitution K16R, whereby conjugation of this residue can be avoided. Preferably, the polypeptide comprises at least one substitution selected from the group consisting of K16R+K23R, K16R+K34R, K16R+K40R, K23R+K34R, K23R+K40R, K34R+K40R, K16R+K23R+K34R, K16R+K23R+K40R, K23R+K34R+K40R, K16R+K34R+K40R and K16R+K23R+K34R+K40R. In one preferred embodiment, the polypeptide includes the substitutions K16R+K34R+K40R, while the lysine in position 23 is left unaltered. As indicated above, it is contemplated that any of the individual substitutions or combinations listed in this paragraph for removal of a lysine residue may suitably be used with any of the other substitutions disclosed herein for introduction of lysine residues, in particular the substitutions listed in the paragraph above.

In a particular embodiment the polypeptide includes the substitutions K16R, K34R, K40R, T105K and S159K and is conjugated to 2-6, typically 3-6 polyethylene glycol moieties with a molecular weight of about 1000-10,000 Da.

In one embodiment the conjugate of the invention has a glycosylation in T133, i.e. this position is unaltered from the wild-type hG-CSF. This is the natural glycosylation site. Alternatively, the conjugate may be non-glycosylated, although glycosylated conjugates are preferred.

In particular, the conjugate may have 2-6, typically 3-6 polyethylene glycol moieties with a molecular weight of about 5000-6000 Da attached, e.g. mPEG with a molecular weight of about 5 kDa. Preferably, the conjugate has 4-5 polyethylene glycol moieties with a molecular weight of about 5000-6000 Da attached, e.g. 5 kDa mPEG.

In another embodiment, the conjugate may be produced so as to have only a single number of PEG moieties attached, e.g. either 2, 3, 4, 5 or 6 PEG moieties per polypeptide, or to have a desired mix of polypeptide conjugates with different numbers of PEG moieties attached, e.g. a mix having 2-5, 2-4, 3-5, 3-4, 4-6, 4-5 or 5-6 attached PEG moieties. As indicated above, an example of a preferred conjugate mix is one having 4-5 PEG moieties of about 5 kDa.

It will be understood that a conjugate having a specific number of attached PEG moieties, or a mix of conjugates having a defined range of numbers of attached PEG moieties, may be obtained by choosing suitable PEGylation conditions and optionally by using subsequent purification to separate conjugates having the desired number of PEG moieties. Examples of methods for separation of G-CSF molecules with different numbers of PEG moieties attached are provided below. Determination of the number of attached PEG moieties may e.g. be performed using SDS-PAGE. For purposes of the present invention, a polypeptide conjugate may be considered to have a given number of attached PEG moieties if separation on an SDS-PAGE gel shows no or only insignificant bands other than the band(s) corresponding to the given number(s) of PEG moieties. For example, a sample of a polypeptide conjugate is considered to have 4-5 attached PEG groups if an SDS-PAGE gel on which the sample has been run shows bands corresponding to 4 and 5 PEG groups, respectively, and only insignificant bands or, preferably, no bands corresponding to 3 or 6 PEG groups.

While the non-polypeptide moiety of the conjugate according to this aspect of the invention may be any molecule which, when using the given conjugation method has lysine as an attachment group such as a carbohydrate moiety, it is preferred that the non-polypeptide moiety is a polymer molecule. The polymer molecule may be any of the molecules mentioned in the section entitled "Conjugation to a polymer molecule", but is preferably selected from the group consisting of linear or branched polyethylene glycol or another polyalkylene oxide. Preferred polymer molecules are e.g. mPEG-SPA (in particular SPA-mPEG 5000) from Shearwater Corp. or oxycarbonyl-oxy-N-dicarboxyimide PEG (U.S. Pat. No. 5,122,614).

It will be understood that any of the amino acid changes, in particular substitutions, specified in this section can be combined with any of the amino acid changes, preferably substitutions, specified in the other sections herein disclosing specific amino acid modifications, including introduction and/or removal of glycosylation sites.

Conjugate of the Invention Wherein the Non-Polypeptide Moiety is a Molecule which has Cysteine as an Attachment Group In another aspect the invention relates to a conjugate comprising i) a polypeptide exhibiting G-CSF activity, which comprises an amino acid sequence that differs from the amino acid sequence of hG-CSF shown in SEQ ID NO:1 in at least one substitution selected from the group consisting of T1C, P2C, L3C, G4C, P5C, A6C, S7C, S8C, L9C, P10C, Q11C, S12C, F13C, L14C, L15C, E19C, Q20C, V21C, R22C, Q25C, G26C, D27C, A29C, A30C, E33C, A37C, T38C, Y39C, L41C, H43C, P44C, E45C, E46C, V48C, L49C, L50C, H52C, S53C, L54C, I56C, P57C, P60C, L61C, S62C, S63C, P65C, S66C, Q67C, A68C, L69C, Q70C, L71C, A72C, G73C, S76C, Q77C, L78C, S80C, F83C, Q86C, G87C, Q90C, E93C, G94C, S96C, P97C, E98C, L99C, G100C, P101C, T102C, D104C, T105C, Q107C, L108C, D109C, A111C, D112C, F113C, T115C, T116C, W118C, Q119C, Q120C, M121C, E122C, E123C, L124C, M126C, A127C, P128C, A129C, L130C, Q131C, P132C, T133C, Q134C, G135C, A136C, M137C, P138C, A139C, A141C, S142C, A143C, F144C, Q145C, R146C, R147C, S155C, H156C, Q158C, S159C, L161C, E162C, V163C, S164C, Y165C, R166C, V167C, L168C, R169C, H170C, L171C, A172C, Q173C and P174C, and ii) at least one non-polypeptide moiety attached to a cysteine residue of the polypeptide.

The receptor-binding domain of hG-CSF contains a cysteine residue in position 17 which does not take part in a cystine and which may advantageously be removed in order to avoid conjugation of a non-polypeptide moiety to said cysteine. Accordingly, in another, more preferred aspect the invention relates to a conjugate comprising i) a polypeptide exhibiting G-CSF activity, which comprises an amino acid sequence that differs from the amino acid sequence shown in SEQ ID NO:1 in at least one substitution selected from the group consisting of T1C, P2C, L3C, G4C, P5C, A6C, S7C, S8C, L9C, P10C, Q11C, S12C, F13C, L14C, L15C, E19C, Q20C, V21C, R22C, Q25C, G26C, D27C, A29C, A30C, E33C, A37C, T38C, Y39C, L41C, H43C, P44C, E45C, E46C, V48C, L49C, L50C, H52C, S53C, L54C, I56C, P57C, P60C, L61C, S62C, S63C, P65C, S66C, Q67C, A68C, L69C, Q70C, L71C, A72C, G73C, S76C, Q77C, L78C, S80C, F83C, Q86C, G87C, Q90C, E93C, G94C, S96C, P97C, E98C, L99C, G100C, P101C, T102C, D104C, T105C, Q107C, L108C, D109C, A111C, D112C, F113C, T115C, T116C, W118C, Q119C, Q120C, M121C, E122C, E123C, L124C, M126C, A127C, P128C, A129C, L130C, Q131C, P132C, T133C, Q134C, G135C, A136C, M137C, P138C, A139C, A141C, S142C, A143C, F144C, Q145C, R146C, R147C, S155C, H156C, Q158C, S159C, L161C, E162C, V163C, S164C, Y165C, R166C, V167C, L168C, R169C, H170C, L171C, A172C, Q173C and P174C, in combination with removal of C17, preferably substitution of C17 with any other amino acid residue, e.g. with a serine residue, and ii) a non-polypeptide moiety which has a cysteine residue as an attachment group.

Preferred substitutions according to this aspect of the invention are substitutions of arginine with cysteine, for example one or more of R146C, R147C, R166C and R169C.

It will be understood that any of the amino acid modifications, in particular substitutions, specified in this section can be combined with any of the amino acid changes, in particular substitutions, specified in the other sections herein disclosing specific amino acid modifications, including introduction and/or removal of glycosylation sites.

Conjugate of the Invention Wherein the Non-Polypeptide Moiety Binds to an Acid Group or the C-Terminal Amino Acid Residue In a still further aspect the invention relates to a conjugate comprising i) a polypeptide exhibiting G-CSF activity, which comprises an amino acid sequence that differs from the amino acid sequence shown in SEQ ID NO:1 in at least one substitution selected from the group consisting of T1D, P2D, L3D, G4D, P5D, A6D, S7D, S8D, L9D, P10D, Q11D, S12D, F13D, L14D, L15D, K16D, Q20D, V21D, R22D, K23D, Q25D, G26D, A29D, A30D, K34D, A37D, T38D, Y39D, K40D, L41D, H43D, P44D, V48D, L49D, L50D, H52D, S53D, L54D, I56D, P57D, P60D, L61D, S62D, S63D, P65D, S66D, Q67D, A68D, L69D, Q70D, L71D, A72D, G73D, S76D, Q77D, L78D, S80D, F83D, Q86D, G87D, Q90D, G94D, S96D, P97D, L99D, G100D, P101D, T102D, T105D, Q107D, L108D, A111D, F113D, T115D, T116D, W118D, Q119D, Q120D, M121D, L124D, M126D, A127D, P128D, A129D, L130D, Q131D, P132D, T133D, Q134D, G135D, A136D, M137D, P138D, A139D, A141D, S142D, A143D, F144D, Q145D, R146D, R147D, S155D, H156D, Q158D, S159D, L161D, V163D, S164D, Y165D, R166D, V167D, L168D, R169D, H170D, L171D, A172D, Q173D and P174D; or at least one substitution selected from the group consisting of T1E, P2E, L3E, G4E, P5E, A6E, S7E, S8E, L9E, P10E, Q11E, S12E, F13E, L14E, L15E, K16E, Q20E, V21E, R22E, K23E, Q25E, G26E, A29E, A30E, K34E, A37E, T38E, Y39E, K40E, L41E, H43E, P44E, V48E, L49E, L50E, H52E, S53E, L54E, I56E, P57E, P60E, L61E, S62E, S63E, P65E, S66E, Q67E, A68E, L69E, Q70E, L71E, A72E, G73E, S76E, Q77E, L78E, S80E, F83E, Q86E, G87E, Q90E, G94E, S96E, P97E, L99E, G100E, P101E, T102E, T105E, Q107E, L108E, A111E, F113E, T115E, T116E, W118E, Q119E, Q120E, M121E, L124E, M126E, A127E, P128E, A129E, L130E, Q131E, P132E, T133E, Q134E, G135E, A136E, M137E, P138E, A139E, A141E, S142E, A143E, F144E, Q145E, R146E, R147E, S155E, H156E, Q158E, S159E, L161E, V163E, S164E, Y165E, R166E, V167E, L168E, R169E, H170E, L171E, A172E, Q173E and P174E; and ii) a non-polypeptide moiety having an aspartic acid or a glutamic acid residue as an attachment group.

Examples of preferred substitutions according to this aspect of the invention include Q67D/E, Q70D/E, Q77D/E, Q86D/E, Q90D/E, Q120D/E, Q131D/E, Q134D/E, Q145D/E and Q173D/E.

In addition to the above listed substitutions, the polypeptide of the conjugate according to any of the above aspects may comprise removal, preferably by substitution, of at least one of the amino acid residues selected from the group consisting of D27, D104, D109, D112, E19, E33, E45, E46, E93, E98, E122, E123, and E163. The substitution may be for any other amino acid residue, in particular for an asparagine or a glutamine residue, whereby conjugation of these residues can be avoided. In particular, the polypeptide may comprise at least one of the following substitutions: D27N, D104N, D109N, D112N, E19Q, E33Q, E45Q, E46Q, E93Q, E98Q, E122Q, E123Q and E163Q. Preferably, the amino acid substitution in one or more of the above positions may in addition be combined with at least one of the following substitutions: D109N, D112N, E19Q, E122Q and E123Q.

While the non-polypeptide moiety of the conjugate according to this aspect of the invention, which has an acid group as an attachment group, can be any non-polypeptide moiety with such property, it is presently preferred that the non-polypeptide moiety is a polymer molecule or an organic derivatizing agent, in particular a polymer molecule, and the conjugate is prepared e.g. as described by Sakane and Pardridge, Pharmaceutical Research, Vol. 14, No. 8, 1997, pp 1085-1091.

It will be understood that any of the amino acid changes, in particular substitutions, specified in this section can be combined with any of the amino acid changes, in particular substitutions specified in the other sections herein disclosing specific amino acid changes, including introduction and/or removal of glycosylation sites.

Other Conjugates of the Invention

In addition to the non-polypeptide moieties specified above e.g. in the sections entitled "Conjugate of the invention..." the conjugate of the invention may contain one or more carbohydrate moieties as a consequence of the polypeptide being expressed in a glycosylating host cell to result in glycosylation at the natural glycosylation site of hG-CSF (T133) and/or at introduced glycosylation site(s).

Conjugate of the Invention Wherein the Non-Polypeptide Moiety is a Carbohydrate Moiety In a further aspect the invention relates to a conjugate comprising a glycosylated polypeptide exhibiting G-CSF activity, which comprises an amino acid sequence that differs from that shown in SEQ ID NO:1 in that at least one non-naturally occurring glycosylation site has been introduced into the amino acid sequence by way of at least one substitution selected from the group consisting of L3N+P5S/T, P5N, A6N, S8N+P10S/T, P10N, Q11N+F13S/T, S12N+L14S/T, F13N+L15S/T, L14N+K16S/T, K16N+L18S/T, E19N+V21S/T, Q20N+R22S/T, V21N+K23S/T, R22N+124S/T, K23N+Q25S/T, Q25N+D27S/T, G26N+G28S/T, D27N+A29S/T, A29N+L31S/T, A30N+Q32S/T, E33N+L35S/T, A37N+Y39S/T, T38N+K40S/T, Y39N+L41S/T, P44N+E46S/T, E45N+L47S/T, E46N+V48S/T, V48N+L50S/T, L49N+G51S/T, L50N+H52S/T, H52N+L54S/T, S53N+G55S/T, P60N, L61N, S63N+P65S/T, P65N+Q67S/T, S66N+A68S/T, Q67N+L69S/T, A68N+Q70S/T, L69N+L71S/T, Q70N+A72S/T, L71N+G73S/T, G73N+L75S/T, S76N+L78S/T, Q77N+H79S/T, L78N, S80N+L82S/T, F83N+Y85S/T, Q86N+L88S/T, G87N+L89S/T, Q90N+L92S/T, E93N+I95S/T, P97N+L99S/T, L99N+P101S/T, P101N+L103S/T, T102N+D104S/T, D104N+L106S/T, T105N+Q107S/T, Q107N+D109S/T, L108N+V110S/T, D109N+A111S/T, A111N+F113S/T, D112N+A114S/T, F113N, T115N+I117S/T, T116N+W118S/T, W118N+Q120S/T, Q119N+M121S/T, Q120N+E122S/T, M121N+E123S/T, E122N+L124S/T, E123N+G125S/T, L124N+M126S/T, M126N+P128S/T, P128N+L130S/T, L130N+P132S/T, P132N+Q134S/T, T133N+G135S/T, Q134N+A136S/T, A136N+P138S/T, P138N+F140S/T, A139N+A141S/T, A141N+A143S/T, S142N+F144S/T, A143N+Q145S/T, F144N+R146S/T, Q145N+R147S/T, R146N+A148S/T, R147N+G149S/T, S155N+L157S/T, H156N+Q158S/T, S159N+L161S/T, L161N+V163S/T, E162N, V163N+Y165S/T, S164N+R166S/T, Y165N+V167S/T, R166N+L168S/T, V167N+R169S/T, L168N+H170S/T, R169N+L171S/T and H170N+A172S/T, wherein S/T indicates an S or a T residue, preferably a T residue.

It will be understood that in order to prepare a conjugate according to this aspect the polypeptide must be expressed in a glycosylating host cell capable of attaching oligosaccharide moieties at the glycosylation site(s) or alternatively subjected to in vitro glycosylation. Examples of glycosylating host cells are given in the section further below entitled "Coupling to an oligosaccharide moiety".

Alternatively, the conjugate according to this aspect comprises a polypeptide exhibiting G-CSF activity, which comprises an amino acid sequence that differs from that shown in SEQ ID NO:1 in at least one substitution selected from the group consisting of P5N, A6N, P10N, P60N, L61N, L78N, F113N and E162N, in particular from the group consisting of P5N, A6N, P10N, P60N, L61N, F113N and E162N, such as from the group consisting of P60N, L61N, F113N and E162N.

Alternatively, the conjugate according to this aspect comprises a polypeptide exhibiting G-CSF activity, which comprises an amino acid sequence that differs from that shown in SEQ ID NO:1 in at least one substitution selected from the group consisting of D27N+A29S, D27N+A29T, D104N+L106S, D104N+L106T, D109N+A111S, D109N+A111T, D112N+A114S and D112N+A114T, more preferably from the group consisting of D27N+A29S, D27N+A29T, D104N+

L106S, D104N+L106T, D112N+A114S and D112N+A114T, such as from the group consisting of D27N+A29S, D27N+A29T, D104N+L106S and D104N+L106T.

In addition to a carbohydrate molecule, the conjugate according to the aspect of the invention described in the present section may contain additional non-polypeptide moieties, in particular a polymer molecule, as described in the present application, conjugated to one or more attachment groups present in the polypeptide part of the conjugate.

It will be understood that any of the amino acid changes, in particular substitutions, specified in this section can be combined with any of the amino acid changes, in particular substitutions, specified in the other sections herein disclosing specific amino acid changes.

Circularly Permuted Variants

In a further embodiment, the polypeptide part of the polypeptide conjugate of the invention may be in the form of a circularly permuted variant of a polypeptide sequence otherwise disclosed herein. In such a circularly permuted polypeptide, the original N-terminus and C-terminus are joined together either directly by a peptide bond or indirectly via a peptide linker, while new N- and C-termini are formed between two adjacent amino acid residues that originally were joined by a peptide bond. Since the original N- and C-termini will normally be located at some distance from each other, they will typically be linked by means of a peptide linker having a suitable length and composition so that the structure and activity of the conjugate is not adversely affected. It will be clear that the new N-terminus and C-terminus should not be formed between an amino acid residue pair where this would interfere with the activity of the polypeptide. Circularly permuted G-CSF receptor agonists are disclosed in U.S. Pat. No. 6,100,070, to which reference is made for further information on selecting peptide linkers and the location of the new N-terminus and C-terminus as well as methods for producing them such variants.

White Blood Cell and Neutrophil Formation of Conjugates of the Invention

In a further embodiment, the polypeptide conjugate of the invention may be characterized as being a conjugate exhibiting G-CSF activity and comprising a polypeptide with an amino acid sequence that differs in at least one amino acid residue from the amino acid sequence shown in SEQ ID NO:1 and having at least one non-polypeptide moiety attached to an attachment group of the polypeptide, the polypeptide conjugate further fulfilling at least one of the following criteria (A)-(D):

(A) after one subcutaneous administration of 100 microgram per kg body weight to rats (based on the weight of the polypeptide part of the conjugate) it:
  i) increases formation of white blood cells with at least about the same rate and to at least about the same level (measured as number of cells per liter of blood) as administration of 100 microgram of non-conjugated hG-CSF per kg body weight for a period of 6 hours, preferably 12 hours after administration, and
  ii) increases the level of white blood cells (measured as number of cells per liter blood) above the level of white blood cells prior to administration for a period of at least about 96 hours, preferably for at least about 120 hours;

(B) after one subcutaneous administration of 25 microgram per kg body weight to rats (based on the weight of the polypeptide part of the conjugate) it:
  i) increases formation of white blood cells with at least about the same rate and to at least about the same level (measured as number of cells per liter of blood) as administration of 100 microgram of non-conjugated hG-CSF per kg body weight for a period of 6 hours, preferably 12 hours after administration, and
  ii) increases the level of white blood cells (measured as number of cells per liter blood) above the level of white blood cells prior to administration for a period of at least about 72 hours, preferably at least about 96 hours, more preferably at least about 120 hours;

(C) after one subcutaneous administration of 100 microgram per kg body weight to rats (based on the weight of the polypeptide part of the conjugate) it:
  i) increases formation of neutrophils with at least about the same rate and to at least about the same level (measured as number of cells per liter of blood) as administration of 100 microgram of non-conjugated hG-CSF per kg body weight for a period of 6 hours, preferably 12 hours after administration, and
  ii) increases the level of neutrophils (measured as number of cells per liter blood) above the level of neutrophils prior to administration for a period of at least about 96 hours, preferably at least about 120 hours;

(D) after one subcutaneous administration of 25 microgram per kg body weight to rats (based on the weight of the polypeptide part of the conjugate) it:
  i) increases formation of neutrophils with at least about the same rate and to at least about the same level (measured as number of cells per liter of blood) as administration of 100 microgram of non-conjugated hG-CSF per kg body weight for a period of 6 hours, preferably 12 hours after administration, and
  ii) increases the level of neutrophils (measured as number of cells per liter blood) above the level of neutrophils prior to administration for a period of at least about 72 hours, preferably at least about 96 hours, more preferably at least about 120 hours.

Non-Polypeptide Moiety of the Conjugate of the Invention

As indicated further above the non-polypeptide moiety of the conjugate of the invention is preferably selected from the group consisting of a polymer molecule, a lipophilic compound, a carbohydrate moiety (e.g. by way of in vivo glycosylation) and an organic derivatizing agent. All of these agents may confer desirable properties to the polypeptide part of the conjugate, in particular increased functional in vivo half-life and/or increased serum half-life. The polypeptide part of the conjugate is normally conjugated to only one type of non-polypeptide moiety, but may also be conjugated to two or more different types of non-polypeptide moieties, e.g. to a polymer molecule and an oligosaccharide moiety, to a lipophilic group and an oligosaccharide moiety, to an organic derivatizing agent and an oligosaccharide moiety, to a lipophilic group and a polymer molecule, etc. The conjugation to two or more different non-polypeptide moieties may be done simultaneously or sequentially.

Methods for Preparing a Conjugate of the Invention

In the following sections "Conjugation to a lipophilic compound", "Conjugation to a polymer molecule", "Conjugation to an oligosaccharide moiety" and "Conjugation to an organic derivatizing agent" conjugation to specific types of non-polypeptide moieties is described. In general, a polypeptide conjugate according to the invention may be produced by culturing an appropriate host cell under conditions conducive for expression of the polypeptide, and recovering the polypeptide, wherein a) the polypeptide comprises at least one N- or O-glycosylation site and the host cell is a eukaryotic host cell capable of in vivo glycosylation, and/or b) the polypeptide is subjected to conjugation to a non-polypeptide moiety in vitro.

Conjugation to a Lipophilic Compound

The polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamin, a carotenoid or steroid, or a synthetic compound such as a carbon acid, an alcohol, an amine and sulphonic acid with one or more alkyl, aryl, alkenyl or other multiple unsaturated compounds. The conjugation between the polypeptide and the lipophilic compound, optionally through a linker, may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of about 300-100,000 Da, such as about 500-20,000 Da, more preferably in the range of about 1000-15,000 Da, even more preferably in the range of about 2000-12,000 Da, such as about 3000-10,000. When used about polymer molecules herein, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer which comprises different coupling groups, such as a hydroxyl group and an amine group.

Examples of suitable polymer molecules include polymer molecules selected from the group consisting of polyalkylene oxide (PAO), including polyalkylene glycol (PAG), such as linear or branched polyethylene glycol (PEG) and polypropylene glycol (PPG), poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Shearwater Corp., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Corp. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the polypeptide (i.e. such attachment groups that are exposed at the surface of the polypeptide) or may be directed towards one or more specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form of such molecules (e.g. whether they are linear or branched), and where in the polypeptide such molecules are attached. The molecular weight of the polymer to be used will be chosen taking into consideration the desired effect to be achieved. For instance, if the primary purpose of the conjugation is to achieve a conjugate having a high molecular weight and larger size (e.g. to reduce renal clearance), one may choose to conjugate either one or a few high molecular weight polymer molecules or a number of polymer molecules with a smaller molecular weight to obtain the desired effect. Preferably, however, several polymer molecules with a lower molecular weight will be used. This is also the case if a high degree of epitope shielding is desired. In such cases, 2-8 polymers with a molecular weight of e.g. about 5,000 Da, such as 3-6 such polymers, may for example be used. As the examples below illustrate, it may be advantageous to have a larger number of polymer molecules with a lower molecular weight (e.g. 4-6 with a MW of 5000) compared to a smaller number of polymer molecules with a higher molecular weight (e.g. 1-3 with a MW of 12,000-20,000) in terms of improving the functional in vivo half-life of the polypeptide conjugate, even where the total molecular weight of the attached polymer molecules in the two cases is the same or similar. It is believed that the presence of a larger number of smaller polymer molecules provides the polypeptide with a larger diameter or apparent size than e.g. a single yet larger polymer molecule, at least when the polymer molecules are relatively uniformly distributed on the polypeptide surface.

It has further been found that advantageous results are obtained when the apparent size (also referred to as the "apparent molecular weight" or "apparent mass") of at least a major portion of the conjugate of the invention is at least about 50 kDa, preferably at least about 55 kDa, more preferably at least about 60 kDa, e.g. at least about 66 kDa. This is believed to be due to the fact that renal clearance is substantially eliminated for conjugates having a sufficiently large apparent size. In the present context, the "apparent size" of a G-CSF conjugate or polypeptide is determined by the SDS-PAGE method described in the examples section below.

The use of the term "major portion" is related to the fact that the polypeptide conjugates of the invention will typically comprise individual conjugates having varying numbers of non-polypeptide moieties attached. For example, a given polypeptide subjected to PEGylation under a given set of PEGylation conditions may result in a composition in which most of the individual polypeptide conjugates have e.g. between 3 and 5 PEG groups attached, with a majority of the conjugates having 4 PEG groups attached. It will be clear that the apparent molecular weight of these individual conjugate molecules will vary. In this example, if we assume that a G-CSF polypeptide is conjugated to PEG groups with a MW of 5 kDa, conjugates having only 3 PEG groups attached will be seen on an SDS-PAGE gel as a band that is likely to have an apparent molecular weight of less than about 50 kDa, while conjugates having 4 or 5 PEG groups attached will result in bands with progressively higher apparent molecular weights that most likely all are greater than about 50 kDa. Thus, in this example there would be 3 major bands on an SDS-PAGE gel, corresponding to conjugates with 3, 4 or 5 attached PEG groups, respectively. The term "major portion" in the context of the present specification and claims is therefore intended to refer to the fact that at least one of these major bands on an SDS-PAGE gel will correspond to the indicated minimum apparent molecular weight.

Preferably, at least 50% of the individual conjugate molecules will have a minimum apparent size as described above. More preferably, at least 60% of the individual conjugate molecules with have such a minimum apparent size, still more preferably at least 70%, 75%, 80% or 85%. Most preferably, at least 90% of the individual conjugate molecules will have a minimum apparent size as described above, i.e. at least 50 kDa and preferably higher, such as at least 55 kDa or 60 kDa.

It will be understood that the apparent size in kDa of a conjugate or polypeptide is not necessarily the same as the actual molecular weight of the conjugate or polypeptide. Rather, the apparent size is a reflection of both the actual molecular weight and the overall bulk. Since, in most cases, attachment of one or more PEG groups or other non-polypeptide moieties will result in a relatively large increase of the bulk of the polypeptide to which such moieties are attached, the polypeptide conjugates of the invention will normally have an apparent size that exceeds the actual molecular weight of the conjugate. Therefore, in connection with renal clearance, a conjugate of the invention can easily exhibit properties characteristic of a polypeptide with a molecular weight above e.g. 66 kDa (corresponding to the apparent size) but have an actual molecular weight well below 66 kDa. This effect on apparent size is believed to be responsible for the observation that attachment of, for example, four PEG groups each having a molecular weight of 5 kDa provides results that are superior to a corresponding polypeptide with a single 20 kDa PEG group attached.

While conjugation of only a single polymer molecule to a single attachment group on the protein is not preferred, in the event that only one polymer molecule is attached, it will generally be advantageous that the polymer molecule, which may be linear or branched, has a relatively high molecular weight, e.g. about 20 kDa.

In a further preferred embodiment, the conjugates of the invention have 1) at least a major portion with an apparent molecular weight of at least about 50 kDa and 2) a reduced in vitjo bioactivity (reduced receptor binding affinity) compared to hG-CSF as described above. It has been found that such conjugates have both a low renal clearance as a result of the large apparent size and a low receptor-mediated clearance as a result of the low in vitro bioactivity (low receptor binding affinity). The overall result is excellent performance in terms of effective stimulation of neutrophils together with a significantly increased in vivo half-life and thus a long duration of action that provides important clinical advantages.

Normally, the polymer conjugation is performed under conditions aiming at reacting as many of the available polymer attachment groups as possible with polymer molecules. This is achieved by means of a suitable molar excess of the polymer in relation to the polypeptide (number of attachment sites). Typical molar ratios of activated polymer molecules to polypeptide attachment sites are up to about 1000-1, such as up to about 200-1 or up to about 100-1. In some cases, the ratio may be somewhat lower, however, such as up to about 50-1, 10-1 or 5-1, e.g. if a lower degree of polymer attachment is desired.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378.

Subsequent to the conjugation residual activated polymer molecules are blocked according to methods known in the art, e.g. by addition of primary amine to the reaction mixture, and the resulting inactivated polymer molecules are removed by a suitable method (see Materials and Methods).

In a preferred embodiment, the polypeptide conjugate of the invention comprises a PEG molecule attached to some, most or preferably substantially all of the lysine residues in the polypeptide available for PEGylation, in particular a linear or branched PEG molecule, e.g. with a molecular weight of about 1-15 kDa, typically about 2-12 kDa, such as about 3-10 kDa, e.g. about 5 or 6 kDa.

It will be understood that depending on the circumstances, e.g. the amino acid sequence of the polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to polypeptide. The PEGylated polypeptides resulting from any given PEGylation process will, however, normally comprise a stochastic distribution of polypeptide conjugates having slightly different degrees of PEGylation. If desired, such a mixture of polypeptide species having different numbers of PEG moieties attached may be subjected to purification, e.g. using the methods described in the examples below, to obtain a product having a more uniform degree of PEGylation.

In yet another embodiment, the polypeptide conjugate of the invention may comprise a PEG molecule attached to the lysine residues in the polypeptide available for PEGylation, and in addition to the N-terminal amino acid residue of the polypeptide.

Coupling to an Oligosaccharide Moiety

The conjugation to an oligosaccharide moiety may take place in vivo or in vitro. In order to achieve in vivo glycosylation of a G-CSF molecule comprising one or more glycosylation sites the nucleotide sequence encoding the polypeptide must be inserted in a glycosylating, eukaryotic expression host. The expression host cell may be selected from fungal (filamentous fungal or yeast), insect or animal cells or from transgenic plant cells. In one embodiment the host cell is a mammalian cell, such as a CHO cell, BHK or HEK, e.g. HEK 293, cell, or an insect cell, such as an SF9 cell, or a yeast cell, e.g. *S. cerevisiae* or *Pichia pastoris*, or any of the host cells mentioned hereinafter. Covalent in vitro coupling of glycosides (such as dextran) to amino acid residues of the polypeptide may also be used, e.g. as described in WO 87/05330 and in Aplin et al., CRC Crit Rev. Biochem., pp. 259-306, 1981.

The in vitro coupling of oligosaccharide moieties or PEG to protein- and peptide-bound Gln-residues can be carried out by transglutaminases (TG'ases). Transglutaminases catalyze the transfer of donor amine-groups to protein- and peptide-bound Gln-residues in a so-called cross-linking reaction. The donor-amine groups can be protein- or peptide-bound e.g. as the ε-amino-group in Lys-residues or can be part of a small or large organic molecule. An example of a small organic molecule functioning as an amino-donor in TG'ase-catalyzed cross-linking is putrescine (1,4-diaminobutane). An example of a larger organic molecule functioning as an amino-donor in TG'ase-catalyzed cross-linking is an amine-containing PEG (Sato et al., Biochemistry 35, 13072-13080).

TG'ases are in general highly specific enzymes, and not every Gln-residue exposed on the surface of a protein is accessible to TG'ase-catalyzed cross-linking to amino-containing substances. On the contrary, only a few Gln-residues function naturally as TG'ase substrates, but the exact parameters governing which Gln-residues are good TG'ase substrates remain unknown. Thus, in order to render a protein susceptible to TG'ase-catalyzed cross-linking reactions it is often a prerequisite to add at convenient positions stretches of amino acid sequence known to function very well as TG'ase substrates. Several amino acid sequences are known to be or to contain excellent natural TG'ase substrates e.g. substance P, elafin, fibrinogen, fibronectin, $\alpha_2$-plasmin inhibitor, α-caseins, and β-caseins.

Coupling to an Organic Derivatizing Agent

Covalent modification of the polypeptide exhibiting G-CSF activity may be performed by reacting one or more attachment groups of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonateat pH 5.5-7.0 because this agent is relatively specific for the histidyl side chain. Para-bromophenacyl bromide is also useful. The reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group.

Furthermore, these reagents may react with the groups of lysine as well as the arginine guanidino group. Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of the Functional Site

It has been reported that excessive polymer conjugation can lead to a loss of activity of the polypeptide to which the polymer is conjugated. This problem can be eliminated by e.g. removal of attachment groups located at the functional site or by blocking the functional site prior to conjugation so that the functional site is blocked during conjugation. The latter strategy constitutes a further embodiment of the invention (the first strategy being exemplified further above, e.g. by removal of lysine residues which may be located close to the functional site). More specifically, according to the second strategy the conjugation between the polypeptide and the non-polypeptide moiety is conducted under conditions where the functional site of the polypeptide is blocked by a helper molecule capable of binding to the functional site of the polypeptide.

Preferably, the helper molecule is one which specifically recognizes a functional site of the polypeptide, such as a receptor, in particular the G-CSF receptor or a part of the G-CSF receptor.

Alternatively, the helper molecule may be an antibody, in particular a monoclonal antibody recognizing the polypeptide exhibiting G-CSF activity. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, an oligosaccharide moiety, an organic derivatizing agent or any other compound is conducted in the normal way, e.g. as described in the sections above entitled "Conjugation to . . .".

Irrespective of the nature of the helper molecule to be used to shield the functional site of the polypeptide from conjugation, it is desirable that the helper molecule is free of or comprises only a few attachment groups for the non-polypeptide moiety of choice in part(s) of the molecule where the conjugation to such groups would hamper desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free of conjugatable epsilon amino groups, preferably free of any epsilon amino groups. Accordingly, in a preferred embodiment the helper molecule is a protein or peptide capable of binding to the functional site of the polypeptide, which protein or peptide is free of any conjugatable attachment groups for the non-polypeptide moiety of choice.

Of particular interest in connection with the embodiment of the present invention wherein the polypeptide conjugates are prepared from a diversified population of nucleotide sequences encoding a polypeptide of interest, the blocking of the functional group is effected in microtiter plates prior to conjugation, for instance by plating the expressed polypeptide variant in a microtiter plate containing an immobilized blocking group such as a receptor, an antibody or the like.

In a further embodiment the helper molecule is first covalently linked to a solid phase such as column packing materials, for instance Sephadex or agarose beads, or a surface, e.g. a reaction vessel. Subsequently, the polypeptide is loaded onto the column material carrying the helper molecule and conjugation carried out according to methods known in the art, e.g. as described in the sections above entitled "Conjugation to . . . ". This procedure allows the polypeptide conjugate to be separated from the helper molecule by elution. The polypeptide conjugate is eluted by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase, thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. Deprotection may be achieved by providing conditions in which the helper molecule dissociates from the functional site of the G-CSF to which it is bound. For instance, a complex between an antibody to which a polymer is conjugated and an anti-idiotypic antibody can be dissociated by adjusting the pH to an acid or alkaline pH.

Conjugation of a Tagged Polypeptide

In an alternative embodiment the polypeptide is expressed as a fusion protein with a tag, i.e. an amino acid sequence or peptide stretch made up of typically 1-30, such as 1-20 amino acid residues. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilized via the tag. The conjugation to the tagged polypeptide in e.g. microtiter plates has the advantage that the tagged polypeptide can be immobilized in the microtiter plates directly from the culture broth (in principle without any purification) and subjected to conjugation. Thereby, the total number of process steps (from expression to conjugation) can be reduced. Furthermore, the tag may function as a spacer molecule, ensuring an improved accessibility to the immobilized polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilized on a suitable surface or carrier material. A number of suitable tags are commercially available, e.g. from Unizyme Laboratories, Denmark. For instance, the tag may consist of any of the following sequences:

```
                                           (SEQ ID NO:5)
Met-Lys-His-Gln-His-Gln-His-Gln-His-Gln-His-Gln-
His-Gln-Gln (SEQ ID NO:9)
His-His-His-His-His-His (SEQ ID NO:10)
Met-Lys-His-His-His-His-His-His (SEQ ID NO:11)
Met-Lys-His-His-Ala-His-His-Gln-His-His (SEQ ID NO:12)
Met-Lys-His-Gln-His-Gln-His-Gln-His-Gln-His-Gln-
His-Gln
``` or any of the following:

EQKLI SEEDL (SEQ ID NO:13; a C-terminal tag described in Mol. Cell. Biol. 5:3610-16, 1985) DYKDDDDK (SEQ ID NO:14; a C- or N-terminal tag) YPYDVPDYA (SEQ ID NO:15)

Antibodies against the above tags are commercially available, e.g. from ADI, Aves Lab and Research Diagnostics.

A convenient method for using a tagged polypeptide for PEGylation is given in the Materials and Methods section below. The subsequent cleavage of the tag from the polypeptide may be achieved by use of commercially available enzymes.

Methods for Preparing a Polypeptide of the Invention or the Polypeptide Part of the Conjugate of the Invention The polypeptide of the present invention or the polypeptide part of a conjugate of the invention, optionally in glycosylated form, may be produced by any suitable method known in the art. Such methods include constructing a nucleotide sequence encoding the polypeptide and expressing the sequence in a suitable transformed or transfected host. However, polypeptides of the invention may be produced, albeit less efficiently, by chemical synthesis or a combination of chemical synthesis or a combination of chemical synthesis and recombinant DNA technology.

A nucleotide sequence encoding a polypeptide or the polypeptide part of a conjugate of the invention may be constructed by isolating or synthesizing a nucleotide sequence encoding the parent G-CSF, such as hG-CSF with the amino acid sequence shown in SEQ ID NO:1, and then changing the nucleotide sequence so as to effect introduction (i.e. insertion or substitution) or deletion (i.e. removal or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR) (Barany, PNAS 88:189-193, 1991). The individual oligonucleotides typically contain 5' or 3' overhangs for complementary assembly.

Alternative nucleotide sequence modification methods are available for producing polypeptide variants for high throughput screening, for instance methods which involve homologous cross-over such as disclosed in U.S. Pat. No. 5,093,257, and methods which involve gene shuffling, i.e. recombination between two or more homologous nucleotide sequences resulting in new nucleotide sequences having a number of nucleotide alterations when compared to the starting nucleotide sequences. Gene shuffling (also known as DNA shuffling) involves one or more cycles of random fragmentation and reassembly of the nucleotide sequences, followed by screening to select nucleotide sequences encoding polypeptides with desired properties. In order for homology-based nucleic acid shuffling to take place, the relevant parts of the nucleotide sequences are preferably at least 50% identical, such as at least 60% identical, more preferably at least 70% identical, such as at least 80% identical. The recombination can be performed in vitro or in vivo.

Examples of suitable in vitro gene shuffling methods are disclosed by Stemmer et al. (1994), Proc. Natl. Acad. Sci. USA; vol. 91, pp. 10747-10751; Stemmer (1994), Nature, vol. 370, pp. 389-391; Smith (1994), Nature vol. 370, pp. 324-325; Zhao et al., Nat. Biotechnol. 1998, March; 16(3): 258-61; Zhao H. and Arnold, FB, Nucleic Acids Research, 1997, Vol. 25. No. 6 pp. 1307-1308; Shao et al., Nucleic Acids Research 1998, Jan. 15; 26(2): pp. 681-83; and WO 95/17413. An example of a suitable in vivo shuffling method is disclosed in WO 97/07205. Other techniques for mutagenesis of nucleic acid sequences by in vitro or in vivo recombination are disclosed e.g. in WO 97/20078 and U.S. Pat. No. 5,837,458. Examples of specific shuffling techniques include "family shuffling", "synthetic shuffling" and "in silico shuffling". Family shuffling involves subjecting a family of homologous genes from different species to one or more cycles of shuffling and subsequent screening or selection. Family shuffling techniques are disclosed e.g. by Crameri et al. (1998), Nature, vol. 391, pp. 288-291; Christians et al. (1999), Nature Biotechnology, vol. 17, pp. 259-264; Chang et al. (1999), Nature Biotechnology, vol. 17, pp. 793-797; and Ness et al. (1999), Nature Biotechnology, vol. 17, 893-896. Synthetic shuffling involves providing libraries of overlapping synthetic oligonucleotides based e.g. on a sequence alignment of homologous genes of interest. The synthetically generated oligonucleotides are recombined, and the resulting recombinant nucleic acid sequences are screened and if desired used for further shuffling cycles. Synthetic shuffling techniques are disclosed in WO 00/42561. In silico shuffling refers to a DNA shuffling procedure which is performed or modelled using a computer system, thereby partly or entirely avoiding the need for physically manipulating nucleic acids. Techniques for in silico shuffling are disclosed in WO 00/42560.

Once assembled (by synthesis, site-directed mutagenesis or another method), the nucleotide sequence encoding the polypeptide is inserted into a recombinant vector and operably linked to control sequences necessary for expression of the G-CSF in the desired transformed host cell.

It should of course be understood that not all vectors and expression control sequences function equally well to express the nucleotide sequence encoding a polypeptide described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts include, for example, vectors comprising expression control sequences from SV40, bovine papilloma virus, adenovirus and cytomegalovirus. Specific vectors are, e.g., pCDNA3.1 (+)\Hyg (Invitrogen, Carlsbad, Calif., USA) and pCI-neo (Stratagene, La Jolla, Calif., USA). Useful expression vectors for yeast cells include the 2µ plasmid and derivatives thereof, the POT1 vector (U.S. Pat. No. 4,931,373), the pJSO37 vector described in Okkels, Ann. New York Acad. Sci. 782, 202-207, 1996, and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685-98 (1986), pBluebac 4.5 and pMelbac (both available from Invitrogen). Useful expression vectors for bacterial hosts include known bacterial plasmids, such as plasmids from *E. coli*, including pBR322, pET3a and pET12a (both from Novagen Inc., WI, USA), wider host range plasmids, such as RP4, phage DNAs, e.g. the numerous derivatives of phage lambda, e.g. NM989, and other DNA phages, such as M13 and filamentous single stranded DNA phages.

Other vectors for use in this invention include those that allow the nucleotide sequence encoding the polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) and glutamine synthetase ("GS") amplification (see, e.g., U.S. Pat. No. 5,122,464 and EP 338, 841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1-3 and origin of replication.

The vector may also comprise a selectable marker, e.g. a gene whose product complements a defect in the host cell, such as the gene coding for dihydrofolate reductase (DHFR) or the Schizosaccharomyces pombe TPI gene (described by P. R. Russell, Gene 40, 1985, pp. 125-130), or one which confers resistance to a drug, e.g. ampicillin, kanamycin, tetracyclin, chioramphenicol, neomycin, hygromycin or methotrexate. For *Saccharoinyces cerevisiae*, selectable markers include ura3 and leu2. For filamentous fungi, selectable markers include amdS, pyrG, arcB, niaD and sC.

The term "control sequences" is defined herein to include all components which are necessary or advantageous for the expression of the polypeptide of the invention. Each control sequence may be native or foreign to the nucleic acid sequence encoding the polypeptide. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. *J Mol Biol* 1987 Aug. 20; 196(4):947-50).

In order to improve expression in mammalian cells a synthetic intron may be inserted in the 5' untranslated region of the nucleotide sequence encoding the polypeptide. An example of a synthetic intron is the synthetic intron from the plasmid pCI-Neo (available from Promega Corporation, WI, USA).

Examples of suitable control sequences for directing transcription in insect cells include the polyhedrin promoter, the P10 promoter, the *Autographa californiica* polyhedrosis virus basic protein promoter, the baculovirus immediate early gene 1 promoter, the baculovirus 39K delayed-early gene promoter, and the SV40 polyadenylation sequence. Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter, and the inducible GAL promoter. Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhiromucor miehei* aspartic proteinase or lipase, the TPI1 terminator and the ADH3 terminator. Examples of suitable control sequences for use in bacterial host cells include promoters of the lac system, the tip system, the TAC or TRC system, and the major promoter regions of phage lambda.

The presence or absence of a signal peptide will, e.g., depend on the expression host cell used for the production of the polypeptide to be expressed (whether it is an intracellular or extracellular polypeptide) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the *Lepidopteran manduca* sexta adipokinetic hormone precursor, (cf. U.S. Pat. No. 5,023,328), the honeybee melittin (Invitrogen), ecdysteroid UDPglucosyltransferase (egt) (Murphy et al., Protein Expression and Purification 4, 349-357 (1993) or human pancreatic lipase (hpl) (Methods in Enzymology 284, pp. 262-272, 1997). A preferred signal peptide for use in mammalian cells is that of hG-CSF or the murine Ig kappa light chain signal peptide (Coloma, M (1992) J. Imm Methods 152:89-104). For use in yeast cells suitable signal peptides have been found to be the α-factor signal peptide from *S. cereviciae* (cf. U.S. Pat. No. 4,870,008), a modified carboxypeptidase signal peptide (cf. L. A. Valls et al., Cell 48, 1987, pp. 887-897), the yeast BAR1 signal peptide (cf. WO 87/02670), the yeast aspartic protease 3 (YAP3) signal peptide (cf. M. Egel-Mitani et al., Yeast 6, 1990, pp. 127-137), and the synthetic leader sequence TA57 (WO98/32867). For use in *E. coli* cells a suitable signal peptide has been found to be the signal peptide ompA.

The nucleotide sequence of the invention encoding a polypeptide exhibiting G-CSF activity, whether prepared by site-directed mutagenesis, synthesis, PCR or other methods, may optionally also include a nucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with hG-CSF) or heterologous (i.e. originating from another source than hG-CSF) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

Any suitable host may be used to produce the polypeptide or polypeptide part of the conjugate of the invention, including bacteria, fungi (including yeasts), plant, insect, mammal, or other appropriate animal cells or cell lines, as well as transgenic animals or plants. Examples of bacterial host cells include gram-positive bacteria such as strains of *Bacillus*, e.g. *B. brevis* or *B. subtilis*, or *Streptomnyces*, or gram-negative bacteria, such as strains of *E. coli* or *Pseudomzonas*. The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278). Examples of suitable filamentous fungal host cells include strains of *Aspergillis*, e.g. *A. oryzae*, *A. niger*, or *A. nidulans*, *Fusarium* or *Trichoderina*. Fungal cells may be transformed by a process involving protoplast formation, transformation of the protoplasts, and regeneration of the cell wall in a manner known per se. Suitable procedures for transformation of *Aspeigillus* host cells are described in EP 238 023 and U.S. Pat. No. 5,679,543. Suitable methods for transforming *Fusariurn* species are described by Malardier et al., 1989, *Gene* 78: 147-156 and WO 96/00787. Examples of suitable yeast host cells include strains of *Saccharomyces*, e.g. *S. cerevisiae*, *Schizosaccharomyces*, *Klyveromyces*, *Pichia*, such as *P. pastoris* or *P. methanolica*, *Hansenula*, such as *H. polymorpha* or *Yarrowia*. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; Hinnen et al., 1978, *Proceedings of the National Academy of Sciences USA* 75: 1920: and as disclosed by Clontech Laboratories, Inc, Palo Alto, Calif., USA (in the product protocol for the Yeastmaker™ Yeast Transformation System Kit). Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Transformation of insect cells and production of heterologous polypeptides therein may be performed as described by Invitrogen. Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Methods for introducing exogeneous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells is conducted according to established methods, e.g. as disclosed in (Animal Cell Biotechnology, Methods and Protocols, Edited by Nigel Jenkins, 1999, Human Press Inc, Totowa, N.J., USA and Harrison M A and Rae I F, General Techniques of Cell Culture, Cambridge University Press 1997).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered by methods known in the art. For example, the polypeptide may be recovered from the nutrient medium by conventional procedures including, but not limited to, centrifugation, filtration, extraction, spray drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989). Specific methods for purifying polypeptides exhibiting G-CSF activity are described by D. Metcalf and N. A. Nicola in *The hemopoietic colony-stimulating factors*, p. 50-51, Cambridge University Press (1995), by C. S. Bae et al, Appl. Microbiol. Biotechnol, 52:338-344 (1999) and in U.S. Pat. No. 4,810,643.

Pharmaceutical Composition of the Invention and its Use

In a further aspect, the present invention comprises a composition comprising a polypeptide or conjugate as described herein and at least one pharmaceutically acceptable carrier or excipient.

The polypeptide, the conjugate or the pharmaceutical composition according to the invention may be used for the manufacture of a medicament for treatment of diseases, in particular prevention of infection in cancer patients undergoing certain types of chemotherapy, radiation therapy and bone marrow transplantations, mobilisation of progenitor cells for collection in peripheral blood progenitor cell transplantations, treatment of severe chronic or relative leukopenia, treatment of patients with acute myeloid leukaemia, treatment of AIDS or other immunodeficiency diseases, and for antifungal therapy, in particular for treatment of systemic or invasive candidiasis.

In another aspect the polypeptide, the conjugate or the pharmaceutical composition according to the invention is used in a method of treating a mammal having a general haematopoietic disorder, including those arising from radiation therapy or from chemotherapy, in particular neutropenia or leukopenia, AIDS or other immunodeficiency diseases, comprising administering to a mammal in need thereof such a polypeptide, conjugate or pharmaceutical composition. In particular, the method is aimed at increasing the level of neutrophils in a patient suffering from an insufficient neutrophil level, for example due to chemotherapy, radiation therapy, or HIV or another viral infection.

The polypeptides and conjugates of the invention will be administered to patients in a "therapeutically effective" dose, i.e. a dose that is sufficient to produced the desired effects in relation to the condition for which it is administered. The exact dose will depend on the disorder to be treated, and will be ascertainable by one skilled in the art using known techniques. The polypeptides or conjugates of the invention may e.g. be administered at a dose similar to that employed in therapy with rhG-CSF such as Neupogen®. A suitable dose of a conjugate of the invention is contemplated to be in the range of about 5-300 microgram/kg body weight (based on the weight of the protein part of the conjugate), e.g. 10-200 microgram/kg, such as 25-100 microgram/kg. It will be apparent to those of skill in the art that an effective amount of a polypeptide, conjugate or composition of the invention depends, inter alia, upon the disease, the dose, the administration schedule, whether the polypeptide or conjugate or composition is administered alone or in conjunction with other therapeutic agents, the serum half-life of the compositions, the general health of the patient, and the frequency of administration. Preferably, the polypeptide, conjugate, preparation or composition of the invention is administered in an effective dose, in particular a dose which is sufficient to normalize the number of leukocytes, in particular neutrophils, in the patient in question. Normalization of the number of leukocytes may be determined by simply counting the number of leukocytes at regular intervals in accordance with established practice.

The polypeptide or conjugate of the invention is preferably administered in a composition including one or more pharmaceutically acceptable carriers or excipients. The polypeptide or conjugate can be formulated into pharmaceutical compositions in a manner known per se in the art to result in a polypeptide pharmaceutical that is sufficiently storage-stable and is suitable for administration to humans or animals. The pharmaceutical composition may be formulated in a variety of forms, including as a liquid or gel, or lyophilized, or any other suitable form. The preferred form will depend upon the particular indication being treated and will be apparent to one of skill in the art.

Accordingly, this invention provides compositions and methods for treating various forms of leukopenia or neutropenia. In particular the polypeptide, conjugate or composition of the invention may be used to prevent infection in cancer patients undergoing certain types of radiation therapy chemotherapy and bone marrow transplantations, to mobilize progenitor cells for collection in peripheral blood progenitor cell transplantations, for treatment of severe chronic or relative leukopenia and to support treatment of patients with acute myeloid leukaemia. Additionally, the polypeptide, conjugate or composition of the invention may be used for treatment of AIDS or other immunodeficiency diseases and for antifungal therapy, in particular for treament of systemic or invasive candidiasis, and for the treatment of bacterial infections.

Since the polypeptide conjugates of the invention have a long in vivo half-life and have been found to reduce the duration of neutropenia and leukopenia by administration of a single dose, in contrast to hG-CSF which must be administered daily, the conjugates of the invention are well-suited for administration e.g. on a weekly basis for the prevention and/or treatment of neutropenia. In one embodiment, the polypeptide conjugate or pharmaceutical composition of the invention is for the prevention and/or treatment of neutropenia due to chemotherapy. In the case of chemotherapy administered at intervals, e.g. on a weekly basis by intravenous injection or by another type of injection, such as subcutaneous or intramuscular injection, it will normally be sufficient to administer the conjugate of the invention in a single dose per chemotherapy treatment, i.e. given either before, after or simultaneously with the chemotherapy. In other cases where the chemotherapy is administered differently, for example orally on a daily basis or over an extended period of time by means of an infusion pump, the conjugates of the invention may be administered in a similar manner, e.g. once a week, or, in the case of chemotherapy sessions given less frequently than once a week, once per session.

Drug form

The polypeptide or conjugate of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

Excipients

"Pharmaceutically acceptable" means a carrier or excipient that at the dosages and concentrations employed does not cause any untoward effects in the patients to whom it is administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

Mix of Drugs

The pharmaceutical composition of the invention may be administered alone or in conjunction with other therapeutic agents. These agents may be incorporated as part of the same pharmaceutical composition or may be administered separately from the polypeptide or conjugate of the invention, either concurrently or in accordance with another treatment schedule. In addition, the polypeptide, conjugate or pharmaceutical composition of the invention may be used as an adjuvant to other therapies.

Patients

A "patient" for the purposes of the present invention includes both humans and other mammals. Thus the methods are applicable to both human therapy and veterinary applications.

Administration Route

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art. Typically, the formulation will designed for parenteral administration, e.g. by the subcutaneous route.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, omithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

Sustained Release Preparations

Suitable examples of sustained-release preparations include semi-permeable s5 matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-

(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

All references cited herein are hereby incorporated by reference in their entirety for all purposes.

The invention is further described in the non-limiting examples below.

SEQUENCE LISTING

Figure 1:
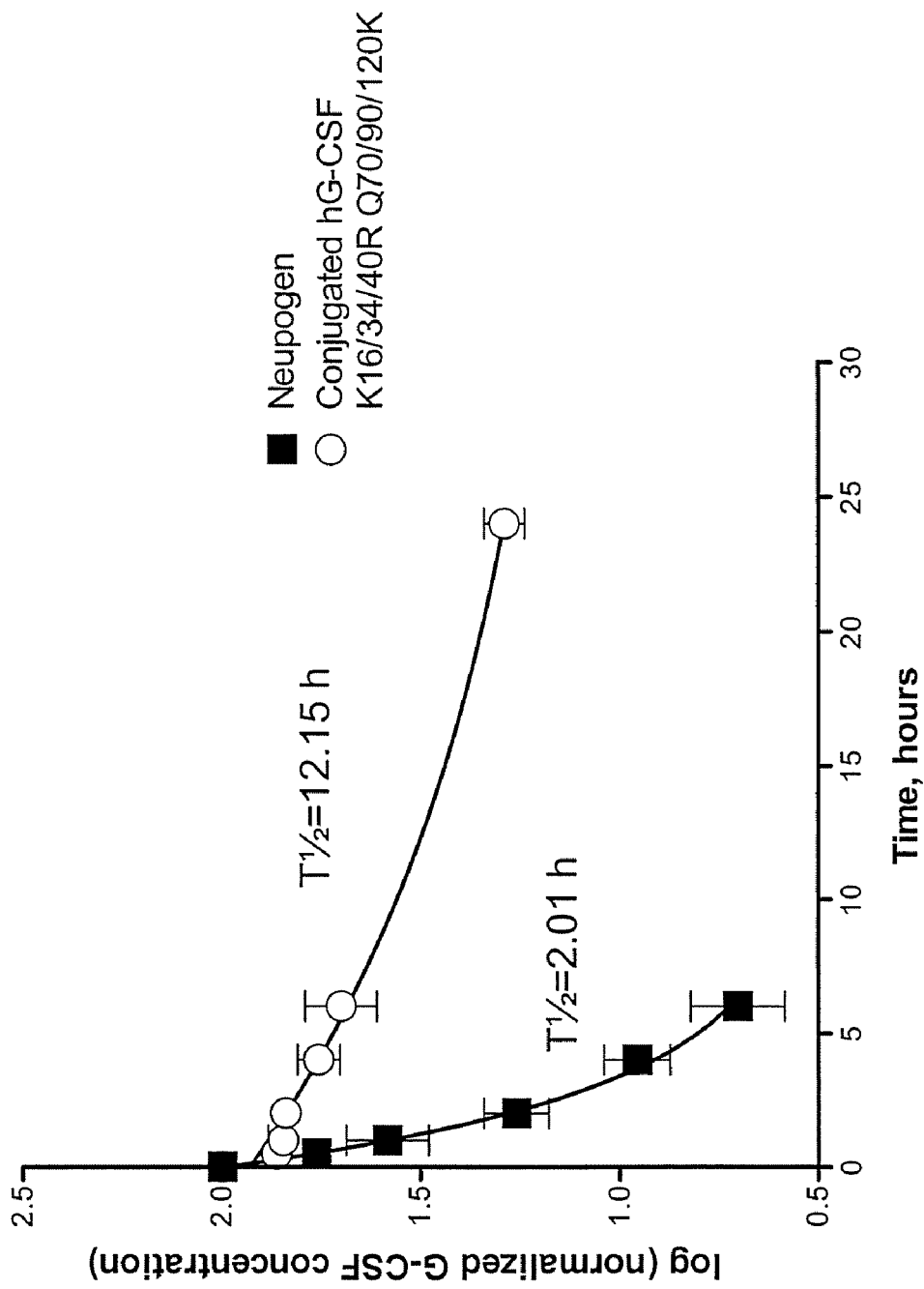
FIG. 1: The in vivo half-lives of rhG-CSF (Neupogen®) and SPA-PEG 5000-conjugated hG-CSF K16R K34R K40R Q70K Q90K Q120K

The appended sequence listing contains the following sequences:

SEQ ID NO:1: The amino acid sequence of human G-CSF.
SEQ ID NO:2: A synthetic DNA sequence encoding human G-CSF, with codon usage optimized for expression in *E. coli*.
SEQ ID NO:3: The amino acid sequence of the OmpA signal sequence.
SEQ ID NO:4: A synthetic DNA sequence encoding the OmpA signal sequence.
SEQ ID NO:5: A synthetic histidine tag.
SEQ ID NO:6: A synthetic DNA sequence encoding the histidine tag of SEQ ID NO:5.
SEQ ID NO:7: The amino acid sequence of a human G-CSF signal peptide.
SEQ ID NO:8: A synthetic DNA sequence encoding human G-CSF, including the signal peptide of SEQ ID NO:7, with codon usage optimized for expression in CHO cells.
SEQ ID NO:9-15: Various synthetic tags Materials and Methods Methods Used to Determine the Amino Acids to be Modified Accessible Surface Area (ASA)

A 3D ensemble of 10 structures determined by NMR spectroscopy (Zink et al. (1994) Biochemistry 33: 8453-8463) is available from the Protein Data Bank (PDB) (www.rcsb.org/pdb/). This information can be entered into the computer program Access (B. Lee and F. M. Richards, J. Mol. Biol. 55: 379-400 (1971)) version 2 (© 1983 Yale University) and used to compute the accessible surface area (ASA) of the individual atoms in the structure. This method typically uses a probe size of 1.4Å and defines the Accessible Surface Area (ASA) as the area formed by the centre of the probe. Prior to this calculation all water molecules and all hydrogen atoms should be removed from the coordinate set as should other atoms not directly related to the protein.

Fractional ASA of Side Chain

The fractional ASA of the side chain atoms is computed by division of the sum of the ASA of the atoms in the side chain with a value representing the ASA of the side chain atoms of that residue type in an extended ALA-x-ALA tripeptide. See Hubbard, Campbell & Thornton (1991) J. Mol. Biol. 220, 507-530. For this example the CA atom is regarded as a part of the side chain of glycine residues but not for the remaining residues. The values in the following table are used as standard 100% ASA for the side chain:

| | |
|---|---|
| Ala | 69.23 Å$^2$ |
| Arg | 200.35 Å$^2$ |
| Asn | 106.25 Å$^2$ |

-continued

| | |
|---|---|
| Asp | 102.06 Å² |
| Cys | 96.69 Å² |
| Gln | 140.58 Å² |
| Glu | 134.61 Å² |
| Gly | 32.28 Å² |
| His | 147.00 Å² |
| Ile | 137.91 Å² |
| Leu | 140.76 Å² |
| Lys | 162.50 Å² |
| Met | 156.08 Å² |
| Phe | 163.90 Å² |
| Pro | 119.65 Å² |
| Ser | 78.16 Å² |
| Thr | 101.67 Å² |
| Trp | 210.89 Å² |
| Tyr | 176.61 Å² |
| Val | 114.14 Å² |

Residues not detected in the structure are defined as having 100% exposure as they are thought to reside in flexible regions.

Determining Distances Between Atoms:

The distance between atoms is most easily determined using molecular graphics software, e.g. InsightII® v. 98.0, MSI INC.

General Considerations Regarding Amino Acid Residues to be Modified

As explained above, amino acid residues to be modified in accordance with the present invention are preferably those whose side chains are surface exposed, in particular those with more than about 25% of the side chain exposed at the surface of the molecule, and more preferably those with more than 50% side chain exposure. Another consideration is that residues located Methods for PEGylation of hG-CSF and Variants Thereof PEGylation of hG-CSF and Variants Thereof in Solution Human G-CSF and variants thereof are PEGylated at a concentration of 250 µg/ml in 50 mM sodium phosphate, 100 mM NaCl, pH 8.5. The molar surplus of PEG is 50-100 times with respect to PEGylation sites on the protein. The reaction mixture is placed in a thermo mixer for 30 minutes at 37° C. at 1200 rpm. After 30 minutes, quenching of the reaction is obtained by adding a molar excess of glycine.

Cation exchange chromatography is applied to remove excess PEG, glycine and other by-products from the reaction mixture. The PEGylation reaction mixture is diluted with 20 mM sodium citrate pH 2.5 until the ionic strength is less than 7 mS/cm. pH is adjusted to 2.5 using 5 N HCl. The mixture is applied to a SP-sepharose FF column equilibrated with 20 mM sodium citrate pH 2.5. Unbound material is washed off the column using 4 column volumes of equilibration buffer. PEGylated protein is eluted in three column volumes by adding 20 mM sodium citrate, 750 mM sodium chloride. Pure PEGylated G-CSF is concentrated and buffer exchange is performed using VivaSpin concentration devices, molecular weight cut-off (mwco): 10 kDa.

PEGylation in Microtiter Plates of a Tagged Polypeptide with G-CSF Activity

A polypeptide exhibiting G-CSF activity is expressed with a suitable tag, e.g. any of the tags exemplified in the general description above, and culture broth is transferred to one or more wells of a microtiter plate capable of immobilising the tagged polypeptide. When the tag is Met-Lys-His-Gln-His-Gln-His-Gln-His-Gln-His-Gln-His-Gln-Gln (SEQ ID NO:5), a nickel-nitrilotriacetic acid (Ni-NTA) HisSorb microtiter plate commercially available from QIAGEN can be used.

After immobilization of the tagged polypeptide to the microtiter plate, the wells are washed in a buffer suitable for binding and subsequent PEGylation followed by incubating the wells with the activated PEG of choice. As an example, M-SPA-5000 from Shearwater Corp. is used. The molar ratio of activated PEG to polypeptide should be optimized, but will typically be greater than 10:1, e.g. up to about 100:1 or higher. After a suitable reaction time at ambient temperature, typically around 1 hour, the reaction is stopped by removal of the activated PEG solution. The conjugated protein is eluted from the plate by incubation with a suitable buffer. Suitable elution buffers may contain imidazole, excess NTA or another chelating compound. The conjugated protein is assayed for biological activity and immunogenicity as appropriate. The tag may optionally be cleaved off using a method known in the art, e.g. using diaminopeptidase the Gln in pos-1 can be converted to pyroglutamyl with GCT (glutamylcyclotransferase) and finally cleaved off with PGAP (pyro-glutamyl-aminopeptidase), giving the untagged protein. The process involves several steps of metal chelate affinity chromatography. Alternatively, the tagged polypeptide may be conjugated.

PEGylation of a Polypeptide Exhibiting hG-CSF Activity and having a Blocked Receptor-Binding Site In order to optimize PEGylation of hG-CSF in a manner excluding PEGylation of lysines involved in receptor recognition, the following method has been developed:

Purified hG-CSF is obtained as described in Example 4. A homodimer complex consisting of an hG-CSF polypeptide and the soluble domain of the G-CSF receptor in a 2:2 stochiometry is formed in a phosphate-buffered saline solution (PBS) buffer at pH 7. The concentration of hG-CSF polypeptide is approximately 20 µg/ml or 1 µM and the receptor is present at an equimolar concentration.

M-SPA-5000 from Shearwater Corp. is added at 3 different concentration levels corresponding to a 10, 25 and 50 molar excess to the number of attachment sites in hG-CSF polypeptide. The reaction time is 30 min at room temperature. After the 30 min reaction period, the pH of the reaction mixture is adjusted to pH 2.0 and the reaction mixture is applied to a Vydac C18 column and eluted with an acetonitrile gradient essentially as described (Utsumi et al., J. Biochem., Vol. 101, 1199-1208, (1987). Alternatively, an isopropanol gradient can be used.

Fractions are analyzed using the primary screening assay described herein and active PEGylated hG-CSF polypeptide obtained by this method is stored at −80° C. in PBS, pH 7 containing 1 mg/ml human serum albumin (HSA).

Methods Used to Characterize Conjugated and Non-Conjugated hG-CSF and Variants Thereof.

Determination of the Molecular Size of hG-CSF and Variants Thereof.

The molecular weight of conjugated or non-conjugated hG-CSF or variants thereof is determined by either SDS-PAGE, gel filtration, matrix assisted laser desorption mass spectrometry or equilibrium centrifugation. As explained above, SDS-PAGE provides information on the "apparent molecular weight". The actual molecular weight can advantageously be determined using mass spectrometry. SDS-PAGE is carried out using the NuPAGE® kit (Novex high-performance pre-cast gels) from Invitrogen™. 15 µl of the samples are loaded onto NuPAGE 4-12% Bis-Tris gels (Cat. Nr. NPO321) and eluted in NuPAGE MES SDS running buffer (Cat. Nr. NPO002-02) for 35 minutes at 200 V and 120 mA.

Determination of Polypeptide Concentration

The concentration of a polypeptide can be measured using optical density measurements at 280 nm, an enzyme-linked immunoadsorption assay (ELISA), a radio-immunoassay (RIA), or other such immunodetection techniques well known in the art. Furthermore, the polypeptide concentration in a sample can be measured with the Biacore® instrument using a Biacore® chip coated with an antibody specific for the polypeptide.

Such an antibody can be coupled covalently to the Biacore® chip by various chemistries. Alternatively, the antibody can be bound non-covalently e.g. by means of an antibody specific for the Fc portion of the anti-polypeptide antibody. The Fc specific antibody is first coupled covalently to the chip. The anti-polypeptide antibody is then flowed over the chip and is bound by the first antibody in a directed fashion. Furthermore, biotinylated antibodies can be immobilized using a streptavidin coated surface (e.g. Biacore Sensor Chip SA®) (Real-Time Analysis of Biomolecular Interactions, Nagata and Handa (Eds.), 2000, Springer Verlag, Tokyo; Biacore 2000 Instrument Handbook, 1999, Biacore AB).

When the sample is flowed over the chip the polypeptide will bind to the coated antibody and the increase in mass can be measured. By using a preparation of the polypeptide in a known concentration, a standard curve can be established and subsequently the concentration of the polypeptide in the sample can be determined. After each injection of sample the sensor chip is regenerated by a suitable eluent (e.g. a low pH buffer) that removes the bound analyte.

Generally, the applied antibodies will be monoclonal antibodies raised against the wild type polypeptide. Introduction of mutations or other manipulations of the wild type polypeptide (extra glycosylations or polymer conjugations) may alter the recognition by such antibodies. Furthermore, such manipulations that give rise to an increased molecular weight of the polypeptide will result in an increased plasmon resonance signal. Consequently, it is necessary to establish a standard curve for every molecule to be tested.

Methods Used to Determine the In Vitro and In Vivo Activity of Conjugated and Non-Conjugated hG-CSF and Variants Thereof.

Primary Assay 1—In Vitro G-CSF Activity Assay

Proliferation of the murine cell line NFS-60 (obtained from Dr. J. me, St. Jude Children's Research Hospital, Tennessee, USA) is dependent on the presence of active G-SCF in the growth medium. Thus, the in vitro biological activity of hG-CSF and variants thereof can be determined by measuring the number of dividing NFS-60 cells after addition of a G-CSF sample to the growth medium followed by incubation over a fixed period of time.

NFS-60 cells are maintained in Iscoves DME Medium containing 10% w/w FBS (fetal bovine serum), 1% w/w Pen/Strep, 10 μg per litre hG-CSF and 2 mM Glutamax. Prior to sample addition, cells are washed twice in growth medium without hG-CSF and diluted to a concentration of $2.2 \times 10^5$ cells per ml. 100 μl of the cell suspension is added to each well of a 96 well microtiter plate (Corning).

Samples containing conjugated or non-conjugated G-CSF or variants thereof are diluted to concentrations between $1.1 \times 10^{-6}$ M and $1.1 \times 10^{-13}$ M in the growth medium. 10 μl of each sample is added to 3 wells containing NFS-60 cells. A control consisting of 10 μl of mammalian growth medium is added to 8 wells on each microtiter plate. The cells are incubated for 48 hours (37° C., 5% $CO_2$) and the number of dividing cells in each well is quantified using the WST-1 cell proliferation agent (Roche Diagnostics GmbH, Mannheim, Germany). 0.01 ml WST-1 is added to the wells followed by incubation for 150 min. at 37° C. in a 5% $CO_2$ air atmosphere. The cleavage of the tetrazolium salt WST-1 by mitochondrial dehydrogenases in viable cells results in the formation of formazan that is quantified by measuring the absorbance at 450 nm. Hereby, the number of viable cells in each well is quantified.

Based on these measurements, dose-response curves for each conjugated and non-conjugated G-CSF molecule or variants thereof are calculated, after which the EC50 value for each molecule can be determined. This value is equal to the amount of active G-CSF protein that is necessary to obtain 50% of the maximum proliferation activity of non-conjugated human G-CSF. Thus, the EC50 value is a direct measurement of the in vitro activity of the given protein, a lower EC50 value indicating a higher activity.

Primary Assay 2—In Vitro G-CSF Activity Assay

The murine hematopoietic cell line BaF3 is transfected with a plasmid carrying the human G-CSF receptor and the promoter of the transcription regulator, fos, in front of the luciferase reporter gene. Upon stimulation of such a cell line with a G-CSF sample, a number of intracellular reactions lead to stimulation of fos expression, and consequently to expression of luciferase. This stimulation is monitored by the Steady-Glo™ Luciferase Assay System (Promega, Cat. No. E2510) whereby the in vitro activity of the G-CSF sample may be quantified.

BaF3/hGCSF-R/pfos-lux cells are maintained at 37° C. in a humidified 5% $CO_2$ atmosphere in complete culture media (RPMI-1640/HEPES (Gibco/BRL, Cat. No. 22400), 10% FBS (HyClone, characterized), 1× Penicillin/Streptomycin (Gibco/BRL, Cat. No. 15140-122), 1× L-Glutamine (Gibco/BRL, Cat. No. 25030-081), 10% WEHI-3 conditioned media (source of muIL-3), and grown to a density of $5 \times 10^5$ cells/mL (confluent). The cells are reseeded at about $2 \times 10^4$ cells/mL every 2-3 days.

One day prior to the assay, log-phase cells are resuspended at $2 \times 10^5$ cells/mL in starving media (DMEMIF-12 (Gibco/BRL, Cat. No. 11039), 1% BSA (Sigma, Cat. No. A3675), 1× Penicillin/Streptomycin (Gibco/BRL, Cat. No. 15140-122), 1× L-Glutamine (Gibco/BRL, Cat. No. 25030-081), 0.1% WEHI-3 conditioned media) and starved for 20 hours. The cells are washed twice with PBS and tested for viability using Trypan Blue viability staining. The cells are resuspended in assay media (RPMI-1640 (phenol-red free, Gibco/BRL, Cat. No. 11835), 25 mM HEPES, 1% BSA (Sigma, Cat. No. A3675), 1× Penicillin/Streptomycin (Gibco/BRL, Cat. No. 15140-122), 1× L-Glutamine (Gibco/BRL, Cat. No. 25030-081) at $4 \times 10^6$ cells/mL, and 50 μL are aliquotted into each well of a 96-well microtiter plate (Corning). Samples containing conjugated or non-conjugated G-CSF or variants thereof are diluted to concentrations between $1.1 \times 10^{-7}$ M and $1.1 \times 10^{-12}$ M in the assay medium. 50 μl of each sample is added to 3 wells containing BaF3/hGCSF-R/pfos-lux cells. A negative control consisting of 50 μl of medium is added to 8 wells on each microtiter plate. The plates are mixed gently and incubated for 2 hours at 37° C. The luciferase activity is measured by following the Promega Steady-Glo™ protocol (Promega Steady-Glo™ Luciferase Assay System, Cat. No. E2510). 100 μL of substrate is added per well followed by gentle mixing. Luminescence is measured on a TopCount luminometer (Packard) in SPC (single photon counting) mode.

Based on these measurements, dose-response curves for each conjugated and non-conjugated G-CSF molecule or variants thereof are calculated, after which the EC50 value for each molecule can be determined.

Secondary Assay—Binding Affinity of G-CSF or Variants Thereof to the hG-CSF Receptor Binding of rhG-CSF or variants thereof to the hG-CSF receptor is studied using standard binding assays. The receptors may be purified extracellular receptor domains, receptors bound to purified cellular plasma membranes, or whole cells—the cellular sources being either cell lines that inherently express G-CSF receptors (e.g. NFS-60) or cells transfected with cDNAs encoding the receptors. The ability of rhG-CSF or variants thereof to compete for the binding sites with native G-CSF is analyzed by incubating with a labeled G-CSF-analog, for instance biotinylated hG-CSF or radioiodinated hG-CSF. An example of such an assay is described by Yamasaki et al. (Drugs. Exptl. Clin. Res. 24:191-196 (1998)).

The extracellular domains of the hG-CSF receptor can optionally be coupled to Fc and immobilized in 96 well plates. RhG-CSF or variants thereof are subsequently added and the binding of these is detected using either specific anti-hG-CSF antibodies or biotinylated or radioiodinated hG-CSF.

Measurement of the In Vivo Half-Life of Conjugated and Non-Conjugated rhG-CSF and Variants Thereof.

An important aspect of the invention is the prolonged biological half-life that is obtained by construction of a hG-CSF with or without conjugation of the polypeptide to the polymer moiety. The rapid decrease of hG-CSF serum concentrations has made it important to evaluate biological responses to treatment with conjugated and non-conjugated hG-CSF and variants thereof. Preferably, the conjugated and non-conjugated hG-CSF and variants thereof of the present invention have prolonged serum half-lives also after i.v. administration, making it possible to measure by e.g. an ELISA method or by the primary screening assay. Measurement of in vivo biological half-life was carried out as described below.

Male Sprague Dawley rats (7 weeks old) were used. On the day of administration, the weights of the animals were measured (280-310 gram per animal). 100 µg per kg body weight of the non-conjugated and conjugated hG-CSF samples were each injected intravenously into the tail vein of three rats. At 1 minute, 30 minutes, 1, 2, 4, 6, and 24 hours after the injection, 500 µl of blood was withdrawn from the eyes of each rat while under $CO_2$-anaesthesia. The blood samples were stored at room temperature for 1 ½ hours followed by isolation of serum by centrifugation (4° C., 18000×g for 5 minutes). The serum samples were stored at −80° C. until the day of analysis. The amount of active G-CSF in the serum samples was quantified by the G-CSF in vitro activity assay (see primary assay 2) after thawing the samples on ice.

Another example of an assay for the measurement of in vivo half-life of G-CSF or variants thereof is described in U.S. Pat. No. 5,824,778, the content of which is hereby incorporated by reference.

Measurement of the In Vivo Biological Activity in Healthy Rats of Conjugated and Non-Conjugated hG-CSF and Variants Thereof.

Measurement of the in vivo biological effects of hG-CSF in SPF Sprague Dawley rats (purchased from M & B A/S, Denmark) is used to evaluate the biological efficacy of conjugated and non-conjugated G-CSF and variants thereof.

On the day of arrival the rats are randomly allocated into groups of 6. The animals are acclimatized for a period of 7 days wherein individuals in poor condition or at extreme weights are rejected. The weight range of the rats at the start of the acclimatization period is 250-270 g.

On the day of administration the rats are fasted for 16 hours followed by subcutaneous injection of 100 µg per kg body weight of hG-CSF or a variant thereof. Each hG-CSF sample is injected into a group of 6 randomized rats. Blood samples of 300 µl EDTA stabilized blood are drawn from a tail vein of the rats prior to dosing and at 6, 12, 24, 36, 48, 72, 96, 120 and 144 hours after dosing. The blood samples are analyzed for the following haematological parameters: Haemoglobin, red blood cell count, haematocrit, mean cell volume, mean cell haemoglobin concentration, mean cell haemoglobin, white blood cell count, differential leucocyte count (neutrophils, lymphocytes, eosinophils, basophils, monocytes). On the basis of these measurements the biological efficacy of conjugated and non-conjugated hG-CSF and variants thereof is evaluated. Further examples of assays for the measurement of in vivo biological activity of hG-CSF or variants thereof are described in U.S. Pat. No. 5,681,720, U.S. Pat. No. 5,795,968, U.S. Pat. No. 5,824,778, U.S. Pat. No. 5,985,265 and by Bowen et al., Experimental Hematology 27:425-432 (1999).

Measurement of the In Vivo Biological Activity in Rats with Chemotherapy-Induced Neutropenia of Conjugated and Non-Conjugated hG-CSF and Variants Thereof SPF Sprague Dawley rats were purchased from M & B A/S, Denmark. On the day of arrival the rats are randomly allocated into groups of 6. The animals are acclimatized for a period of 7 days wherein individuals in poor condition or at extreme weights are rejected. The weight range of the rats at the start of the acclimatization period is 250-270 g.

24 hours before administration of the hG-CSF samples the rats are injected i.p. with 50 or 90 mg per kg body weight of cyclophosphamide (CPA). The PEGylated hG-CSF variants are given as a single dose injected s.c. at day 0, while non-conjugated hG-CSF is injected s.c. either in a single dose at day 0 or on a daily basis. For hG-CSF or variants given in a single dose at day 0, the dosage is 100 µg per kg body weight. For non-conjugated hG-CSF (Neupogen®) given on a daily basis, the dosage varied and is given in the examples below. Each hG-CSF sample is injected into a group of 6 randomized rats. Blood samples of 300 µl EDTA stabilized blood are drawn from a tail vein of the rats prior to dosing and at 6, 12, 24, 36, 48, 72, 96, 120, 144 and 168 hours after dosing. The blood samples are analyzed for the following haematological parameters: hemoglobin, red blood cell count, haematocrit, mean cell volume, mean cell haemoglobin concentration, mean cell haemoglobin, white blood cell count, differential leucocyte count (neutrophils, lymphocytes, eosinophils, basophils, monocytes). On the basis of these measurements the biological efficacy of conjugated and non-conjugated hG-CSF and variants thereof is evaluated.

Determination of Polypeptide Receptor-Binding Affinity (On- and Off-Rate)

The strength of the binding between a receptor and ligand can be measured using an enzyme-linked immunoadsorption assay (ELISA), a radio-immunoassay (RIA), or other such immunodetection techniques well known in the art. The ligand-receptor binding interaction may also be measured with the Biacore® instrument, which exploits plasmon resonance detection (Zhou et al., Biochemistry, 1993, 32, 8193-98; Faegerstram and O'Shannessy, 1993, In Handbook of Affinity Chromatography, 229-52, Marcel Dekker, Inc., NY).

The Biacore® technology allows one to bind receptor to a gold surface and to flow ligand over it. Plasmon resonance detection gives direct quantification of the amount of mass bound to the surface in real time. This technique yields both on- and off-rate constants and thus a ligand-receptor dissociation constant and an affinity constant can be directly determined.

In Vitro Immunogenicity Test of hG-CSF Conjugates

The reduced immunogenicity of a conjugate of the invention can be determined by use of an ELISA method measuring the immunoreactivity of the conjugate relative to a reference molecule or preparation. The reference molecule or preparation is normally a recombinant human G-CSF preparation such as Neupogen® or another recombinant human G-CSF preparation, e.g. an N-terminally PEGylated rhG-CSF molecule as described in U.S. Pat. No. 5,824,784. The ELISA method is based on antibodies from patients treated with one of these recombinant G-CSF preparations. The immunogenicity is considered to be reduced when the conjugate of the invention has a statistically significant lower response in the assay than the reference molecule or preparation.

Neutralisation of activity in G-CSF Bioassay

The neutralisation of hG-CSF conjugates by anti-G-CSF sera is analyzed using the G-CSF bioassay described above.

Sera from patients treated with the G-CSF reference molecule or from immunized animals are used. Sera are added either in a fixed concentration (dilution 1:20-1:500 (pt sera) or 20-1000 ng/ml (animal sera)) or in five-fold serial dilutions of sera starting at 1:20 (pt sera) or 1000 ng/ml (animal sera). HG-CSF conjugate is added either in seven fold-dilutions starting at 10 nM or in a fixed concentration (1-100 pM) in a total volume of 80 µl DMEM medium +10% FCS. The sera are incubated for 1 hr. at 37° C. with hG-CSF conjugate.

The samples (0.01 ml) are then transferred to 96 well tissue culture plates containing NFS-60 cells in 0.1 ml DMEM media. The cultures are incubated for 48 hours at 37° C. in a 5% CO$_2$ air atmosphere. 0.01 ml WST-1 (WST-1 cell proliferation agent, Roche Diagnostics GmbH, Mannheim, Germany) is added to the cultures and incubated for 150 min. at 37° C. in a 5% CO$_2$ air atmosphere. The cleavage of the tetrazolium salt WST-1 by mitochondrial dehydrogenases in viable cells results in the formation of formazan that is quantified by measuring the absorbance at 450 nm.

When hG-CSF conjugate samples are titrated in the presence of a fixed amount of serum, the neutralising effect is defined as fold inhibition (FI) quantified as EC50 (with serum)/EC50 (without serum). The reduction of antibody neutralisation of G-CSF variant proteins is defined as $$\left(1 - \frac{(FI \ \text{variant} - 1)}{(FI \ \text{wt} - 1)}\right) \times 100\%$$

EXAMPLE 1

Construction and Cloning of Synthetic Genes Encoding hG-CSF

The following DNA fragments were synthesized following the general procedure described by Stemmer et al. (1995), *Gene* 164, pp. 49-53:

Fragment 1, consisting of a Bam HI digestion site, a sequence encoding the YAP3 signal peptide (WO 98/32867), a sequence encoding the TA57 leader sequence (WO 98/32867), a sequence encoding a KEX2 protease recognition site (AAAAGA), a sequence encoding hG-CSF with its codon usage optimized for expression in *E. coli*, (SEQ ID NO:2) and a Xba I digestion site.

Fragment 2, consisting of a Bam HI digestion site, a sequence encoding the YAP3 signal peptide (WO 98/32867), a sequence encoding the TA57 leader sequence (WO 98/32867), a sequence encoding a histidine tag (SEQ ID NO:5), a sequence encoding a KEX2 protease recognition site (AAAAGA), a sequence encoding hG-CSF with its codon usage optimized for expression in *E. coli*, (SEQ ID NO:2) and a Xba I digestion site.

Fragment 3, consisting of a Nde I digestion site, a sequence encoding the OmpA signal peptide (SEQ ID NO:3), a sequence encoding hG-CSF with its codon usage optimized for expression in *E. coli*, (SEQ ID NO:2) and a Bam HI digestion site.

Fragment 4, consisting of a Bam HI digestion site, the Kozak consensus sequence (Kozak, M. *J Mol Biol* 1987 Aug. 20; 196(4):947-50), a sequence encoding the hG-CSF signal peptide (SEQ ID NO:7) and hG-CSF with its codon usage optimized for expression in CHO cells (SEQ ID NO:8) and a Xba I digestion site.

DNA fragment 1 and 2 were inserted into the Bam HI and Xba I digestion sites in plasmid pJSO37 (Okkels, Ann. New York Acad. Sci. 782:202-207, 1996) using standard DNA techniques. This resulted in plasmids pG-CSFcerevisiae and pHISG-CSFcerevisiae.

DNA fragment 3 was inserted into the Nde I and Bam HI digestion sites in plasmid pET12a (Invitrogen) using standard DNA techniques. This resulted in plasmid pG-CSFcoli DNA fragment 4 was inserted into the Bam HI and Xba I digestion sites in plasmid pcDNA3.1 (+) (Invitrogen) using standard DNA techniques. This resulted in plasmid pG-CSFCHO.

EXAMPLE 2

Expression of hG-CSF in *S. cerevisiae* and *E. coli*

Transformation of *Saccharomyces cerevisiae* YNG318 (available from the American Type Culture Collection, Va., USA as ATCC 208973) with either plasmid pG-CSFcerevisiae or pHISG-CSFcerevisiae, isolation of transformants containing either of the two plasmids, and subsequent extracellular expression of hG-CSF without and with the HIS tag, respectively, was performed using standard techniques described in the literature. Transformation of *E. coli*BL21 (DE3) (Novagen, Cat. No. 69387-3) with pG-CSFcoli, isolation of transformants containing the plasmid and subsequent expression of hG-CSF in the supernatant and in the periplasm of the cell was performed as described in the pET System Manual (8$^{th}$ edition) from Novagen.

Expression of hG-CSF by *S. cerevisiae* and *E. coli* was verified by Western Blot analysis using the ImmunoPure Ultra-Sensitive ABC Rabbit IgG Staining kit (Pierce) and a polyclonal 1s antibody against hG-CSF (Pepro Tech EC Ltd.). It was observed that the protein had the correct size.

The expression levels of hG-CSF with and without the N-terminal histidine tag in *S. cerevisiae* and *E. coli* were quantified using a commercially available G-CSF specific ELISA kit (Quantikine Human G-CSF Immunoassay, R&D Systems Cat. No. DCS50). The measured values are listed below.

| Expression system | Expression level (mg G-CSF per L) |
| --- | --- |
| hG-CSF in *S. cerevisiae* | 30 |
| hG-CSF with histidine tag in *S. cerevisiae* | 25 |
| hG-CSF in *E. coli* | 0.05 |

EXAMPLE 3

Generation of a Stable CHO-K1 G-CSF Producer

The day before transfection the CHO K1 cell line (ATCC #CC1-61) is seeded in a T-25 flask in 5 ml DMEM/F-12 medium (Gibco # 31330-038) supplemented with 10% FBS and penicillin/streptomycin. The following day (at nearly 100% confluency) the transfection is prepared: 90 µl DMEM medium without supplements is aliquoted into a 14 ml polypropylene tube (Corning). 10 µl Fugene 6 (Roche) is added directly into the medium and incubated for 5 min at room temperature. In the meantime 5 µg plasmid pG-CSFCHO is aliquoted into another 14 ml polypropylene tube. After incubation the Fugene 6 mix is added directly to the DNA solution and incubated for 15 min at room temperature. After incubation the whole volume is added drop-wise to the cell medium.

The next day the medium is exchanged with fresh medium containing 360 µg/ml hygromycin (Gibco). Every day hereafter the selection medium is renewed until the primary transfection pool has reached 100% confluency. The primary transfection pool is sub-cloned by limited dilution (300 cells seeded in five 96-well plates).

EXAMPLE 4

Purification of hG-CSF and Variants Thereof from *S. cerevisiae* Culture Supernatants Purification of hG-CSF was performed as follows:

Cells are removed by centrifugation. Cell depleted supernatant is then filter sterilized through a 0.22 μm filter. Filter sterilized supernatant is diluted 5 fold in 10 mM sodium acetate pH 4.5. pH is adjusted by addition of 10 ml concentrated acetic acid per 5 liters of diluted supernatant. The ionic strength should be below 8 mS/cm before application to the cation exchange column.

Diluted supernatant is loaded at a linear flow rate of 90 cm/h onto a SP-sepharose FF (Pharmacia) column equilibrated with 50 mM sodium acetate, pH 4.5 until the effluent from the column reaches a stable UV and conductivity baseline. To remove any unbound material, the column is washed using the equilibration buffer until the effluent from the column reaches a stable level with respect to UV absorbance and conductivity. The bound G-CSF protein is eluted from the column using a linear gradient; 30 column volumes; 0-80% buffer B (50 mM NaAc, pH 4.5, 750 mM NaCl) at a flow rate of 45 cm/h. Based on SDS-polyacrylamide gel electrophoresis, fractions containing G-CSF are pooled. Sodium chloride is added until the ionic strength of the solution is more than 80 mS/cm.

The protein solution is applied onto a Phenyl Toyo Pearl 650S column equilibrated with 50 mM NaAc, pH 4.5, 750 mM NaCl. Any unbound material is washed off the column using the equilibration buffer. Elution of G-CSF is performed by applying a step gradient of MilliQ water. Fractions containing G-CSF are pooled. By using this 2-step down stream processing strategy, more than 90% pure G-CSF can be obtained. The purified protein is then quantified using spectrophotometric measurements at 280 nm and/or by amino acid analysis.

Fractions containing G-CSF are pooled. Buffer exchange and concentration is performed using VivaSpin concentrators (mwco: 5 kDa).

EXAMPLE 5

Identification and Quantification of Non-Conjugated and Conjugated hG-CSF and Variants Thereof SDS-Polyacryl Amide Gel Electrophoresis The purified, concentrated G-CSF was analyzed by SDS-PAGE. A single band having an apparent molecular weight of approx. 17 kDa was dominant.

Absorbance

An estimate of the G-CSF concentration is obtained by spectrophotometric methods. By measuring the absorbance at 280 m and using a theoretically extinction coefficient of 0.83, the protein concentration can be calculated.

Amino Acid Analysis

A more accurate protein determination can be obtained by amino acid analysis. Amino acid analysis performed on a purified G-CSF revealed that the experimentally determined amino acid composition is in agreement with the expected amino acid composition based on the DNA sequence.

EXAMPLE 6

MALDI-TOF Mass Spectrometry of PEGylated wt G-CSF and G-CSF Variants

MALDI-TOF mass spectrometry was used to evaluate the number of PEG-groups attached to PEGylated wt G-CSF and to selected PEGylated G-CSF variants.

Wt G-CSF contains 5 primary amines that are the expected attachment sites for SPA-PEG (the N-terminal amino-group and the ε-amino-group on K16, K23, K34 and K40). Following PEGylation of wt G-CSF with SPA-PEG 5000, MALDI-TOF mass spectrometry showed the presence of species of wt G-CSF with mainly 4, 5 and 6 PEG-groups attached. In addition, wt G-CSF with 7 PEG-groups attached was clearly seen although in minor amounts.

The G-CSF variant having the substitutions K16R, K34R, K40R, Q70K, Q90K, and Q120K also contains 5 primary amines (the N-terminal amino-group and the ε-amino-group on K23, K70, K90 and K120). Following PEGylation of this G-CSF variant with SPA-PEG5000, MALDI-TOF mass spectrometry showed the presence of species of the G-CSF variant with mainly 4, 5 and 6 PEG-groups attached. In addition, the G-CSF variant with 7 PEG-groups attached was clearly seen although in minor amounts.

The G-CSF variant having the substitutions K16R, K34R, and K40R contains 2 primary amines (the N-terminal amino-group and the ε-amino-group on K23). Following PEGylation of this G-CSF variant with SPA-PEG 12000, MALDI-TOF mass spectrometry showed the presence of species of the G-CSF variant with mainly 2 and 3 PEG-groups attached. In addition, the G-CSF variant with 4 PEG-groups attached was clearly seen although in minor amounts.

These observations clearly show that in addition to amino acid residues containing amine groups, other amino acid residues are sometimes PEGylated under the PEGylation conditions used. It also shows that it is of some importance for the PEGylation where amine groups are introduced. This has also been observed using SDS-PAGE analysis of wt G-CSF and G-CSF variants.

As described in Example 12, it has been shown that histidine 170 is fully PEGylated when the SPA-PEG chemistry is used. Furthermore, K23 and S159 are partly PEGylated. This explains the presence of 1-2 extra PEGylation sites besides the primary amines in hG-CSF and the variants that have been made.

EXAMPLE 7

Peptide Mapping of PEGylated and Non-PEGylated G-CSF Variants

In order to map the additional attachment sites for SPA-PEG on G-CSF and G-CSF variants the following strategy was used.

A G-CSF variant with a low number of amine groups was chosen in order to reduce the number of expected PEGylation sites to a minimum. The G-CSF variant chosen has the substitutions K16R, K34R, K40R and H170Q. Apart from the ε-amino-group on K23 that previous data had shown not to be PEGylated to any large extent, this variant only contains one primary amine at the N-terminal. Thus, the background PEGylation on amine groups is significantly reduced in this G-CSF variant. The G-CSF variant was PEGylated using SPA-PEG 5000. Following PEGylation, the G-CSF variant was denatured, the disulphide bonds reduced, the resulting thiol groups alkylated, and the alkylated and PEGylated protein degraded with a glutamic acid-specific protease. Finally, the resulting peptides were separated by reversed phase HPLC.

Parallel with this, the non-PEGylated version of the G-CSF variant with the substitutions K16R, K34R, and K40R was treated identically in order to create a reference HPLC chromatogram.

Comparison of the HPLC chromatograms of the degradation of the PEGylated G-CSF variant and the non-PEGylated G-CSF variant should then reveal which peptides disappear upon PEGylation. Identification of these peptides by N-terminal amino acid sequencing of the peptide from the non-PEGylated G-CSF variant then indirectly points to the positions that are PEGylated.

In principle, it would have been preferable to use the non-PEGylated version of the G-CSF variant having all the substitutions K16R, K34R, K40R and H170Q, but for all practical purposes this does not matter.

More specifically, approximately 1 mg of the PEGylated G-CSF variant having the substitutions K16R, K34R, K40R and H170Q and approximately 500 µg of the non-PEGylated G-CSF variant having the substitutions K16R, K34R, and K40R were dried in a SpeedVac concentrator. The two samples were each dissolved in 400 µl 6 M guanidinium, 0.3 M Tris-HCl, pH 8.3 and denatured overnight at 37° C. Following denaturation, the disulfide bonds in the proteins were reduced by addition of 50 µl 0.1 M DTT in 6 M guanidinium, 0.3 M Tris-HCl, pH 8.3. After 2 h of incubation at ambient temperature the thiol groups present were alkylated by addition of 50 µl 0.6 M iodoacetamid in 6 M guanidinium, 0.3 M Tris-HCl, pH 8.3. Alkylation took place for 30 min at ambient temperature before the reduced and alkylated proteins were buffer changed into 50 mM $NH_4HCO_3$ using NAP5 columns. The volumes of the samples were reduced to approximately 200 µl in a SpeedVac concentrator before addition of 20 µg and 10 µg glutamic acid-specific protease, respectively. The degradations with glutamic acid-specific protease were carried out for 16 h at 37° C. The resulting peptides were separated by reversed phase HPLC employing a Phenomenex Jupiter $C_{18}$ column (0.2*5 cm) eluted with a linear gradient of acetonitrile in 0.1% aqueous TFA. The collected fractions were analyzed by MALDI-TOF mass spectrometry and subsequently selected peptides were subjected to N-terminal amino acid sequence analysis.

Comparison of the HPLC chromatograms of the degradations of the PEGylated G-CSF variant and the non-PEGylated G-CSF variant revealed that only two fractions disappear upon PEGylation. N-terminal amino acid sequence analysis of the two fractions from the non-PEGylated G-CSF variant showed that the peptides both were derived from the N-terminal of G-CSF. One peptide consisted of amino acid residues 1-11 generated by an unexpected cleavage following Gln 11. The other peptide consisted of amino acid residues 1-19 generated by an expected cleavage following Glu19.

It was expected that the N-terminal peptide of G-CSF would be identified using this approach, as the N-terminal amino group is easily PEGylated. However, none of the additional attachment sites for SPA-PEG 5000 were identified using this approach.

An alternative to the indirect identification of PEG 5000 attachment sites is direct identification of the attachment sites in PEGylated peptides. However, the fractions containing the PEGylated peptides in the HPLC separation of the degraded PEGylated G-CSF variant are poorly separated from each other and from several fractions containing non-PEGylated peptides. Thus, N-terminal amino acid sequence analysis of these fractions did not result in any useful data except for an indication that K23 could be partially PEGylated.

To overcome these problems, two pools of PEGylated peptides were made from the fractions from the first HPLC separation. These two pools were dried in a SpeedVac concentrator, dissolved in 200 µl freshly prepared 50 mM $NH_4HCO_3$ and further degraded with 1 µg of chymotrypsin. The resulting peptides were separated by reversed phase HPLC employing a Phenomenex Jupiter $C_{18}$ column (0.2*5 cm) eluted with a linear gradient of acetonitrile in 0.1% aqueous TFA. The collected fractions were analyzed by MALDI-TOF mass spectrometry and subsequently selected peptides were subjected to N-terminal amino acid sequence analysis.

From the N-terminal amino acid sequence determinations it could be determined that K23 as well as S159 are partially PEGylated. It was not possible to determine the exact degree of PEGylation at these two positions, but the PEGylation is only partial as peptides where K23 and S159 are unmodified were identified and sequenced from the initial HPLC separation.

EXAMPLE 8

Glycosylation of wt G-CSF and G-CSF Variants

A consistent observation when analyzing purified wt G-CSF and G-CSF variants by MALDI-TOF mass spectrometry is the presence of an additional component with a mass approximately 324 Da larger than the mass of the G-CSF molecule analyzed. As the component with the lowest mass invariantly has the mass of the G-CSF molecule and because the G-CSF molecules have the correct N-terminal amino acid sequence, it was concluded that the additional component is a modified G-CSF molecule carrying two hexose residues. In many cases the unmodified G-CSF molecule gives rise to the most intense signal but in some cases the intensity of the signal for the modified G-CSF molecule is the most intense.

During the analysis of the peptides generated with the aim of identifying the additional PEGylation sites, two peptides of interest for identifying the site of glycosylation were identified in each of the degradations.

In both HPLC separations, the two peptides elute next to each other and MALDI-TOF mass spectrometry shows a mass difference between the two peptides of approximately 324 Da. The mass spectrometry data indicates that the peptide covers amino acid residues 124-162. N-terminal amino acid sequence analysis of all four peptides showed that this assignment is correct and that Thr133 is the only site of modification. In the peptides with the mass of the unmodified peptide, Thr133 is clearly seen in the sequence, while no amino acid residue can be assigned at position 133 in the peptides with an additional mass of 324 Da. As all other amino acid residues could be assigned in the sequence, it was concluded that Thr133 is the only site of modification. This glycosylation site was previously reported to be used in recombinant G-CSF expressed in CHO cells, although the glycan is different from the one attached by yeast.

The non-glycosylated wt G-CSF has been separated from the glycosylated wt G-CSF, employing reversed phase HPLC using a Vydac $C_{18}$ column (0.21*5 cm) isocratically eluted with 51% acetonitrile in 0.1% TFA, as a fraction shown by MALDI-TOF mass spectrometry only to contain the non-glycosylated form of wt G-CSF.

EXAMPLE 9

Separation of G-CSF Molecules with Different Numbers of PEG Molecules Covalently Attached Separation of G-CSF molecules covalently attached to 4, 5 or 6 PEG-groups was obtained as follows. PEGylated protein in 20 mM sodium citrate, pH 2.5 was applied to an SP-sepharose FF column equilibrated with 20 mM sodium citrate pH 2.5. Any unbound material was washed off the column. Elution was performed using a pH gradient. PEGylated G-CSF began to elute from the column at approx. pH 3.8 and continued to elute in fractions covering a pH span from 3.8 to 4.5.

The fractions were subjected to SDS-PAGE and mass spectrometric analysis. These analyses indicate that G-CSF having the highest degree of PEGylation is located in the "low pH fractions". PEGylated G-CSF having a lower degree of PEGylation is eluted in the "high pH fractions".

Amino acid analysis performed on PEGylated G-CSF showed good consistency between the theoretically and the experimentally determined extinction coefficient.

EXAMPLE 10

Construction of hG-CSF Variants

Specific substitutions of existing amino acids in hG-CSF to other amino acid residues, e.g. the specific substitutions discussed above in the general description, were introduced using standard DNA techniques known in the art. The new G-CSF variants were made using plasmid pG-CSFcerevisiae containing the gene, encoding hG-CSF without the HIS tag, as DNA template in the PCR reactions. The variants were expressed in S. cerevisiae and purified as described in Example 4. Some of the constructed G-CSF variants are listed below (see Examples 12 and 13).

EXAMPLE 11

Covalent Attachment of SPA-PEG to hG-CSF or Variants Thereof.

Human G-CSF and variants thereof were covalently linked to SPA-PEG 5000, SPA-PEG 12000 and SPA-PEG 20000 (Shearwater) as described above ("PEGylation of hG-CSF and variants thereof in solution"). The in vitro activities of the conjugates are listed in Example 13.

EXAMPLE 12

Identification of SPA-PEG Attachment Sites in G-CSF by Site-Directed Mutagenesis Followed by PEGylation of the Purified Variants SPA-PEG may be attached to other amino acid residues than lysine in G-CSF. In order to determine whether SPA-PEG was attached to histidines, serines, threonines and arginines, variants were made in which these amino acids were substituted to lysine, alanine or glutamine. The variants were expressed in S. cerevisiae, purified and PEGylated followed by analysis of the number of attached SPA-PEG molecules on SDS-PAGE. This analysis was performed by visual inspection of the SDS-PAGE gels, all of which contained three major bands. The degree of PEGylation was estimated to the nearest 5% for each band based on the relative size of the bands. A reduction in the number of attached SPA-PEG molecules after substitution of a given amino acid with glutamine or alanine strongly indicates that this amino acid is PEGylated by SPA-PEG, and this observation is further supported by an unchanged degree of PEGylation after substitution of the amino acid to lysine. The analyzed variants are listed below.

| G-CSF variant | No. of attached PEG groups |
| --- | --- |
| hG-CSF | 10% 4 PEG, 75% 5 PEG, 15% 6 PEG |
| K23R | 10% 4 PEG, 85% 5 PEG, 5% 6 PEG |
| H43Q | 10% 4 PEG, 75% 5 PEG, 15% 6 PEG |
| H43K | 10% 5 PEG, 75% 6 PEG, 15% 7 PEG |
| H52Q | 10% 4 PEG, 75% 5 PEG, 15% 6 PEG |
| H52K | 10% 5 PEG, 75% 6 PEG, 15% 7 PEG |
| H156Q | 10% 4 PEG, 75% 5 PEG, 15% 6 PEG |
| H156K | 10% 5 PEG, 75% 6 PEG, 15% 7 PEG |
| H170Q | 10% 3 PEG, 75% 4 PEG, 15% 5 PEG |
| H170K | 10% 4 PEG, 75% 5 PEG, 15% 6 PEG |
| K16/34R | 10% 2 PEG, 75% 3 PEG, 15% 4 PEG |
| K16/34R R22K | 10% 3 PEG, 75% 4 PEG, 15% 5 PEG |
| K16/34R R22Q | 10% 2 PEG, 75% 3 PEG, 15% 4 PEG |
| K16/34R S142A | 10% 2 PEG, 75% 3 PEG, 15% 4 PEG |
| K16/34/40R | 10% 1 PEG, 75% 2 PEG, 15% 3 PEG |
| K16/34/40R S53K | 10% 2 PEG, 75% 3 PEG, 15% 4 PEG |
| K16/34/40R S53A | 10% 2 PEG, 75% 3 PEG, 15% 4 PEG |
| K16/34/40R S62K | 10% 2 PEG, 75% 3 PEG, 15% 4 PEG |
| K16/34/40R S66K | 10% 2 PEG, 75% 3 PEG, 15% 4 PEG |
| K16/34/40R S80K | 10% 2 PEG, 75% 3 PEG, 15% 4 PEG |
| K16/34/40R T105K | 10% 2 PEG, 75% 3 PEG, 15% 4 PEG |
| K16/34/40R T133K | 10% 2 PEG, 75% 3 PEG, 15% 4 PEG |
| K16/34/40R S142K | 10% 2 PEG, 75% 3 PEG, 15% 4 PEG |
| K16/34/40R R147K | 10% 2 PEG, 75% 3 PEG, 15% 4 PEG |
| K16/34/40R S155K | 10% 2 PEG, 75% 3 PEG, 15% 4 PEG |
| K16/34/40R S159K | 10% 2 PEG, 85% 3 PEG, 5% 4 PEG |
| K16/34/40R S170K | 10% 1 PEG, 75% 2 PEG, 15% 3 PEG |

The data show that besides the N-terminus, K16, K34 and K40, SPA-PEG also is covalently bound to H170. Furthermore, the data show that only 10% of the available K23 amino acid residues are PEGylated, and that approximately 10% of S159 is PEGylated.

EXAMPLE 13

In Vitro Biological Activity of Non-Conjugated and Conjugated hG-CSF and Variants Thereof.

The in vitro biological activities of conjugated and non-conjugated hG-CSF and variants thereof were measured as described above in "Primary assay 2—in vitro hG-CSF activity assay". The in vitro bioactivities, represented by the measured EC50 values for each variant with and without conjugation of SPA-PEG 5000 to the available PEGylation sites, are listed below. The values have been normalized with respect to the EC50 value of non-conjugated hG-CSF (Neupogen®), i.e. the values in the table indicate % activity relative to the activity of non-conjugated hG-CSF. This value was measured simultaneously with the variants each time under identical assay conditions. The EC50 value of hG-CSF in the described assay is 30 pM.

| G-CSF variant | EC50 (% of hG-CSF) non-conjugated | EC50 (% of hG-CSF) conjugated to SPA-PEG 5000 |
| --- | --- | --- |
| G-CSF with N-terminal Histidine tag | 10 | Not determined |
| G-CSF without N-terminal Histidine tag | 100 | 0.1 |

-continued

| G-CSF variant | EC50 (% of hG-CSF) non-conjugated | EC50 (% of hG-CSF) conjugated to SPA-PEG 5000 |
|---|---|---|
| 16R | 100 | 1 |
| 16Q | 80 | 1 |
| 23Q | 80 | 0.1 |
| 23R | 100 | 0.1 |
| 34R | 100 | 1 |
| 34A | 80 | 1 |
| 34Q | 70 | 1 |
| 40R | 50 | 1 |
| K16/23R | 100 | 1 |
| K16/23Q | 80 | 1 |
| K34/40R | 50 | 5 |
| K16/34R | 100 | 10 |
| K16/40R | 50 | 5 |
| K16/23/34R | 50 | 10 |
| K16/23/40R | 50 | 5 |
| K16/34/40R | 35 | 30 |
| K16/23/34/40R | 20 | 15 |
| K16/34/40R L3K | 50 | 25 |
| K16/34/40R E45K | Expressed at low levels | Not determined |
| K16/34/40R E46K | 10 | 1 |
| K16/34/40R S53K | 5 | 0.5 |
| K16/34/40R S62K | 10 | 0.5 |
| K16/34/40R S66K | 20 | 2 |
| K16/34/40R Q67K | 10 | 0.2 |
| K16/34/40R Q70K | 30 | 20 |
| K16/34/40R S76 | 50 | 20 |
| K16/34/40R Q77 | 1 | 0 |
| K16/34/40R S80K | 10 | 0.2 |
| K16/34/40RQ90K | 30 | 20 |
| K16/34/40R E98K | Expressed at low levels | Not determined |
| K16/34/40R D104K | 10 | 0.9 |
| K16/34/40R T105K | 30 | 10 |
| K16/34/40R Q120K | 30 | 20 |
| K16/34/40R Q131K | Expressed at low levels | Not determined |
| K16/34/40R T133K | 30 | 10 |
| K16/34/40R Q134K | 10 | 0.2 |
| K16/34/40R S142K | 20 | 7 |
| K16/34/40R R147K | 20 | 1 |
| K16/34/40R S155K | 20 | 1 |
| K16/34/40R Q158 | 20 | 5 |
| K16/34/40R S159K | 20 | 3 |
| K16/34/40R Q70K Q90K | Not determined | 20 |
| K16/34/40R Q70K Q120K | 25 | 25 |
| K16/34/40R Q90K T105K | 40 | 10 |
| K16/34/40R Q90K Q120K | 25 | 15 |
| K16/34/40R Q90K S159K | 45 | Not determined |
| K16/34/40R T105K Q120K | 20 | 8 |
| K16/34/40R T105K S159K | 40 | 20 |
| K16/34/40R Q120K T133K | 20 | 8 |
| K16/34/40R Q120K S142K | 10 | 2 |
| K16/34/40R Q70K Q90K T105K | 10 | 4 |
| K16/34/40R Q70K Q90K Q120K | 20 | 12 |
| K16/34/40R Q70K Q90K T133K | 15 | 5 |
| K16/34/40R Q70K T105K Q120K | 10 | 2 |
| K16/34/40R Q70K Q120K T133K | 15 | 2 |
| K16/34/40R Q70K Q120K S142K | 10 | 1 |
| K16/34/40R Q90K T105K Q120K | 10 | 2 |
| K16/34/40R Q90KT105K T133K | 10 | 2 |
| K16/34/40R Q90K T105K S159K | 55 | 5 |
| K16/34/40R Q90K Q120K T133K | 15 | 2 |
| K16/34/40R Q90K Q120K S142K | 10 | 1 |
| K16/34/40R T105K Q120K T133K | 10 | 1 |
| K16/34/40R Q120K T133K S142K | 10 | 1 |

The data show that substitution of K23 to arginine does not increase the activity of the conjugated protein. This is due to the fact that only 10% of K23 is PEGylated, whereby the conjugated K23R variant has essentially the same number of PEG groups attached to it and has the same location of the PEGylation sites as hG-CSF. Removal of the remaining lysines at position K16, K34 and K40 resulted in a G-CSF variant with significant activity after PEGylation. Conjugation of SPA-PEG 5000 to this variant does not decrease the activity significantly as compared to the non-conjugated variant. Thus, PEGylation of the N-terminus and H170 with SPA-PEG 5000 (see Example 12) does not decrease the activity of hG-CSF. It was decided to use hG-CSF K16R K34R K40R as the backbone for insertion of new PEGylation sites. 24 new PEGylation sites between residues L3 and H159 were introduced in this backbone. These residues are distributed over the parts of hG-CSF that do not interact with the G-CSF receptor. Introduction of new PEGylation sites at positions L3, Q70, S76, Q90, T105, Q120, T133 and S142 resulted in hG-CSF variants that retained a significant amount of activity after PEGylation by SPA-PEG 5000. Thus, some of these new PEGylation sites were combined in hG-CSF variants that had 2 or 3 new PEGylation sites.

Furthermore, SPA-PEG 12000 and SPA-PEG 20000 were attached to a group a selected hG-CSF variants. The in vitro activities are listed below (% of Neupogen®).

| G-CSF variant | EC50 (% of hG-CSF) conjugated to SPA-PEG 12000 | EC50 (% of hG-CSF) conjugated to SPA-PEG 20000 |
|---|---|---|
| K16/34/40R | 10 | 1 |
| K16/34/40R Q90K | Not determined | 7 |
| K16/34/40R Q70K Q90K | 8 | Not determined |
| K16/34/40R Q90K T105K | 1 | <1 |
| K16/34/40R T105K S159K | 6 | 5 |
| K16/34/40R Q90K T105K S159K | 1 | <1 |

EXAMPLE 14

In Vivo Half-Life of Non-Conjugated and Conjugated hG-CSF and Variants Thereof.

Figure 2:
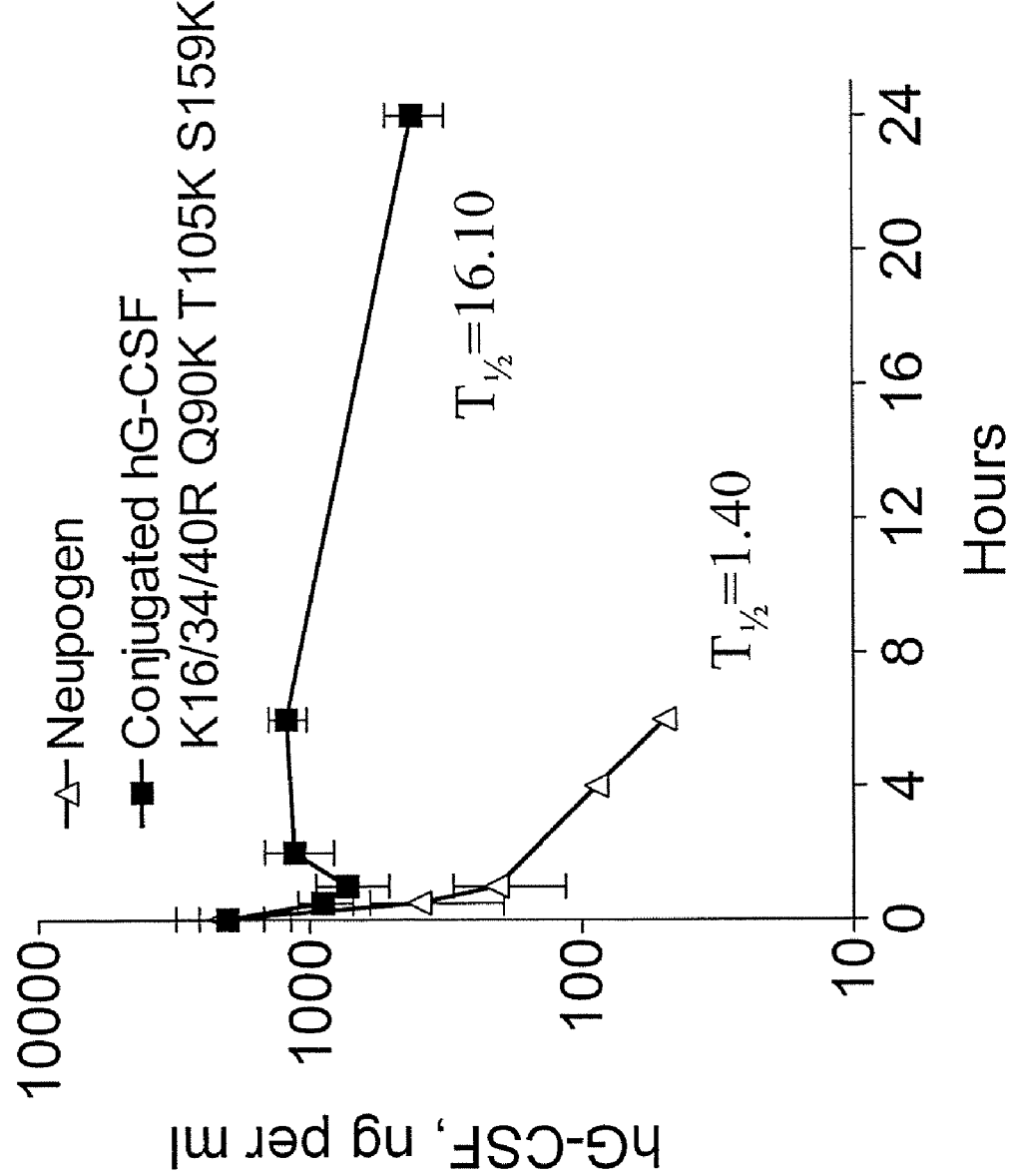
FIG. 2: The in vivo half-lives of rhG-CSF (Neupogen®) and SPA-PEG 5000-conjugated hG-CSF K16R K34R K40R Q90K T105K Q159K

The in vivo half-lives of non-conjugated hG-CSF (Neupogen®), SPA-PEG 5000 conjugated hG-CSF K16R K34R K40R Q70K Q90K Q120K and SPA-PEG 5000 conjugated hG-CSF K16R K34R K40R Q90K T105K S159K were measured as described above ("Measurement of the in vivo half-life of conjugated and non-conjugated rhG-CSF and variants thereof"). The results are shown in FIGS. 1 and 2. The in vivo half-life of Neupogen® was determined to be 2.01 hours and 1.40 hours, respectively. In an earlier, similar experiment (U.S. Pat. No. 5,824,778), the in vivo half-life of hG-CSF was determined to be 1.79 hours. The results of the experiments described herein can therefore be directly compared to that experiment. The in vivo half-lives of SPA-PEG 5000 conjugated hG-CSF K16R K34R K40R Q70K Q90K Q120K and SPA-PEG 5000 conjugated hG-CSF K16R K34R K40R Q90K T105K S159K were determined to be 12.15 hours and 16.10 hours, respectively. Thus, introducing new PEGylation sites in hG-CSF and conjugating SPA-PEG 5000 to them has resulted in a significant increase in the in vivo half-life.

In the earlier experiment described above (U.S. Pat. No. 5,824,778), the in vivo half-life of hG-CSF conjugated to a larger N-terminally attached PEG molecule (10 kDa) was determined to be 7.05 hours. Thus, SPA-PEG 5000 conjugated hG-CSF K16R K34R K40R Q70K Q90K Q120K and SPA-PEG 5000 conjugated hG-CSF K16R K34R K40R Q90K T105K S159K have significantly longer half-lives than both Neupogen® and hG-CSF with a 10 kDa N-terminally conjugated PEG molecule. SPA-PEG 5000 conjugated hG-CSF K16R K34R K40R Q70K Q90K Q120K and SPA-PEG 5000 conjugated hG-CSF K16R K34R K40R Q90K T105K S159K both have three removed endogenous PEGylation sites and three new introduced PEGylation sites and thus are identical in size. The only difference between the two compounds is the in vitro activity, which is 12% and 5%, respectively, of that of Neupogen®. This difference results in a longer in vivo half-life of SPA-PEG 5000 conjugated K16R K34R K40R Q90K T105K S159K compared to SPA-PEG 5000 conjugated K16R K34R K40R Q70K Q90K Q120K.

Since the in vitro activities correlate with the receptor binding affinities of the compounds, it can be concluded that the receptor-mediated clearance of SPA-PEG 5000 conjugated K16R K34R K40R Q90K T105K S159K is slower than that of SPA-PEG 5000 conjugated K16R K34R K40R Q70K Q90K Q120K. Thus, a combination of increasing the size and reducing the in vitro activity of G-CSF results in G-CSF compounds with significantly longer in vivo half-lives than previously described compounds.

EXAMPLE 15

In Vivo Biological Activity in Health Rats of Non-Conjugated and Conjugated hG-CSF and Variants Thereof.

Figure 3:
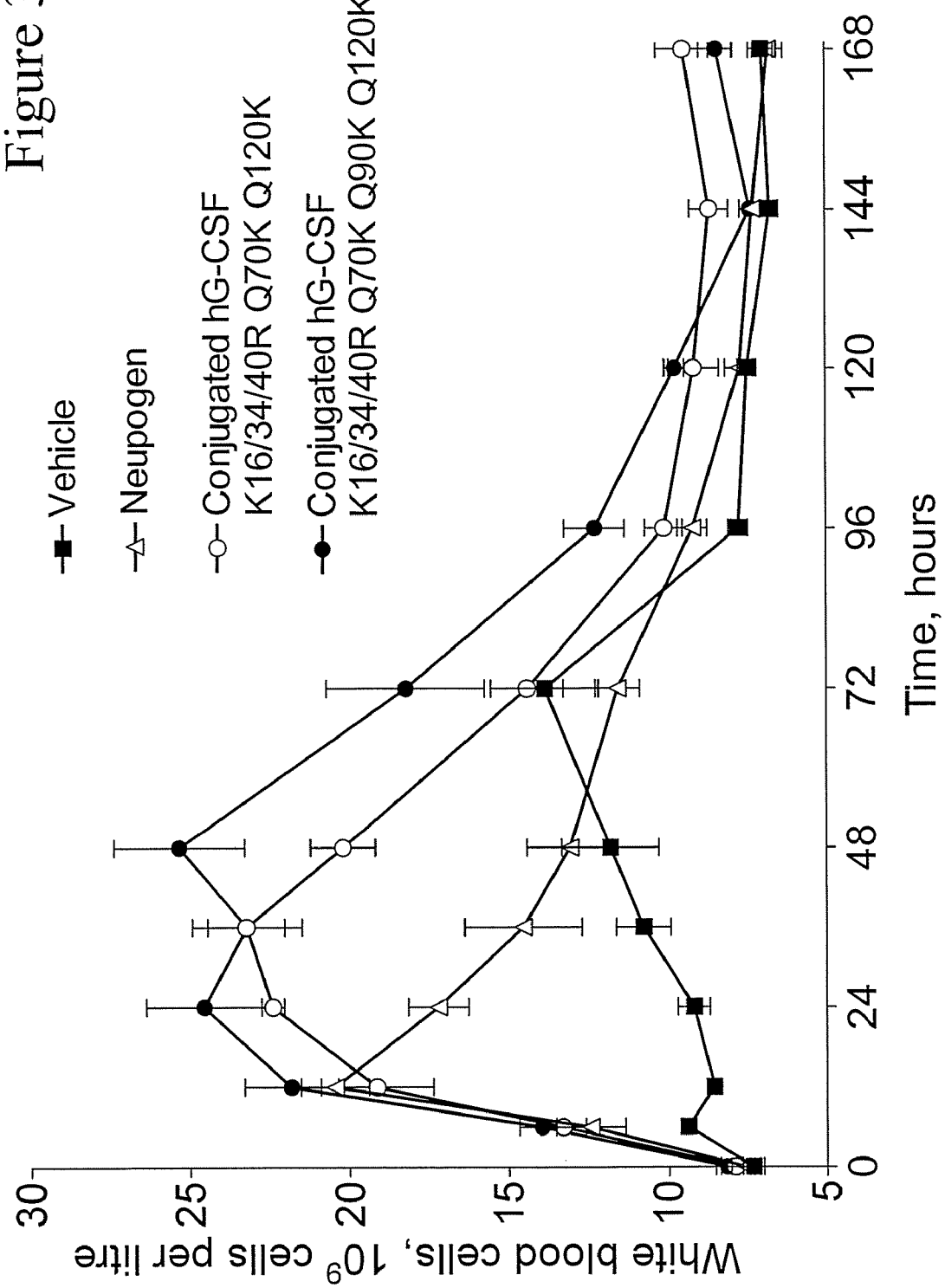
FIG. 3: The in vivo biological activities in healthy rats of rhG-CSF (Neupogen®), SPA-PEG 5000-conjugated hG-CSF K16R K34R K40R Q70K Q120K and SPA-PEG 5000-conjugated hG-CSF K16R K34R K40R Q70K Q90K Q120K.
Figure 4:
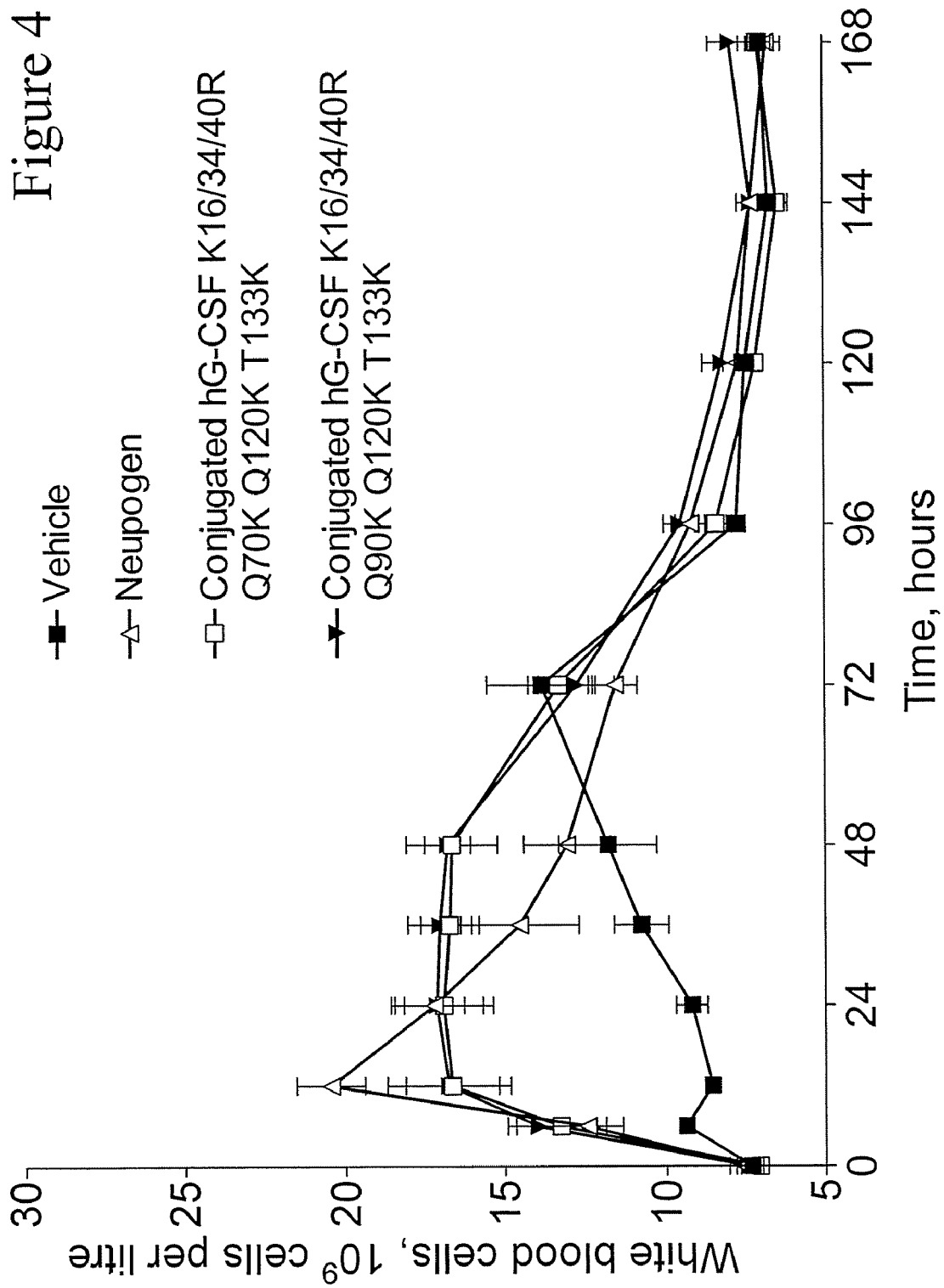
FIG. 4: The in vivo biological activities in healthy rats of rhG-CSF (Neupogen®), SPA-PEG 5000-conjugated hG-CSF K16R K34R K40R Q70K Q120K T133K and SPA-PEG 5000-conjugated hG-CSF K16R K34R K40R Q90K Q120K T133K.

The in vivo biological activities of non-conjugated hG-CSF (Neupogen®), SPA-PEG 5000 conjugated hG-CSF K16R K34R K40R Q70K Q120K, SPA-PEG 5000 conjugated hG-CSF K16R K34R K40R Q70K Q90K Q120K, SPA-PEG 5000 conjugated hG-CSF K16R K34R K40R Q70K Q120K T133K and SPA-PEG 5000 conjugated hG-CSF K16R K34R K40R Q90K Q120K T133K were measured as described above ("Measurement of the in vivo biological activity in healthy rats of conjugated and non-conjugated hG-CSF and variants thereof"). The results are shown in FIGS. 3 and 4.

No activity of Neupogen® could be detected at 48 hours after injection of 100 μg per kg body weight at t=0 hours. Activity of SPA-PEG 5000 conjugated hG-CSF K16R K34R K40R Q70K Q120K, SPA-PEG 5000 conjugated hG-CSF K16R K34R K40R Q70K Q120K T133K and SPA-PEG 5000 conjugated hG-CSF K16R K34R K40R Q90K Q120K T133K could be detected until 72 hours after the initial injection, while SPA-PEG 5000 conjugated hG-CSF K16R K34R K40R Q70K Q90K Q120K remained active in vivo until 96 hours after the initial injection. Thus, it was shown that all of these conjugated variants had a longer in vivo biological activity than Neupogen® and that SPA-PEG 5000 conjugated hG-CSF K16R K34R K40R Q70K Q90K Q120K remained active twice as long in vivo as Neupogen®. SPA-PEG 5000 conjugated hG-CSF K16R K34R K40R Q70K Q120K T133K and SPA-PEG 5000 conjugated hG-CSF K16R K34R K40R Q90K Q120K T133K, both with an in vitro activity of 2% of Neupogen® (Example 13), did not induce the same level of white blood cell formation during the initial 12 hours after administration as observed after administration of Neupogen®, SPA-PEG 5000 conjugated hG-CSF K16R K34R K40R Q70K Q120K and SPA-PEG 5000 conjugated hG-CSF K16R K34R K40R Q70K Q90K Q120K. Thus, the compounds with an in vitro activity of 2% or less compared to that of Neupogen® were unable to stimulate full formation of white blood cells immediately after administration.

Figure 5:
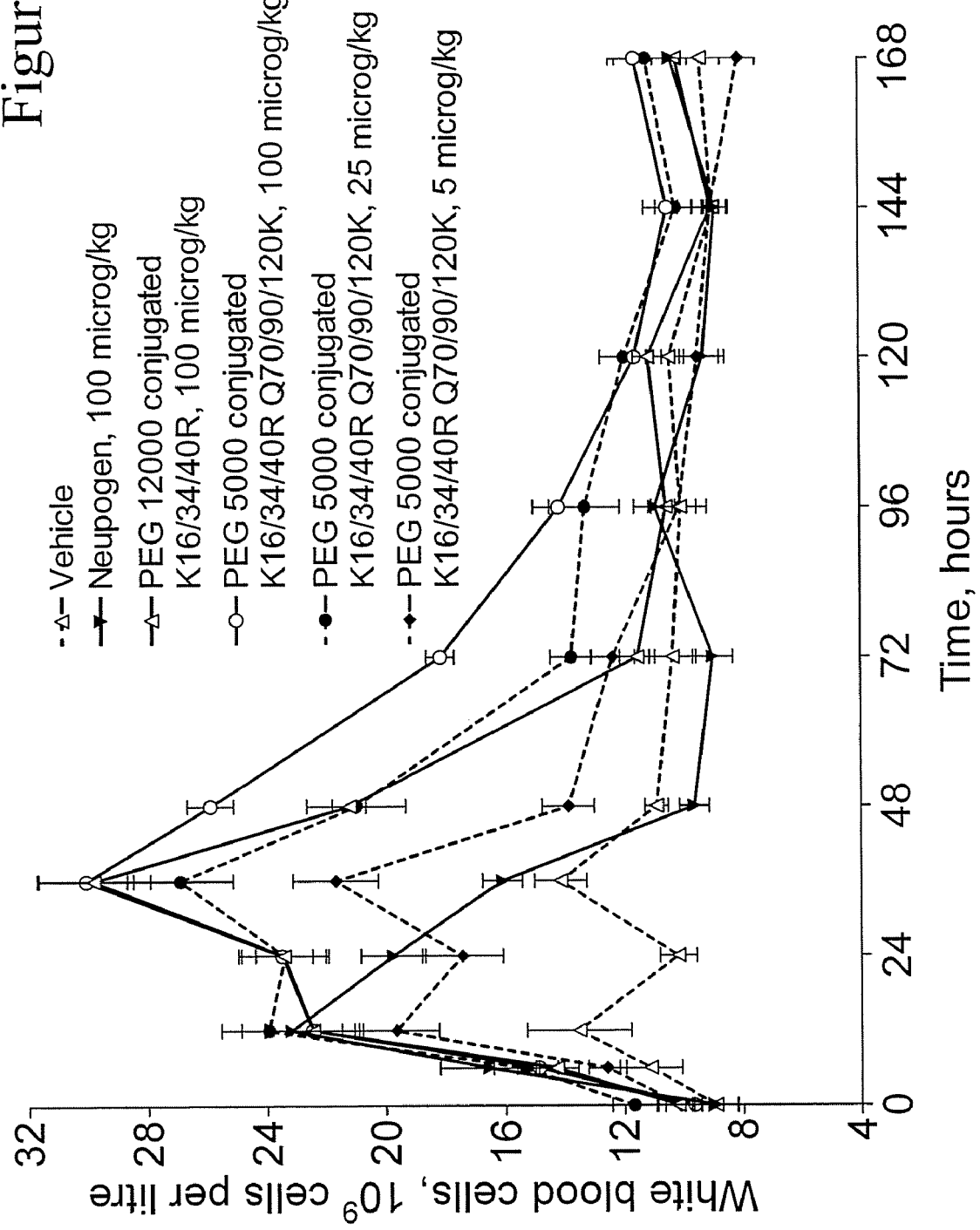
FIG. 5: The in vivo biological activities in healthy rats of rhG-CSF (Neupogen®), SPA-PEG 12000-conjugated hG-CSF K16R K34R K40R and different doses of SPA-PEG 5000-conjugated hG-CSF K16R K34R K40R Q70K Q90K Q120K.

Furthermore, the in vivo biological activities of Neupogen®, SPA-PEG 12000 conjugated hG-CSF K16R K34R K40R and different doses of SPA-PEG 5000 conjugated hG-CSF K16R K34R K40R Q70K Q90K Q120K were measured as described above ("Measurement of the in vivo biological activity in healthy rats of conjugated and non-conjugated hG-CSF and variants thereof"). The results are shown in FIG. 5. As observed earlier, no activity of Neupogen® could be detected 48 hours after the initial injection of 100 μg per kg body weight. Administration of 5 μg per kg body weight of SPA-PEG 5000 conjugated hG-CSF K16R K34R K40R Q70K Q90K Q120K resulted in a slightly longer in vivo biological activity than Neupogen®, while administration of 25 μg per kg body weight and 100 μg per kg body weight of this compound resulted in hG-CSF activity until 72 and 96 hours, respectively, after the initial injection. Thus, the duration of action of the SPA-PEG conjugated hG-CSF compounds can be controlled by increasing or decreasing the standard dosing regimen. SPA-PEG 12000 conjugated hG-CSF K16R K34R K40R remained active in vivo until 72 hours after administration of 100 µg per kg body weight. As described in Example 6, SPA-PEG 12000 conjugated hG-CSF K16R K34R K40R has 2 or 3 SPA-PEG 12000 groups attached while SPA-PEG 5000 conjugated hG-CSF K16R K34R K40R Q70K Q90K Q120K has 5 or 6 SPA-PEG 5000 groups attached. Thus, the molecular weights of the two compounds are 42-54 kDa and 43-48 kDa, respectively. The in vitro activities of the two compounds are 30% and 12%, respectively, of that of Neupogen®. The longer in vivo biological activity of SPA-PEG 5000 conjugated hG-CSF K16R K34R K40R Q70K Q90K Q120K as compared to SPA-PEG 12000 conjugated hG-CSF K16R K34R K40R with essentially the same molecular weight suggests that when the size of the G-CSF compounds is increased above a certain molecular weight through PEGylation, the duration of action can only be increased further by reducing the specific activity of the G-CSF compounds and thus, the receptor-mediated clearance (see Example 14).

Figure 6:
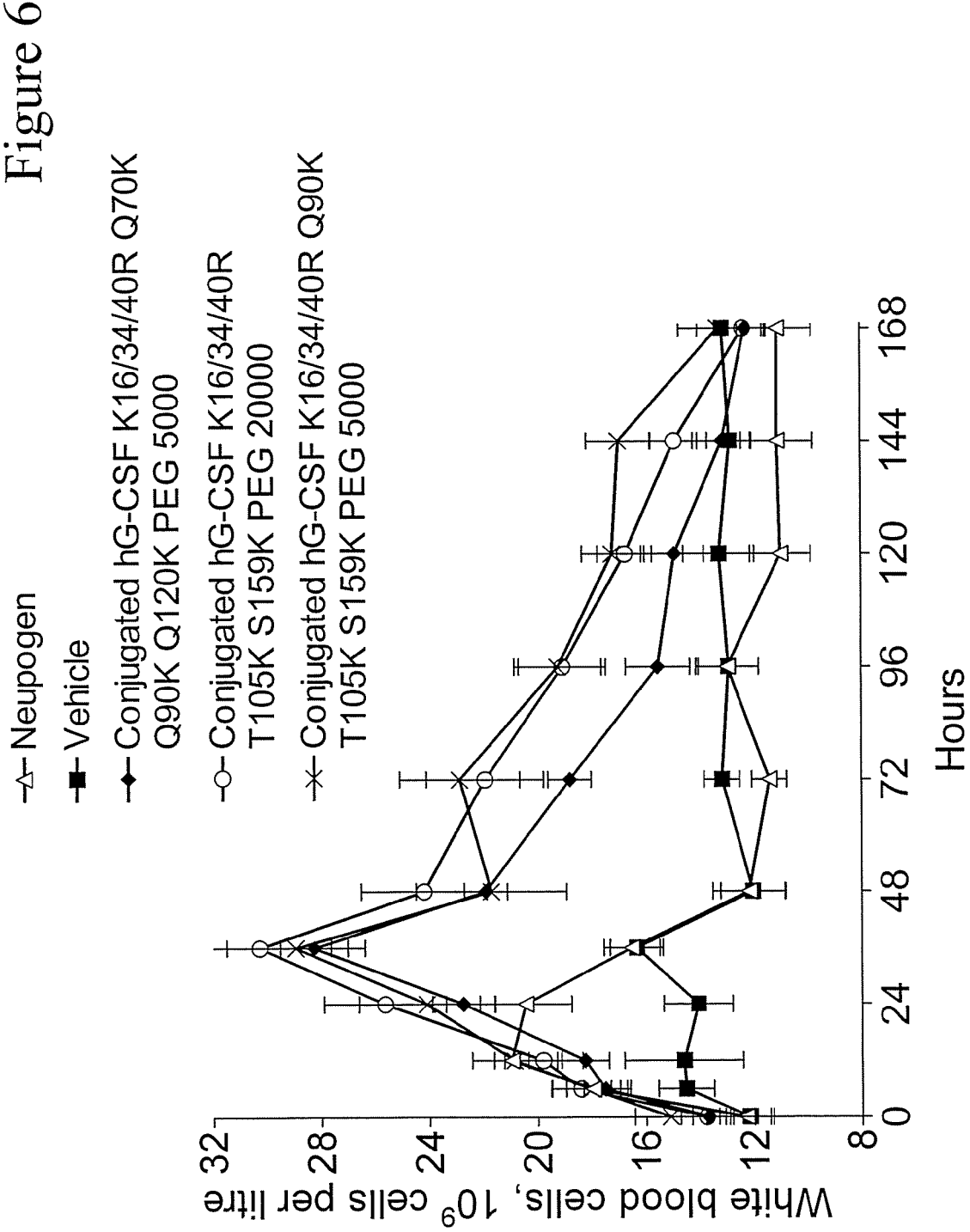
FIG. 6: The in vivo biological activities in healthy rats of rhG-CSF (Neupogen®), SPA-PEG 5000-conjugated hG-CSF K16R K34R K40R Q70K Q90K Q120K, SPA-PEG 5000-conjugated hG-CSF K16R K34R K40R Q90K T105K S159K and SPA-PEG 20000-conjugated hG-CSF K16R K34R K40R T105K S159K.

Furthermore, the in vivo biological activities of Neupogen®, SPA-PEG 5000 conjugated hG-CSF K16R K34R K40R Q70K Q90K Q120K, SPA-PEG 5000 conjugated hG-CSF K16R 34R 40R Q90K T105K S159K and SPA-PEG 20000 conjugated hG-CSF K16R 34R 40R T105K S159K were measured as described above ("Measurement of the in vivo biological activity in healthy rats of conjugated and non-conjugated hG-CSF and variants thereof"). The results are shown in FIG. 6.

As observed earlier, the conjugated hG-CSF variants had a significant longer duration of action than Neupogen®. Administration of each of these three conjugated hG-CSF variants resulted in formation of white blood cells at the same rate and to the same level as observed after administration of Neupogen® during the initial 12 hours after administration. The in vitro activities of SPA-PEG 5000 conjugated hG-CSF K16R K34R K40R Q70K Q90K Q120K, SPA-PEG 5000 conjugated hG-CSF K16R 34R 40R Q90K T105K S159K and SPA-PEG 20000 conjugated hG-CSF K16R 34R 40R T105K S159K are 12%, 5% and 5%, respectively, of that of Neupogen®, and thus, a hG-CSF compound with 5% of Neupogen® activity in vitro is able to induce full white blood cell formation after administration.

The apparent size on SDS-PAGE of Neupogen®, SPA-PEG 5000 conjugated hG-CSF K16R K34R K40R Q70K Q90K Q120K, SPA-PEG 5000 conjugated hG-CSF K16R 34R 40R Q90K T105K S159K and SPA-PEG 20000 conjugated hG-CSF K16R 34R 40R T105K S159K is 18 kDa, 60 kDa, 60 kDa and >100 kDa, respectively. SPA-PEG 5000 conjugated hG-CSF K16R 34R 40R Q90K T105K S159K and SPA-PEG 20000 conjugated hG-CSF K16R 34R 40R T105K S159K have almost identical durations of action in vivo, showing that the duration of action is not increased by increasing the molecular size of the conjugated hG-CSF compounds above an apparent size of about 60 kDa. Instead, when the apparent size of the conjugated hG-CSF compounds is above about 60 kDa, the duration of action may be increased be reducing the in vitro activity and hence, the receptor binding affinity of the compound. An additional example of this (see above) can be observed by comparing the in vivo duration of action of SPA-PEG 5000 conjugated hG-CSF K16R 34R 40R Q70K Q90K Q120K and SPA-PEG 5000 conjugated hG-CSF K16R34R 40R Q90K T105K S159K. The two compounds both have an apparent size of 60 kDa, while the in vitro activities are 12% and 5%, respectively. This difference is reflected directly in the in vivo duration of action of the two compounds, which is 96 hours and 144 hours, respectively.

EXAMPLE 16

In Vivo Biological Activity in Rats with Chemotherapy-Induced Neutropenia of Non-Conjugated and Conjugated hG-CSF and Variants Thereof.

Figure 7:
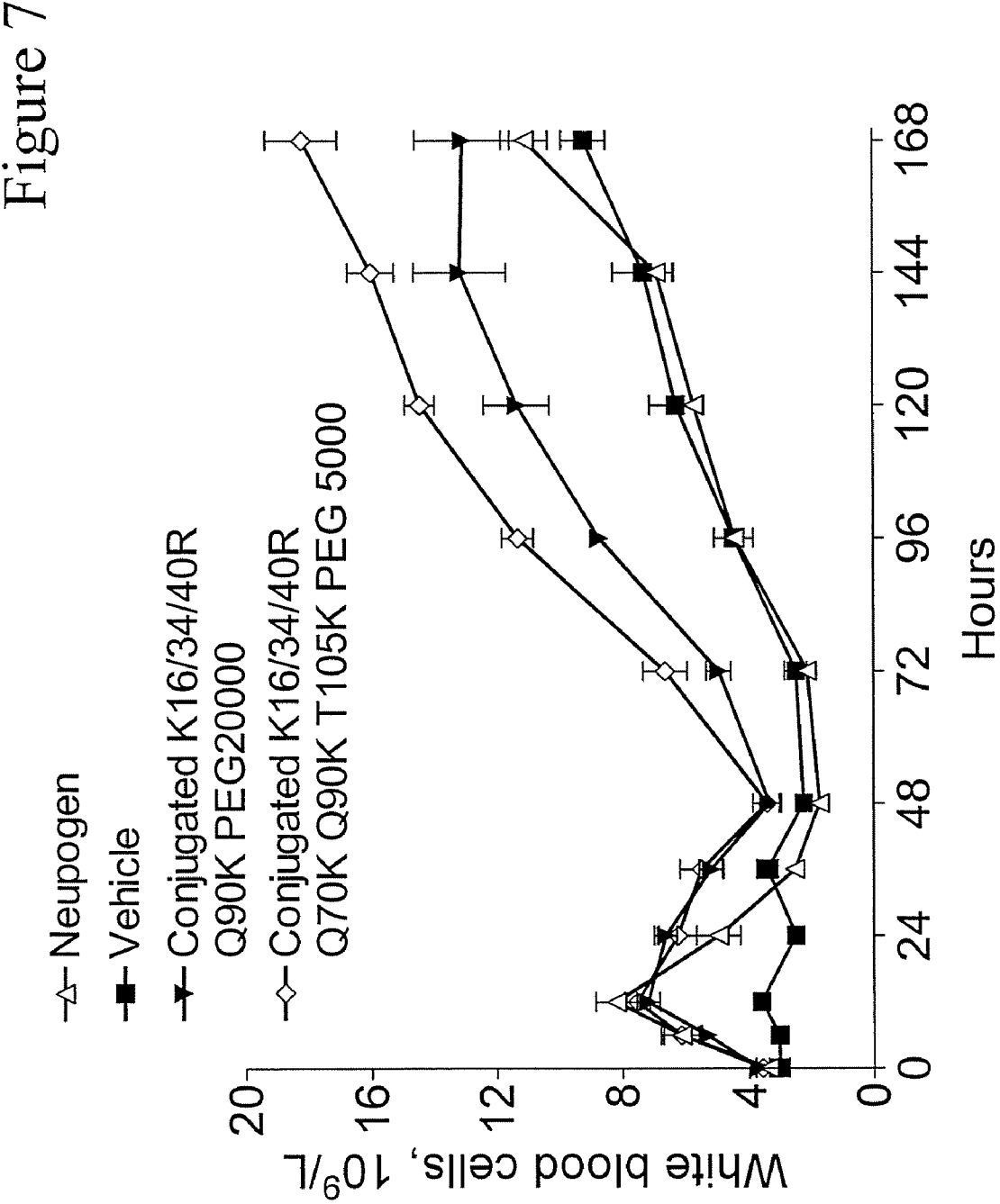
FIG. 7: The in vivo biological activities in rats with chemotherapy-induced neutropenia of rhG-CSF (Neupogen®), SPA-PEG 5000-conjugated hG-CSF K16R K34R K40R Q70K Q90K T105K, SPA-PEG 20000-conjugated hG-CSF K16R K34R K40R Q90K.

The in vivo biological activities in rats with chemotherapy-induced neutropenia of non-conjugated hG-CSF (Neupogen®), SPA-PEG 5000 conjugated hG-CSF K16R K34R K40R Q70K Q90K T105K and SPA-PEG 20000 conjugated hG-CSF K16R K34R K40R Q90K were measured as described above ("Measurement of the in vivo biological activity in rats with chemotherapy-induced neutropenia of conjugated and non-conjugated hG-CSF and variants thereof") using 50 mg per kg body weight of CPA and a single dose (100 µg per kg body weight) of G-CSF. The results are shown in FIG. 7. The three compounds induced an initial formation of white blood cells with identical rates. Thus, an in vitro activity of 4% of that of Neupogen® is sufficient for a conjugated hG-CSF compound to give full stimulation of white blood cell formation in vivo immediately after administration. After 36 hours the number of white blood cells (WBC) in the Neupogen®-treated rats dropped to the level that was observed in the untreated group ($<3\times10^9$ cells per litre). At this point the rats were neutropenic. The level of WBC in both groups reached normal levels ($9\times10^9$ cells per litre) after 144 hours.

The level of WBC in the two groups treated with SPA-PEG 5000 conjugated hG-CSF K16R K34R K40R Q70K Q90K T105K and SPA-PEG 20000 conjugated hG-CSF K16R K34R K40R Q90K dropped to a minimum of $4\times10^9$ cells per litre after 48 hours and then immediately started to increase. The WBC levels in both groups were back to normal after 96 hours. Thus, the two conjugated hG-CSF compounds were able to both relieve the degree of neutropenia and to reduce the time until the WBC levels were back to normal (the duration of neutropenia) significantly from 112 hours in the Neupogen®-treated group to 48 hours in the groups treated with either SPA-PEG 5000 conjugated hG-CSF K16R K34R K40R Q70K Q90K T105K and SPA-PEG 20000 conjugated hG-CSF K16R K34R K40R Q90K.

SPA-PEG 5000 conjugated hG-CSF K16R K34R K40R Q70K Q90K T105K more efficiently shortened the duration of neutropenia as compared to SPA-PEG 20000 conjugated hG-CSF K16R K34R K40R Q90K. Since the apparent size of both molecules is above 60 kDa (60 kDa and 80 kDa, respectively) this cannot be explained by a lower renal clearance of SPA-PEG 5000 conjugated hG-CSF K16R K34R K40R Q70K Q90K T105K than SPA-PEG 20000 conjugated hG-CSF K16R K34R K40R Q90K. The in vitro activity of SPA-PEG 5000 conjugated hG-CSF K16R K34R K40R Q70K Q90K T105K and SPA-PEG 20000 conjugated hG-CSF K16R K34R K40R Q90K are 4% and 7% of Neupogen®, respectively. This means that the receptor binding affinity and thus, the receptor-mediated clearance, of SPA-PEG 5000 conjugated hG-CSF K16R K34R K40R Q70K Q90K T105K is lower than for SPA-PEG 20000 conjugated hG-CSF K16R K34R K40R Q90K in the initial 48 hours after administration where the white blood cell levels are increased. Hence, when the rats become neutropenic after 48 hours, the in vivo concentration of SPA-PEG 5000 conjugated hG-CSF K16R K34R K40R Q70K Q90K T105K is higher than SPA-PEG 20000 conjugated hG-CSF K16R K34R K40R Q90K. Since a relatively low in vitro G-CSF activity of 4-5% of that of Neupogen® is sufficient to obtain full activation of the G-CSF receptors on the neutrophil progenitor cells (see above), this higher G-CSF concentration after 48 hours explains the faster increase in WBC levels in the SPA-PEG 5000 conjugated hG-CSF K16R K34R K40R Q70K Q90K T105K-treated group. Thus, in rats with chemotherapy-induced neutropenia, a conjugated G-CSF compound of the invention with an apparent size of at least about 60 kDa and an in vitro activity of 4% of that of Neupogen® is superior to similar size compounds with a higher in vitro activity.

EXAMPLE 17

Purification of G-CSF from *S. cerevisiae* Culture Supernatants

This example provides an alternative purification procedure to that of Example 4 for purification of hG-CSF and G-CSF variants.

Cells are removed by centrifugation, 5000 rpm, 10 min, 4° C., and the clarified supernatant is filtered through a 0.22 µm filter. The clarified and filtered supernatant is concentrated and diafiltered into 50 mM sodium acetate, pH 4.5, by Tangential Flow Filtration using 10 kDa membranes.

The resulting ultra filtrate is applied onto an SP-sepharose column (200 ml packed bed) equilibrated with at least 5 column volumes of 50 mM sodium acetate. Samples are loaded at a flow rate of approx. 20 ml/min. The column is washed using the equilibration buffer until a stable effluent is obtained as determined by absorbance at 280 nm. Using a stepwise buffer gradient (e.g. 10%, 20%, 30% and 35% buffer), G-CSF is eluted at 35% buffer at ambient flow rate, where the buffer is 750 mM NaCl in 50 mM sodium acetate.

This one-step method yields >95% pure G-CSF (as determined by SDS-PAGE).

EXAMPLE 18

Separation of Multi-PEGylated Species of G-CSF

Example 9 above describes a method for separation of G-CSF molecules with different numbers of PEG groups attached. This example provides an alternative procedure for separation of such multi-PEGylated G-CSF species in order to obtain a G-CSF product with a desired degree of uniformity in terms of the number of attached PEG groups.

A mixture of PEGylated G-CSF, covalently linked to e.g. SPA-PEG 5000 (Shearwater) as described above ("PEGylation of hG-CSF and variants thereof in solution"), is diluted with 20 mM citrate buffer, pH 2.5. The conductivity should be <3.5 mS/cm. The pH is adjusted to 2.5 as necessary using dilute HCl. The following buffers are used for the separation:

Buffer A: 20 mM sodium citrate, pH 2.5 (equilibration and washing buffer).

Buffer B: 20 mM sodium citrate, pH 2.5; 750 mM sodium chloride (elution buffer)

The sample to be separated is loaded onto an equilibrated SP-sepharose HP column (7 ml) at a flow rate of 2 ml/min. The column is washed with Buffer A until a stable baseline is obtained as monitored by $A_{280}$.

Multi-PEGylated species are separated by applying a linear gradient of 0-50% Buffer B for 180 minutes at a flow rate of 4 ml/min and collecting 2 ml fractions. The collected fraction are analyzed by SDS-PAGE, and fractions having a desired number of attached PEG groups are pooled. This allows purification of a PEGylated G-CSF mixture comprising species initially having, e.g., 3-6 attached PEG groups to result in a product having e.g. only 4 or 5 PEG groups attached, or a product having only a single number of attached PEG groups.

EXAMPLE 19

Peptide Mapping

Using a similar procedure to that described above in Example 7, but based on degradation with trypsin, the PEGylation pattern of a G-CSF conjugate of the invention was determined by peptide mapping. In this case, the polypeptide was produced in CHO cells (see Example 3) and had the substitutions K16R, K34R, K40R, T105K and S159K relative to the sequence of native human G-CSF. It was PEGylated with 5 kDa SPA-PEG as described above, resulting in modified proteins carrying predominantly 3, 4 or 5 PEG moieties, and to a small extent 6 PEG moieties. Five of the six possible PEG attachment sites are known, these being the N-terminal amino group, Lys23, Lys105, Lys159 and His170.

This peptide mapping analysis showed that the conjugated protein was essentially fully PEGylated at the N-terminal and at Lys105 and Lys159, while Lys23 was partially PEG-ylated. Although His170 has been shown to be partially PEGylated in previous experiments, this was surprisingly not found in this experiment. One possible explanation for this observation is that the bond between the PEG and the His170 residue may be unstable during the sample preparation carried out prior to the peptide mapping. A possible unstable PEGylation such as may be the case here may be avoided by substituting the histidine residue with another residue, in particular a lysine residue if a more stable PEGylation is desired, or a glutamine or arginine residue if PEGylation is to be avoided.

EXAMPLE 20

In Vivo Biological Activity in Rats with Chemotherapy-Induced Neutropenia

The in vivo biological activity of two PEGylated G-CSF variants of the invention was tested in rats with chemotherapy-induced neutropenia. The variants had, relative to SEQ ID NO:1, the amino acid substitutions K16R, K34R, K40R, T105K and S159K (referred to below as "105/159") and K16R, K34R, K40R, Q90K, T105K and S159K (referred to as "90/105/159"), respectively. Both variants were produced in yeast (*S. cerevisiae*) and were conjugated with SPA-PEG-5000 as described above. The in vivo biological activity of a single dose of the two variants was tested against the activity of daily doses of non-conjugated hG-CSF (Neupogen®) and a control (vehicle).

24 hours before administration of the G-CSF samples, the rats were given 50 mg per kg body weight of CPA. The PEGylated variants of the invention were administered as a single dose of 100 µg per kg body weight at time 0, while Neupogen® was administered in daily doses of 30 µg per kg body weight for 5 days (from 0 hours to 96 hours).

The in vivo biological activity was measured as described above ("Measurement of the in vivo biological activity in rats with chemotherapy-induced neutropenia of conjugated and non-conjugated hG-CSF and variants thereof"). The results are shown in FIG. 8 (white blood cell count, WBC) and in FIG. 9 (absolute neutrophil count, ANC).

Figure 8:
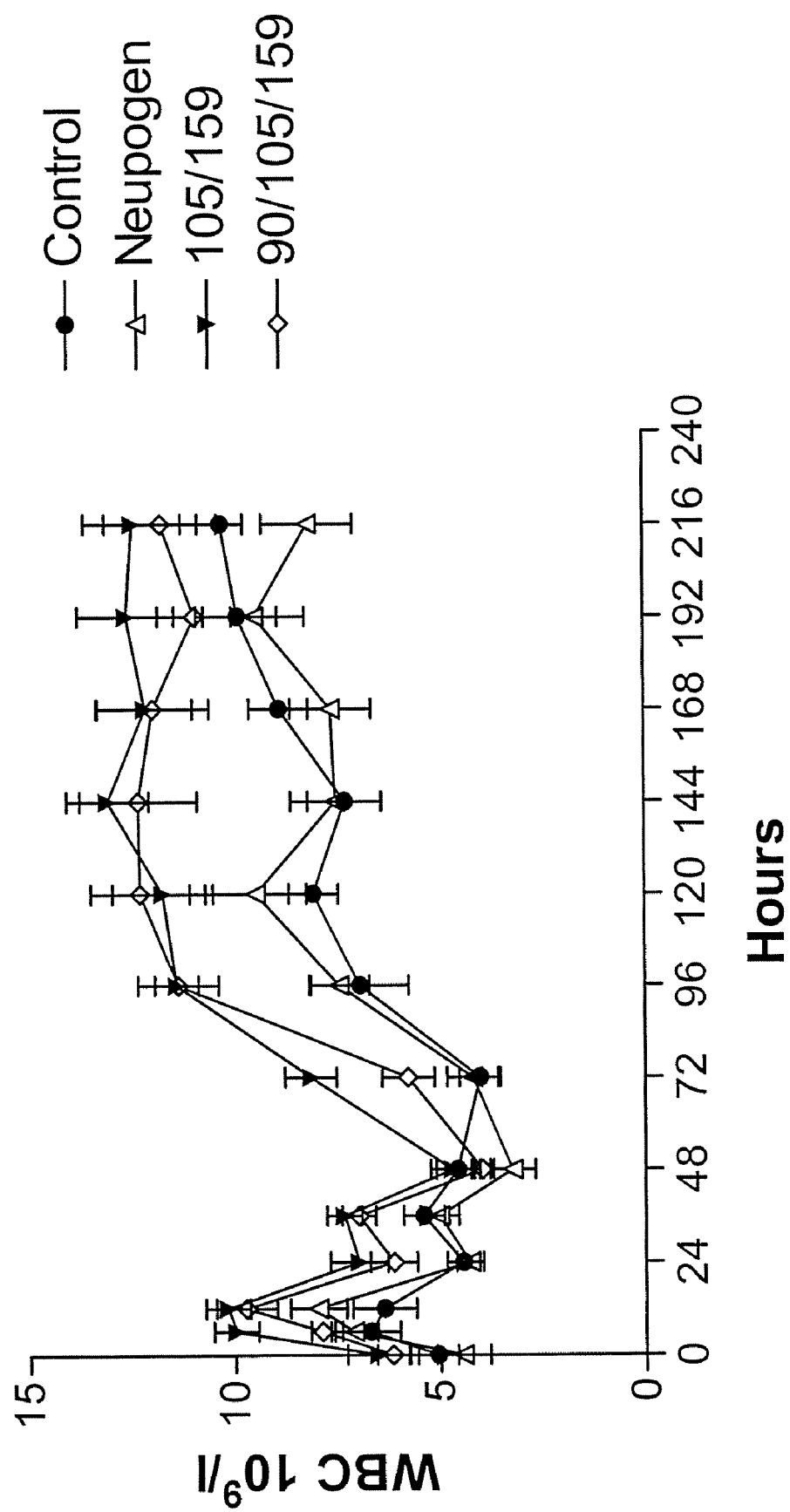
FIG. 8: The in vivo biological activities (white blood cell count) in rats with chemotherapy-induced neutropenia of rhG-CSF (Neupogen®), SPA-PEG 5000-conjugated hG-CSF K16R K34R K40R T105K S159K, and SPA-PEG 5000-conjugated hG-CSF K16R K34R K40R Q90K T105K S159K.

As seen in FIG. 8, administration of 105/159, 90/105/159 and Neupogen® all resulted in an initial increase in white blood cell levels in the first 12 hours, after which the white blood cell levels fell as a result of the chemotherapy, reaching a minimum after about 48 hours. After 48 hours, the numbers of white blood cells increased for all three treatment groups, although the rate of increase was clearly greater for the group treated with the two PEGylated variants of the invention than for the group treated with Neupogen®. Treatment with the PEGylated variants 105/159 and 90/105/159 resulted in a normal level of white blood cells (over $10\times10^9$/l) after 96 hours, while the Neupogen® treated group still had a white blood cell level under $10\times10^9$/l after 120 hours. Since the last of the five daily Neupogen® treatments was given at 96 hours, the white blood cell level in this group fell again after 120 hours. In contrast, the white blood cell level in the two groups treated with a single dose of the PEGylated variants of the invention was relatively stable at just over $10\times10^9$/l from 96 hours and for the duration of the experiment until 216 hours.

Figure 9:
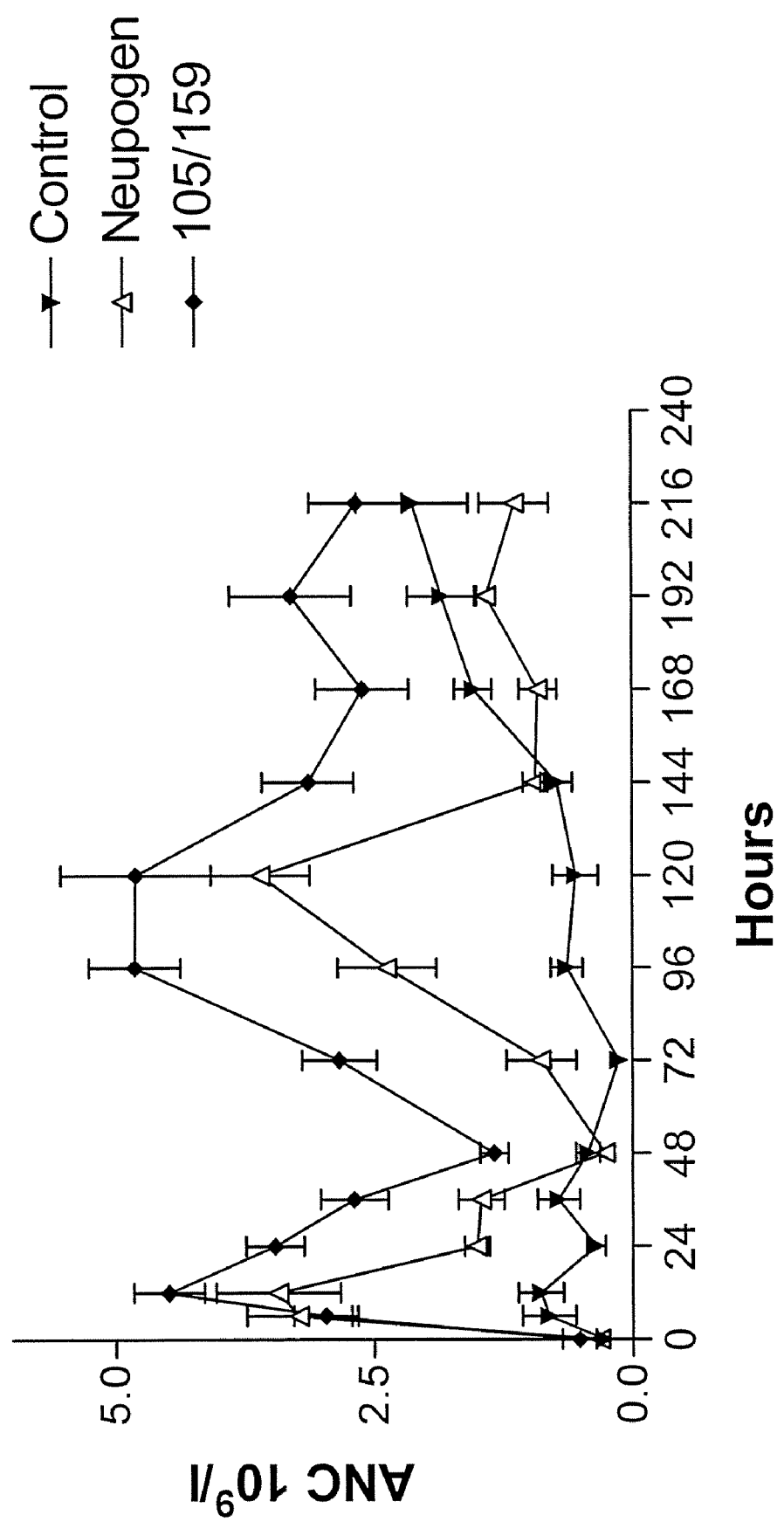
FIG. 9: The in vivo biological activities (absolute neutrophil count) in rats with chemotherapy-induced neutropenia of rhG-CSF (Neupogen®) and SPA-PEG 5000-conjugated hG-CSF K16R K34R K40R T105K S159K.

A similar pattern for the numbers of neutrophils is seen in FIG. 9, which shows that the neutrophil level for the group treated with the PEGylated variant 105/159 increased significantly faster than for the group treated with Neupogen® (ANC was not determined for the 90/105/159 group).

EXAMPLE 21

In Vivo Biological Activity in Rats with Chemotherapy-Induced Neutropenia

The in vivo biological activities of non-conjugated hG-CSF (Neupogen®) and hG-CSF with a single N-terminally linked 20 kDa PEG group (Neulasta®) were compared to two PEGylated G-CSF variants of the invention in rats with chemotherapy-induced neutropenia. These two variants, which were produced in yeast (*S. cerevisiae*) and CHO cells, respectively, had the same amino acid substitutions relative to the sequence of hG-CSF, namely K16R, K34R, K40R, T105K and S159K, and were conjugated to SPA-PEG 5000. The PEGylated variants of the invention, which initially consisted of multi-PEGylated species having 3-6 PEG moieties attached, were separated to give a more uniform product having only 4-5 PEG moieties attached. These variants are referred to below as "G20" (produced in yeast) and "G21" (produced in CHO cells).

The G-CSF samples were administered 24 hours after administration of CPA (90 mg per kg body weight). The PEGylated variants, i.e. Neulasta™, G20 and G21, were administered as a single dose of 100 μg per kg body weight, while Neupogen® was administered in daily doses of 10 μg per kg body weight for seven days.

The in vivo biological activity was measured as described above ("Measurement of the in vivo biological activity in rats with chemotherapy-induced neutropenia of conjugated and non-conjugated hG-CSF and variants thereof"). The results are shown in FIG. 10 (white blood cell count, WBC) and FIG. 11 (absolute neutrophil count, ANC).

Figure 10:
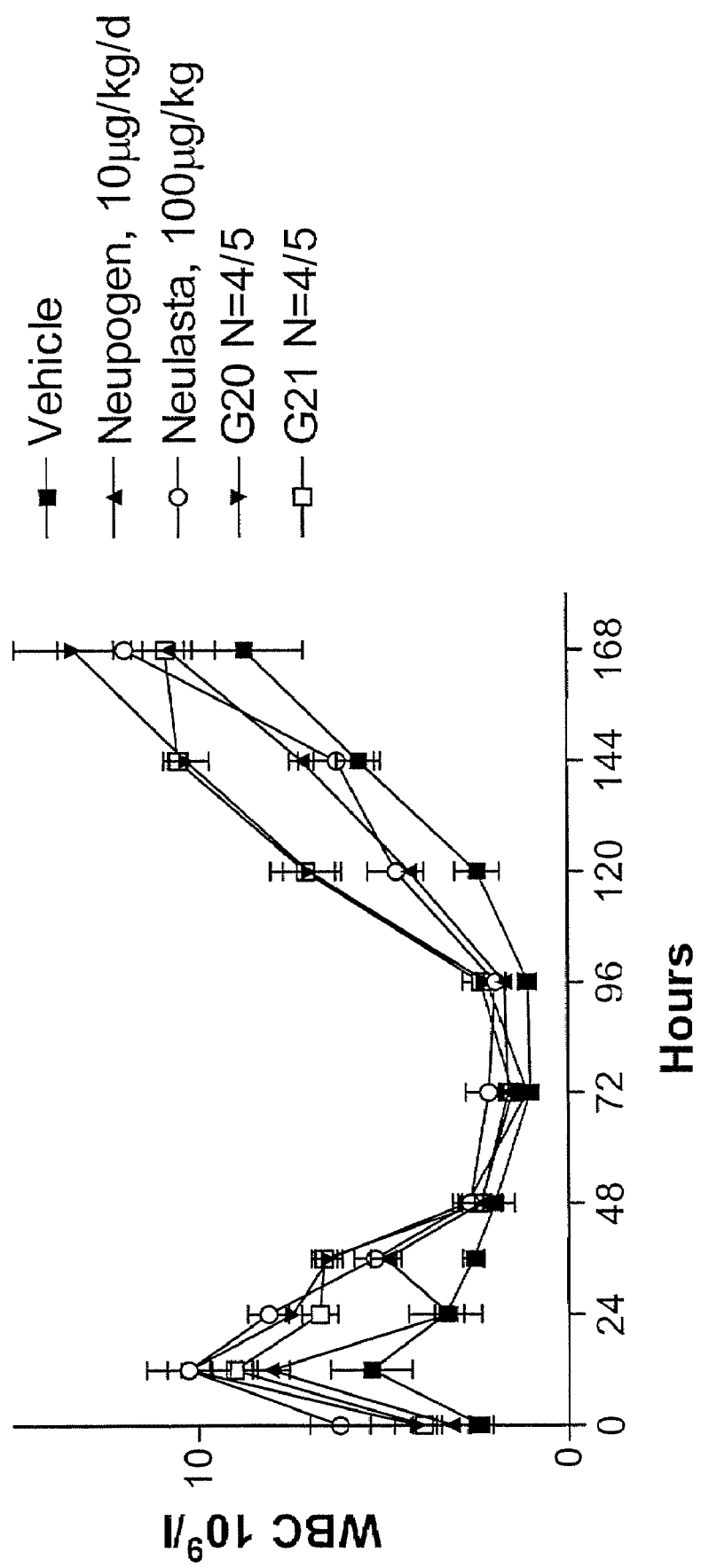
FIG. 10: The in vivo biological activities (white blood cell count) in rats with chemotherapy-induced neutropenia of rhG-CSF (Neupogen®), rhG-CSF with a 20 kDa N-terminal PEG group (Neulasta™), and SPA-PEG 5000-conjugated hG-CSF K16R K34R K40R T105K S159K produced in yeast and in CHO cells.
Figure 11:
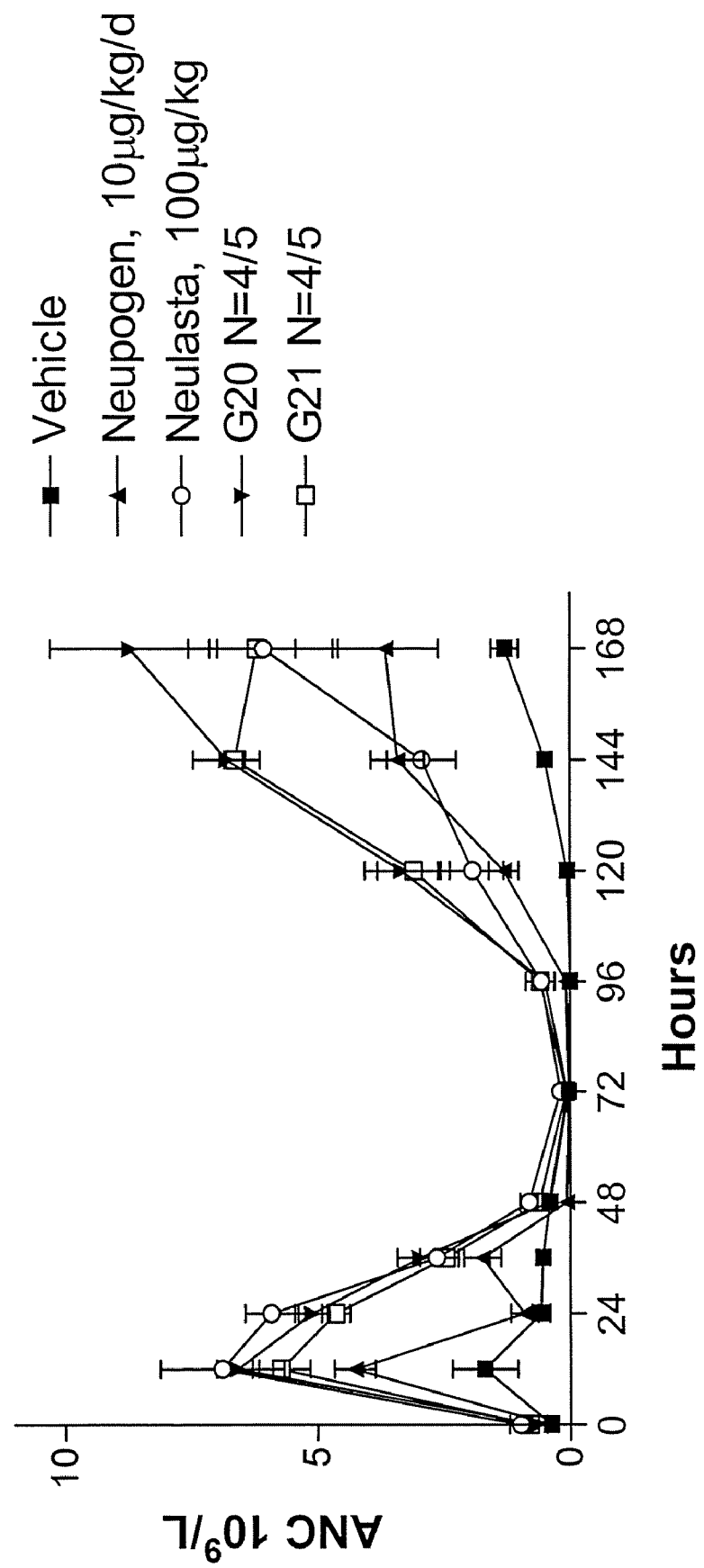
FIG. 11: The in vivo biological activities (absolute neutrophil count) in rats with chemotherapy-induced neutropenia of rhG-CSF (Neupogen®), rhG-CSF with a 20 kDa N-terminal PEG group (Neulasta™), and SPA-PEG 5000-conjugated hG-CSF K16R K34R K40R T105K S159K produced in yeast and in CHO cells.

FIGS. 10 and 11 show that all of the G-CSF compounds induced an initial formation of white blood cells and neutrophils at approximately identical rates during the first 12 hours, after which the levels of white blood cells and neutrophils fell as a result of the chemotherapy. After 96 hours, the levels of white blood cells and neutrophils increased once again in all cases, but the rate of increase was significantly higher for rats treated with G20 or G21 than for rats treated with either Neupogen® or Neulasta®. FIG. 10 shows that the white blood cell levels of rats treated with G20 or G21 reached a normal level of approximately $10^9$/l after 144 hours, while the rats treated with Neupogen® or Neulasta™ did not reach this level until after 168 hours. As shown in FIG. 11, the same pattern is seen when looking at the neutrophil count, i.e. the neutrophil count of rats treated with G20 or G21 reach a normal level approximately 24 hours before rats treated with Neupogen® or Neulasta™ reach a similar level. It may thus be concluded that these PEGylated G-CSF variants of the invention are able to reduce the duration of chemotherapy-induced neutropenia in rats by about 24 hours compared to treatment with the currently available G-CSF products Neupogen® and Neulasta™.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

We claim:

1. A method for preparing a G-CSF conjugate, the method comprising
   (a) providing a polypeptide comprising an amino acid sequence consisting of SEQ ID NO:1 with the substitutions K16R, K34R, K40R, T105K and S159K, and
   (b) reacting the polypeptide with amine-reactive polyethylene glycol moieties under conditions sufficient to produce a G-CSF conjugate having a polyethylene glycol moiety covalently bound to each of at least two attachment groups of the polypeptide,
   wherein the G-CSF conjugate exhibits G-CSF cell proliferation activity.

2. The method of claim 1, wherein the polyethylene glycol moieties each have a molecular weight of about 5 kilodaltons.

3. The method of claim 1, wherein the amine-Reactive polyethylene glycol moieties are mPEG-succinimidyl propionate (mPEG-SPA).

4. The method of claim 3, wherein the amine-reactive polyethylene glycol moieties are mPEG-SPA 5000.

5. The method of claim 1, wherein the amine-reactive polyethylene glycol moieties are attached to the N-terminal amino group and to one or more lysine residues.

6. The method of claim 5, wherein the one or more lysine residues are selected from Lys23, Lys105, and Lys159.

7. The method of claim 1, wherein the step of providing the polypeptide comprises:
   providing an isolated host cell comprising a nucleic acid that comprises a promoter operably linked to a nucleotide sequence encoding the polypeptide,
   culturing the host cell in a nutrient medium under conditions which permit expression of the polypeptide, and
   recovering the polypeptide from the nutrient medium or from the cultured host cells.

8. The method of claim 7, wherein the host cell is a bacterial host cell.

9. The method of claim 7, wherein the host cell is a glycosylating host cell.

10. The method of claim 9, wherein the host cell is selected from an S. cerevisiae cell, a Pichia pastoris cell, a CHO cell, a BHK cell, an HEK 293 cell, and an SF9 cell.

11. The method of claim 8, wherein the host cell is E. coli.

12. The method of claim 10, wherein the host cell is an S. cerevisiae cell.

13. The method of claim 10, wherein the host cell is a CHO cell.

14. The method of claim 7, wherein the polypeptide is recovered from the nutrient medium.

15. The method of claim 7, wherein the polypeptide is recovered from the cultured host cells.

16. The method of claim 7, wherein the method further comprises a purification step to purify the recovered polypeptide.

17. The method of claim 16, wherein the purification step comprises a chromatography method.

18. The method of claim 17, wherein the chromatography method is ion exchange chromatography.

19. The method of claim 1, wherein the amine-reactive polyethylene glycol moieties comprise a succinimidyl group.

20. The method of claim 1, wherein the method further comprises a purification step.

21. The method of claim 20, wherein the purification step comprises cation exchange chromatography.

22. The method of claim 1, wherein the conditions are a molar excess of the amine-reactive polyethylene glycol moieties relative to the number of polypeptide attachment sites.

23. The method of claim 1, wherein the conditions are a molar ratio of amine-reactive polyethylene glycol moieties to polypeptide that is greater than 10:1 and up to about 100:1.

24. The method of claim 22, wherein the conditions are about a 5:1 molar excess of the amine-reactive polyethylene glycol moieties relative to the number of polypeptide attachment sites.

25. The method of claim 22, wherein the conditions are about a 10:1 molar excess of the amine-reactive polyethylene glycol moieties relative to the number of polypeptide attachment sites.

26. The method of claim 22, wherein the conditions are about a 1000:1 molar excess of the amine-reactive polyethylene glycol moieties relative to the number of polypeptide attachment sites.

27. The method of claim 1, wherein the G-CSF conjugate comprises 2-8 polyethylene glycol moieties.

28. The method of claim 1, wherein the G-CSF conjugate comprises 3-6 polyethylene glycol moieties.

29. The method of claim 19, wherein the amine-reactive polyethylene glycol moiety is a methoxypolyethylene glycol (mPEG) moiety.

30. The method of claim 29, wherein the amine-reactive polyethylene glycol moiety is a linear molecule.

* * * * *